United States Patent [19]

Roger et al.

[11] Patent Number: 4,983,726

[45] Date of Patent: Jan. 8, 1991

[54] PROCESS FOR PREPARING NITROSOUREA DERIVATIVES

[75] Inventors: Pierre Roger, Montigny-les-Bretonneux; Patrick Choay, Paris; Claude Monneret; Jean-Paul Fournier, both of Paris, all of France

[73] Assignee: Sanofi S.A., Paris, France

[21] Appl. No.: 440,905

[22] Filed: Nov. 24, 1989

Related U.S. Application Data

[60] Division of Ser. No. 181,760, Apr. 14, 1988, abandoned, which is a continuation-in-part of Ser. No. 732,007, Apr. 24, 1985, Pat. No. 4,902,791.

[30] Foreign Application Priority Data

Aug. 30, 1983 [FR] France ................ 83 13878
Apr. 22, 1987 [FR] France ................ 87 05708
Apr. 22, 1987 [FR] France ................ 87 05709

[51] Int. Cl.$^5$ .............. A61K 31/04; C07C 125/065; C07C 111/00; C07H 5/06
[52] U.S. Cl. ................. 536/17.7; 514/908; 536/53; 536/55
[58] Field of Search .............. 536/17.7, 53, 55; 514/25, 908

[56] References Cited

U.S. PATENT DOCUMENTS

| | | | |
|---|---|---|---|
| 3,940,383 | 2/1976 | Fujiwara et al. | 536/17.7 |
| 4,241,052 | 12/1980 | Tsujihara | 536/53 |
| 4,273,766 | 6/1981 | Stanek | 536/17.7 |
| 4,472,379 | 9/1984 | Suami et al. | 536/17.7 |
| 4,472,573 | 9/1984 | Morikawa et al. | 536/17.7 |
| 4,593,090 | 6/1986 | Kimura et al. | 536/17.7 |

FOREIGN PATENT DOCUMENTS 62329 3/1982 European Pat. Off. .
67019 7/1982 European Pat. Off. .
8313848 11/1985 France .

*Primary Examiner*—Ronald W. Griffin
*Attorney, Agent, or Firm*—Foley & Lardner, Schwartz, Jeffery, Schwaab, Mack, Blumenthal & Evans

[57] ABSTRACT

The invention relates to nitrosourea derivatives, a process for their preparation and pharmaceutical compositions containing them.

The nitrosourea derivatives of the invention correspond to the following formula (I):

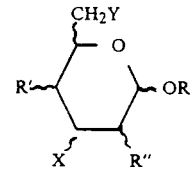

in which: R can represent a hydrogen atom or an alkyl group from 1 to 30 carbon atoms, X represents a hydroxy group or an $-NR_1R_2$ group, Y represents a hydrogen atom, a hydroxy group or an $-NR'_1R'_2$ group, where $R_1$ and/or $R'_1$ each represent a hydrogen atom or a

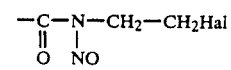

group, Hal being a halogen, and $R_2$ and/or $R'_2$ can each represent a hydrogen atom or an alkyl group comprising from 1 to 6 carbon atoms, R' and R" can represent hydrogen or OH, provided that at least X represents

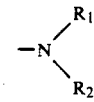

with $R_1$ representing

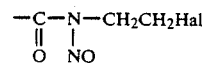

or Y represents

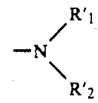

with $R'_1$ representing

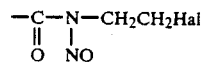

and provided that either R' represents hydrogen or R" represents hydrogen, and R' and R" cannot be simultaneously hydrogen atoms.

These compounds present an antitumor activity.

29 Claims, No Drawings

PROCESS FOR PREPARING NITROSOUREA DERIVATIVES

CROSS - REFERENCE TO RELATED APPLICATIONS

This application is a division of application Ser. No. 07/181,760, filed Apr. 14, 1988, now abandoned, which is a continuation-in-part of serial No. 732,007, filed Apr. 24, 1985, now U.S. Pat. No. 4,902,791.

BACKGROUND OF THE INVENTION

The present invention relates to novel nitrosourea derivatives and, more specifically, to novel 2-desoxy-sugar-nitrosoureas and 4-desoxy-sugar-nitrosoureas, to processes for their preparation and to their therapeutic uses.

It is known that various nitrosoureas have powerful cytostatic and oncostatic activity detected within the framework of pharmacological experiments and clinical treatment : this is the case, in particular, of (1,3-bis-2-chloroethyl)-1-nitrosourea [BCNU] marketed under the trademark "BICNU" (cf. Dictionnaire VIDAL 1984), of 1-(2-chloro-ethyl)-3-cyclohexyl nitrosourea [CCNU] marketed under the trademark "BELUSTINE" (cf. Dictionnaire VIDAL 1984) and 1-(2-chloro-ethyl)-3-(4-methyl-cyclohexyl)-nitrosourea [Me CCNU] : cf. G. MATHE and Y. KENIS : Expansion Scientifique, 1975, 3rd Ed. TLa Chimiotherapie des cancers (leucemies, hematosarcomes et tumeurs solides)" and T. H. WASSERMAN, M. SLAVIK & S. K. CARTER, Cancer Treat. Rev., 1974, 1, p. 131, "Review of CCNU in clinical cancer therapy". G. P. WHEELER et al. (Cancer Res., 1974, 34, 194) attribute their oncostatic action to an alkylation and a carbomoylation of proteins. It has also been suggested that their lypophilic character is essential in so far as it conditions the passage through cell membranes in particular the blood-brain barrier. However, these compounds have the drawback of showing certain toxicity, particularly hematological, at the doses at which they are revealed to be active. Consequently, this toxicity limits their use at doses less than those which seem necessary for the removal of cancer cells and has incited a team of researchers to aim at obtaining medicaments more active and less toxic than the preceding ones, by synthesizing derivatives of nitro soureas whose hydrophilic character is increased with respect to the preceding ones, such as sugar-nitrosoureas, in which the sugar molecule is ribose, xylose or glucose : cf. J. L. IMBACH et al, Biomedicine, 1975, 23, pp. 410-413, "The oncostatic and immunosuppressive action of new nitrosourea derivatives containing sugar radicals". Thus these authors have established the oncostatic action of the following four compounds on L 1210 leucemia and their low toxicity:1-(2-chloro-ethyl)3-(ribofuranosyl-2', 3'-isopropylidene-5-paranitro benzoate)-nitrosourea [RFCNU], 3-(2-chloro-1-ethyl-2'-desoxy-glucopyranosyl-14, 3',4''',6'-tetracetate)-nitrosourea [GCNU], 1-(2-chloro-ethyl) 3-(ribopyranosyl-2',3',4'-triacetate)-nitrosourea [RPCNU] and 1-(2-chloro ethyl) 3-(xylopyranosyl 2',3',4'-triacetate)-nitrosourea [XPCNU]. These compounds are prepared by reacting the appropriate amino-sugar with 2-chloro-ethyl isocyanate, then by proceeding with nitrosation of the urea obtained..

These compounds are in oily form, a difficult physical state to handle in therapeutics. This is why, within the scope of the experiments been had to their solidification by blocking the hydroxy groups.

In a subsequent work J. L. MONTERO et al (Eur. J. Med. Chem. Chimica Therapeutica, mars/avril 1976, 11, n 2, pp. 183-187 : "Synthese de nouvelles glycosyl-nitrosourées à visées oncostatiques - les 1-nitrosoureido-1-desoxy-glucopyranoses"), described glycosyl-nitrosoureas in which the sugar-nitrogen bond is located in an anomeric position, which has oncostatic activity, namely 1-[3-(2-position, which has oncostatic activity, namely 1-[3-(2-chloro-ethyl) 3-nitroso-ureido]-1-beta-D-glucopyranose and 2,3,4,6-tetra-O-acetyl 1-[3-(2-chlor-ethyl) nitroso-3-ureido]-1-desoxy-beta-D-glucopyranose, and which represents in addition the advantage of lower toxicity on the bone marrow and not being diabetogenic, whereas streptozotocine or 2-desoxy-2-(3-methyl-2-nitrosoureido)-D-glucopyranose, which is a compound of natural origin, presents antibiotic, antineoplasic properties, and also presents undesirable diabetogenic properties as well as a high renal and hematological toxicity (ci. Drugs of the future, vol. IV, n 2, 1979, pp. 137-139).

One of the aspects of the invention is to provide novel nitrosourea derivatives, for which the profile of the activity curve shows its maximum at a dosage far below the threshold of the toxicity.

Another aspect of the invention is to provide novel nitrosourea derivatives having a good therapeutic index.

It is another aspect of the invention to provide also novel nitrosourea derivatives having physical properties enabling their use in therapeutics.

Another aspect of the invention is to provide novel nitrosourea derivatives having a solid and stable form.

SUMMARY OF THE INVENTION

According to the invention these various aspects are achieved by means of a novel series of derivatives of 2-desoxy-sugar-nitrosoureas and 4-desoxy-sugar-nitrosoureas, which are distinguished from known nitrosourea derivatives, particularly by the nature of the oside synthon, which is 2-desoxy-sugar or a 4-desoxy-sugar.

It has been observed that by resorting to 2-desoxy-sugar or a 4-desoxy-sugar, substituted on the 3 and/or at the 6 carbon of the above-said sugar, by a nitrosourea group, and which can carry different substituents on the carbon at the 4 position of the above-said sugar, when it relates to a 2-desoxy-sugar or on the carbon at the 2 position of the above-said sugar, when it relates to a 4-desoxy-sugar, novel nitrosourea derivatives are obtained whose activity is considerably increased and whose toxicity is low with respect to the compounds already known. One of the interests of these derivatives can be connected with the hypothesis according to which the 2-desoxy-sugars and the 4-desoxy-sugars have a certain lability at the level of the oside linkage, which can result in the formation of a free sugar in certain biological media and permit the provision of compounds firstly lipophilic, which then become hydrophilic, which would make easier the passage of cellular barriers and would account for an increase of antitumor activity.

An object of the invention is to provide novel nitrosourea derivatives, characterised in that they correspond to the following general formula (I):

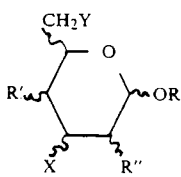 (I)

in which:
R represents a hydrogen atom, an alkyl group from 1 to 30, preferably 1 to 12 carbon atoms or an aralkyl group from 7 to 12, preferably 7 to 9 carbon atoms, optionally substituted by one or several, particularly up to 3, halogen atoms, $NO_2$, $NH_2$, $CF_3$ groups or alkoxy groups of 1 to 4 carbon atoms, X represents a hydroxy group or an $NR_1R_2$ group Y represents a hydrogen atom a hydroxy group or an

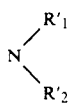

group where $R_1$ and/or $R'_1$ each represent a hydrogen atom or a

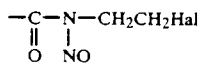

group, Hal being a halogen, preferably Cl, and $R_2$ and/or $R'_2$ each represent a hydrogen atom, an alkyl group comprising from 1 to 6 carbon atoms, an aralkyl group comprising 7 to 12, preferably 7 to 9 carbon atoms, a cycloalkyl group comprising from 3 to 6 carbon atoms, an aryl group of 4 to 10 carbon atoms, the aryl and aralkyl groups being possibly substituted by one or several, particularly up to 3, halogen atoms, $NO_2$, $NH_2$, $CF_3$ groups or alkoxy groups of 1 to 4 carbon atoms, R' and R" represent hydrogen, OM, M representing an alkyl group comprising from 1 to 30, preferably from 1 to 12 carbon atoms, an aryl group from 4 to 10 carbon atoms, an aralkyl group comprising from 7 to 12, preferably from 7 to 9 carbon atoms, the aryl and aralkyl groups being possibly substituted by 1 or several, particularly up to 3, halogen atoms, $NO_2$, $NH_2$,$CF_3$ groups or alkoxy groups from 1 to 4 carbon atoms, or M representing an acyl group from 2 to 8 carbon atoms, preferably 2 or 3, or an aroyl group from 5 to 12, preferably 5 to 9 carbon atoms, unsubstituted or substituted by one or several, particularly up to 3, $NO_2$, $NH_2$, $CF_3$ groups, halogen, alkoxy of 1 to 4 carbon atoms, provided that either R' or R" represents hydrogen, R' and R" being not simultaneously hydrogen and provided that at least X represents

with $R_1$ representing

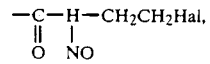

or Y represents

with $R'_1$ representing

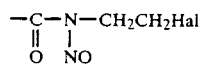

In a preferred class of compounds of the invention, R' represents H and R" represents OH.

In another preferred class of compounds of the invention R" represents H and R' represents OH.

In Formula I and certain of the Formulas following linkages have been shown between the groups R, R', R",$CH_2Y$ and X on the one hand and the ring structure on the other hand, by the symbol ∼. This representation means that each of the R,R',R",$CH_2Y$ and X groups can be either at the $\alpha$ position or at the $\beta$ position, according to the HAYWORTH representation, and in an arrangement compatible with the stereochemical requirements.

In the rest of the description, the term alkyl includes linear, branched or cyclic alkyl groups (cycloalkyl).

A preferred class of compounds according to the invention is constituted by the compounds corresponding to the Formula II below:

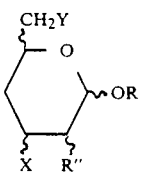 (II)

in which
R represents a hydrogen atom, an alkyl group from 1 to 30, preferably 1 to 12 carbon atoms, or an aralkyl group from 7 to 12, preferably 7 to 9 carbon atoms, optionally substituted by one or severals particularly up to 3 halogen atoms $NO_2$,$NH_2$,$CF_3$ groups or alkoxy groups from 1 to 4 carbon atoms.

X represents a hydroxy group or an $NR_1R_2$ group

Y represents
a hydrogen atom,
a hydroxy group or an

group
where $R_1$ and/or $R'_1$ each represent a hydrogen atom or a

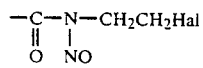

group, Hal being a halogen, preferably Cl, and $R_2$ and/or $R'_2$ represent a hydrogen atom, an alkyl group comprising from 1 to 6 carbon atoms, an aralkyl group comprising from 7 to 12, preferably 7 to 9 carbon atoms, a cycloalkyl group comprising from 3 to 6 carbon atoms, an aryl group from 4 to 10 carbon atoms, the aryl and aralkyl groups being optionally substituted by one or several, particularly up to 3 halogen atoms, $NO_2$, $NH_2$, $CF_3$ group or alkoxy groups of 1 to 4 carbon atoms, R" represents preferably OH, but can be replaced by OM, M representing an alkyl group comprising from 1 to 30, preferably 1 to 12 carbon atoms, an aryl group from 4 to 10 carbon atoms, an aralkyl group comprising from 7 to 12, preferably 7 to 9 carbon atoms, the aryl and aralkyl groups being optionally substituted by one or several, particularly up to 3 halogen atoms, $NO_2$, $NH_2$, $CF_3$ groups or alkoxy groups of 1 to 4 carbon atoms, or M representing an acyl group from 2 to 8 carbon atoms, preferably 2 or 3, or an aroyl group from 5 to 12, preferably 5 to 9 carbon atoms, unsubstituted or substituted by one or several, particularly up to 3, $NO_2$, $NH_2$, $CF_3$ groups, halogen, alkoxy from 1 to 4 carbon atoms, provided that at least X represents

with $R_1$ representing

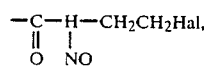

or Y represents

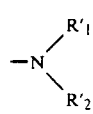

with $R'_1$ representing

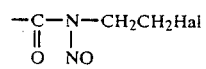

These compounds of formula (II) represent the particular case of formula (I) in which R' represents hydrogen.

Among the compounds of formula (II), a preferred class of compounds according to the invention is constituted by those of formula (III) below:

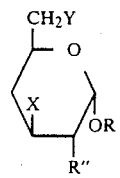

in which R, R", X and Y have the above-indicated meanings.

The compounds according to the invention of Formula III belong to the class of 4-desoxy,alpha-D-xylohexopyranoside compounds.

Among the compounds of Formula (II), a preferred class of compounds according to the invention is constituted by those of Formula IV below:

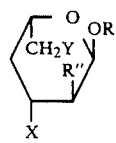

in which R, R", X and Y have the previously indicated meanings.

The compounds of Formula (IV) belong to the clas class of 4-desoxy,alpha-L-xylohexopyranoside compounds.

A particularly preferred class of compounds according to the invention is constituted by the compounds corresponding to the Formula V below:

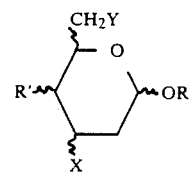

in which p1 R represents a hydrogen atom, an alkyl group from 1 to 30, preferably 1 to 12 carbon atoms or an aralkyl group from 7 to 12, preferably 7 to 9 carbon atoms, optionally substituted by one or several, particularly up to 3, halogen atoms, $NO_2$,$NH_2$,$CF_3$ groups or alkoxy groups of 1 to 4 carbon atoms.

X represents a hydroxy group or an $NR_1R_2$ group

Y represents
  a hydrogen atom,
  a hydroxy group or an

group
where $R_1$ and/or $R'_1$ each represent a hydrogen atom or a

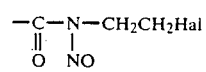

group, Hal being halogen, preferably Cl, and $R_2$ and/or $R'_2$ each represent a hydrogen atom, an alkyl group comprising 1 to 6 carbon atoms, an aralkyl group comprising 7 to 12, preferably 7 to 9 carbon atoms, a cycloalkyl group comprising from 3 to 6 carbon atoms, an aryl group of 4 to 10 carbon atoms, the aryl and aralkyl groups being optionally substituted by one or several, particularly up to 3, halogen atoms, $NO_2, NH_2, CF_3$ groups of alkoxy groups of 1 to 4 carbon atoms R' represents preferably OH, but OH can be replaced by OM. M representing an alkyl group comprising from 1 to 30, preferably from 1 to 12 carbon atoms, an aryl group of 4 to 10 carbon atoms, and aralkyl group comprising 7 to 12, preferably 7 to 9 carbon atoms, the aryl and aralkyl groups being optionally substituted by one or several, particularly up to 3, halogen atoms, $NO_2, NH_2, CF_3$ groups or alkoxy groups from 1 to 4 carbon atoms, or M representing an acyl group of 2 to 8 carbon atoms, preferably 2 or 3, or an aroyl group from 5 to 12, preferably 5 to 9 carbon atoms, unsubstituted or substituted by one or several, particularly up to 3, $NO_2, NH_2, CFhd 3$ groups, halogen, alkoxy of 1 to 4 carbon atoms provided that at least X represents

with $R_1$ representing

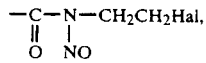

or Y represents

with $R'_1$ representing

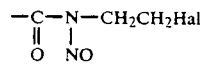

These compounds of Formula V represent the particular case of Formula I in which R" represents a hydrogen atom.

Among the compounds of Formula V, a preferred class of compounds of the invention is constituted by those of Formula (VI) below:

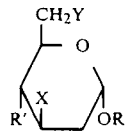

in which R, R', X and Y have the previously indicated meanings.

The compounds of formula (VI) belong to the class of 2-desoxy, alpha-D-arabinohexopyranoside compounds.

Among the compounds of formula (V), another preferred class of compounds provided by the invention is constituted by those of the following formula (VII):

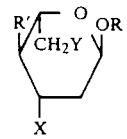

in which R, R', X and Y have the previously indicated meanings.

These compounds belong to the class of 2-desoxy, alpha-L-arabinohexopyranoside compounds.

A preferred class of compounds according to the invention is constituted by those of formulae (I), (II), (III), (IV), (V), (VI), and (VII) in which:
R represents an alkyl group from 1 to 12 carbon atoms, aralkyl from 7 to 12 atoms;
R' or R" represents an OM group, M being an alkyl group comprising from 1 to 12 carbon atoms, an aryl group comprising 4 to 10 carbon atoms;
X represents an $NR_1R_2$ group, $R_1$ representing

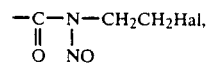

Hal being a halogen, particularly Cl;
Y represents a hydrogen atom or a hydroxy group.

Another preferred class of compounds according to the invention is constituted by those of formulae (I), (II), (III), (IV), (V), (VI), and (VII) in which:
R represents an alkyl group from 1 to 12 carbon atoms, halogenoaralkyl from 4 to 10 carbon atoms;
R' or R" represents an OM group, M being an acyl group of 2 to 8 carbon atoms, an aroyl group from 5 to 12 carbon atoms;
X represents an $NR_1R_2$ group, $R_1$ representing

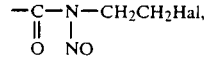

Hal being a halogen, particularly Cl,
Y represents a hydrogen atom or a hydroxy group.

Another preferred class of compounds according to the invention is consitituted by those of Formulas (I), (II), (III), (IV), (V), (VI), and (VII) and in which:
R represents an alkyl group from 1 to 12 carbon atoms, an aralkyl group from 7 to 12 carbon atoms;
R' or R" represents OH;
X represents an $NR_1R_2$ group, $R_1$ representing

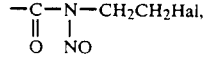

Hal representing a halogen, particularly Cl,
Y represents a hydrogen atom.

Another class of preferred compounds according to the invention is constituted by those of Formula (I), (II), (III), (IV), (V), (VI) and (VII) in which:
R represents an alkyl group from 1 to 12 carbon atoms, an aralkyl group from 7 to 12 carbon atoms;
R' and R" represent OH;

X represents an alkyl amino group, in which the alkyl group has 1 to 6 carbon atoms, or arylamino in which the aryl group has 4 to 10 carbon atoms, and Y represents $NR'_1NR'_2$, $R'_1$ representing

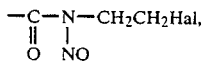

Hal representing a halogen, particularly Cl.

Another class of preferred compounds according to the invention is constituted by those of Formula (I), (II), (III), (IV), (V), (VI) and (VII) in which:

R represents an alkyl group of 1 to 12 carbon atoms, an aralkyl group of 7 to 12 carbon atoms;

R' or R'' represents OH;

X represents a hydroxy group,

Y represents $NR'_1R'_2$, $R'_1$ representing

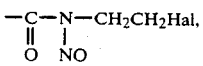

Hal representing halogen, particularly Cl.

Another class of preferred compounds according to the invention is constituted by those of Formula (I), (II), (III), (IV), (V), (VI) and (VII) in which:

R represents an alkyl group of 1 to 12 carbon atoms, an aralkyl group of 7 to 12 carbon atoms, R' and R'' represent OH, X represents an $NR_1R_2$ group, $R_1$ representing

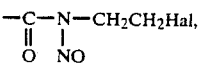

Hal being a halogen, particularly Cl,

Y represents an alkylamino group, in which the alkyl group has 1 to 6 carbon atoms or arylamino in which the aryl group has 4 to 10 carbon atoms.

Another preferred class of compounds according to the invention is constituted by those of Formula (V), (VI) and (VII) in which:

R represents an alkyl group from 1 to 12 carbon atoms, aralkyl from 7 to 12 carbon atoms;

R' represents an OM group, M being an alkyl group comprising 1 to 12 carbon atoms, an aryl group comprising 4 to 10 carbon atoms;

X represents a group $NR_1R_2$, $R_1$ representing

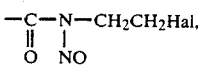

Hal being a halogen, particularly Cl,

Y represents a hydrogen atom or a hydroxy group.

Another preferred class of compounds according to the invention is constituted by those of Formulas (V), (VI) and (VII) in which:

R represents an alkyl group from 1 to 12 carbon atoms, a halogenoaralkyl of 4 to 10 carbon atoms;

R' represents an OM group, M being an acyl group of 2 to 8 carbon atoms, an aroyl group from 5 to 12 carbon atoms;

X represents an $NR_1R_2$ group, $R_1$ representing

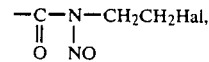

Hal being a halogen, particularly Cl,

Y represents a hydrogen atom or a hydroxy group.

Another preferred class of compounds according to the invention is constituted by the Formulas (V), (VI) and (VII) and in which:

R represents an alkyl group from 1 to 12 carbon atoms, an arylkyl group from 7 to 12 carbon atoms;

R' represents OH;

X represents an $—NR_1R_2$ group, $R_1$ representing

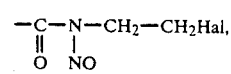

Hal being a halogen, particularly Cl,

Y represents a hydrogen atom.

Another class of preferred compounds according to the invention is constituted by those of Formulas (V), (VI), and (VII) in which:

R represents an alkyl group from 1 to 12 carbon atoms, an aralkyl group from 7 to 12 carbon atons;

R' represents OH;

X represents an alkylamino group, in which the alkyl group has 1 to 6 carbon atoms, or arylamino in which the aryl group has 4 to 10 carbon atoms and Y represents $—NR'_1R'_2$, $R'_1$ representing

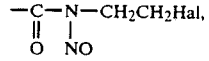

Hal being a halogen, particularly Cl.

Another class of preferred compounds according to the invention is constituted by those of Formula (V), (VI), and (VII) in which:

R represents an alkyl group of 1 to 12 carbon atoms, an aralkyl group of 7 to 12 carbon atoms;

R' represents OH;

X represents a hydroxy group;

Y represents $—NR'_1R'_2$, $R'_1$ representing

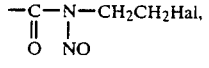

Hal being a halogen, particularly Cl.

Another class of preferred compounds according to the invention is constituted to those of Formula (V), (VI) and (VII) in which:

R represents an alkyl group of 1 to 12 carbon atoms, an aralkyl group 7 to 12 carbon atoms;

R' represents OH;

X represents an $NR_1R_2$ group, $R_1$ representing

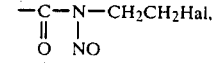

Hal being a halogen atom, particularly Cl,

Y represents an alkylamino group, in which the alkyl group has 1 to 6 carbon atoms or arylamino in which the aryl group has 4 to 10 carbon atoms.

In accordance with the invention, the novel derivatives of nitrosoureas of the general Formula I are 2,3,6-tridesoxy α-D-arabinohexopyranosyl-nitrosoureas, 2,3-didesoxy-α-D-arabinohexopyranosyl-nitrosoureas, 2,6-didesoxy-α-D-arabinohexopyranosyl-nitrosoureas, 2,3,6-tridesoxy α-L-arabinohexopyranosyl-nitrosoureas, 2,3-didesoxy-α-L-arabinohexopyranosyl-nitrosoureas, 2,6-didesoxy-α-L-arabinohexopyranosyl-nitrosoureas, 3,4,6-tridesoxy α-D-xylohexopyranosyl-nitrosoureas, 3,4-didesoxy α-D-xylohexopyranosyl-nitrosoureas, 4,6-didesoxy α-D-xylohexopyranosyl-nitrosoureas, 3,4,6-tridesoxy α-L-xylohexopyranosyl-nitrosoureas, 3,4-didesoxy α-L-xylohexopyranosyl-nitrosoureas, 4,6-didesoxy alpha-L-xylohexopyranosyl-nitrosoureas.

A preferred class of compounds according to the invention is constituted by those of the following formula:

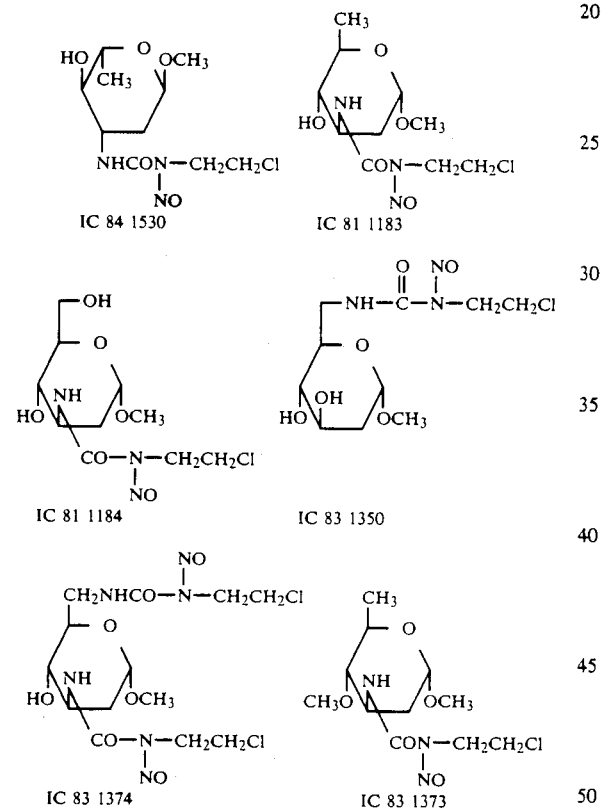

It is also an object of the present invention to provide a process for the preparation of the novel derivatives of general Formula I according to the invention, which consists of reacting, in a first step, an oxide group of general Formula (I bis)

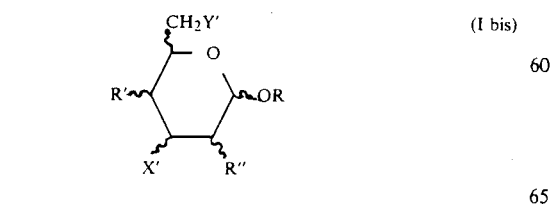

(I bis)

in which R, R' and R'' have the meanings indicated above.

X' represents a hydroxy or —NHR$_2$ group;

Y' represents a hydrogen atom, a hydroxy group or —NHR'$_2$

R$_2$ and R'$_2$ identical or different, represent independently of one another, a hydrogen atom, an alkyl group from 1 to 6 carbon atoms, an aralkyl group from 7 to 12 carbon atoms, aryl from 4 to 10 carbon atoms, cycloalkyl from 3 to 6 carbon atoms, the aryl and aralkyl groups being optionally substituted by 1 or several particularly up to 3, halogen atoms, NO$_2$, NH$_2$CF$_3$ groups or alkoxy groups from 1 to 4 carbon atoms, and in which one at least of the groups X' or Y' represent NHR$_2$ or NHR'$_2$ on 2-halogeno-ethyl isocyanate to convert the —NHR$_2$ or NHR'$_2$ group of the compound of Formula I bis respectively into

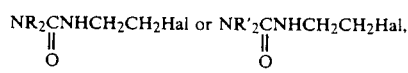

Hal being a halogen atom, particularly chlorine, and in a second step, subjecting the compound obtained at the end of the first step to nitrosation, by means of a nitrite of an alkali metal, preferably sodium nitrite, to convert the

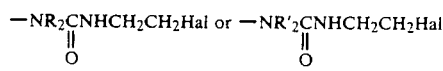

groups respectively into

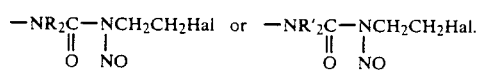

The process described above can be illustrated by the following diagram in the case where X' represents NHR$_2$.

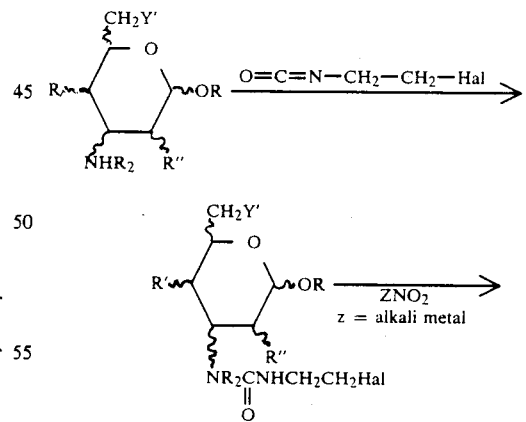

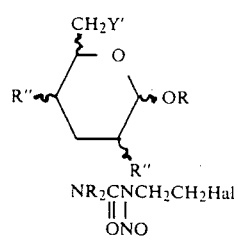

In the case where Y' represents —NHR'₂, the process described above can be illustrated by the following diagram:

$$\text{R'} \underset{X'}{\overset{CH_2NHR'_2}{\underset{R''}{\bigcirc}}} OR \xrightarrow{O=C=N-CH_2-CH_2Hal}$$

$$\text{R'} \underset{X'}{\overset{CH_2NR'_2CNHCH_2CH_2Hal}{\underset{R''}{\underset{\parallel}{\underset{O}{\bigcirc}}}}} OR \xrightarrow[Z = \text{alkali metal}]{ZNO_2}$$

$$\text{R'} \underset{X'}{\overset{CH_2NR'_2C-NCH_2CH_2Hal}{\underset{R''}{\underset{\parallel\;\;|}{\underset{O\;\;NO}{\bigcirc}}}}} OR$$

The present invention relates also to a process for preparing novel compounds of the general formula VI according to the invention, which consists of reacting, in a first step, an oxide group of the general formula VI bis:

$$\text{R'} \underset{X'}{\overset{CH_2Y'}{\bigcirc}} OR \quad \text{(VI bis)}$$

in which:
R and R' are such as defined above;
X' represents an —NHR₂ or hydroxy group;
Y' represents a hydrogen atom, a hydroxy group or —NHR'₂
R₂ and R'₂, identical or different, represent independently of one another a hydrogen atom, an alkyl group from 1 to 6 carbon atoms, an aralkyl group of 7 to 12 carbon atoms, aryl from 4 to 10 carbon atoms, cycloalkyl from 3 to 6 carbon atoms, the aryl and aralkyl groups being optionally substituted by one or several, particularly up to 3, halogen atoms, groups NO₂, NH₂, CF₃ or alkoxy groups from 1 to 4 carbon atoms, and in which one at least of the groups X' and Y' represents p13 NHR₂ or NHR'₂
On a 2-halogeno-ethyl isocyanate to convert the —NHR₂ or NHR'₂ group of the compound of Formula VI bis respectively into $$-NR_2\underset{\parallel}{C}NHCH_2CH_2Hal \text{ or } -NR'_2\underset{\parallel}{C}NHCH_2CH_2Hal,$$
$$O \qquad\qquad O$$

Hal being a halogen atom, particularly chlorine, and in a second step to subject the compound obtained at the end of the preceding step to nitrosation, by means of an alcali metal nitrite, preferably sodium nitrite to convert the groups $$-NR_2\underset{\parallel}{C}NHCH_2CH_2Hal \text{ or } -NR'_2\underset{\parallel}{C}NHCH_2CH_2Hal$$
$$O \qquad\qquad O$$

respectively into $$-NR_2\underset{\underset{ONO}{\parallel\;|}}{C}NCH_2CH_2Hal \text{ or } NR'_2\underset{\underset{ONO}{\parallel\;|}}{C}NCH_2CH_2Hal.$$

The present invention relates also to a process for preparing novel compounds of the general formula VII according to the invention, which consists of reacting, in a first step, an oxide group of the general formula VII bis:

$$\text{R'} \underset{X'}{\overset{CH_2Y'}{\bigcirc}} OR \quad \text{(VII bis)}$$

in which:
R and R' are such as defined above;
X' represents an —NHR₂ or hydroxy group;
Y' represents a hydrogen atom, a hydroxy group or —NHR'₂
R₂ and R'₂, identical or different, represent independently of one another a hydrogen atom, an alkyl group from 1 to 6 carbon atoms, an aralkyl from 7 to 12 carbon atoms, aryl from 4 to 10 carbon atoms, cycloalkyl from 3 to 6 carbon atoms, the aryl and aralkyl groups being optionally substituted by one or several, particularly up to 3, halogen atoms, groups NO₂, NH₂, CF₃ or alkoxy groups from 1 to 4 carbon atoms, and in which one at least of the groups X' and Y' represents —NHR₂ or NHR'₂
On a 2-halogeno-ethyl isocyanate to convert the —NHR₂ or NHR'₂ group of the compound of Formula VII bis respectively into $$NR_2\underset{\parallel}{C}NHCH_2CH_2Hal \text{ or } NR'_2\underset{\parallel}{C}NHCH_2CH_2Hal,$$
$$O \qquad\qquad O$$

Hal being a halogen atom, particularly chlorine, and in a second step to subject the compound obtained at the end of the preceding step to nitrosation, by means of an alcali metal nitrite, preferably sodium nitrite to convert the groups $$-NR_2\underset{\parallel}{C}NHCH_2CH_2Hal \text{ or } -NR'_2\underset{\parallel}{C}NHCH_2CH_2Hal$$
$$O \qquad\qquad O$$

respectively into $$-NR_2\underset{\underset{ONO}{\parallel\;|}}{C}NCH_2CH_2Hal \text{ or } NR'_2\underset{\underset{ONO}{\parallel\;|}}{C}NCH_2CH_2Hal.$$

To prepare the compounds of formula (Ibis), which enter into the preparation of the compounds according to the invention, it is possible to resort to one of the processes described below.

I

PREPARATION OF THE COMPOUNDS OF FORMULA

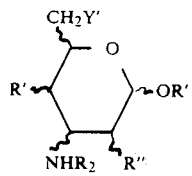

IA: First modification
The compounds of formula:

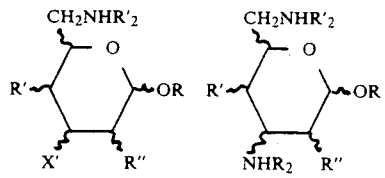

IA: First modification
The compounds of formula:

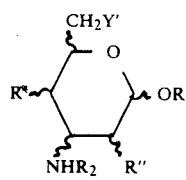

R, R', R", R₂ and Y' having the previously indicated meanings, which enter into the preparation of the compounds of formula:

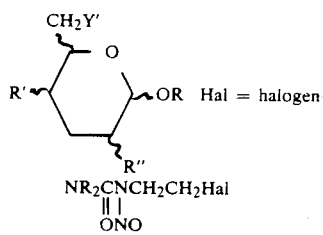 Hal = halogen of the invention, can be obtained from the compounds of formula:

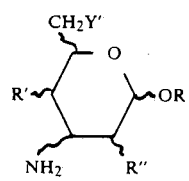

which are subjected:
in a first step to the action of an aldehyde

to convert the amine into an imine;
in a second step, to the action of a reducing agent, such as a hydride, for example sodium borohydride or sodium cyanoborohydride, to convert the imine into a secondary amine.

The process which has just been described can also be applied to the obtaining of compounds of formula:

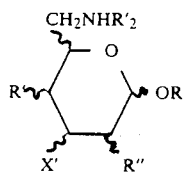

in which R, R', R", R'₂, X' have the above indicated meanings; and to obtaining compounds of formula:

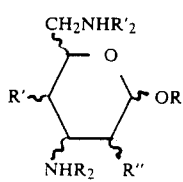

and in which R₂=R'₂.

In the latter case, the amounts of aldehyde and reducing agent employed are doubled.

IB: Second modification
The compounds of formula:

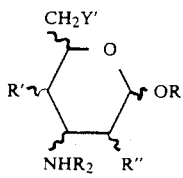

R, R', R", Y' and R₂ having the previously indicated meanings which enter into the preparation of the compounds according to the invention of formula:

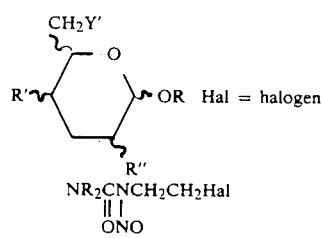 Hal = halogen can also be prepared from the compounds of formula:

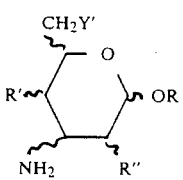

which are subjected to the action of an alkyl halogenoformate, of formula

particularly an alkyul chloroformate to give the compounds of formula:

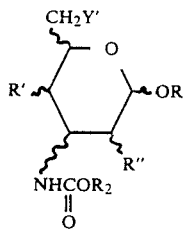

these compounds being then subjected to a reducing agent, for example aluminum and lithium hydride, to convert the

group into NHR$_2$.

This process can also be applied to the obtaining of compounds of formula:

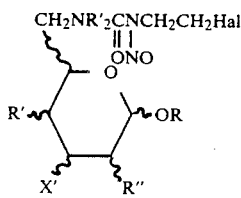

as well as to those of formula:

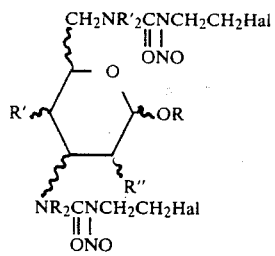

II

PREPARATION OF COMPOUNDS OF FORMULA

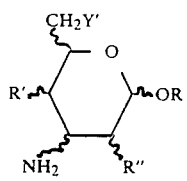

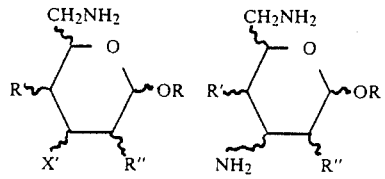

The compounds of formula:

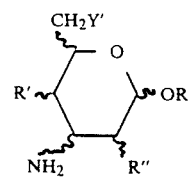

in which R, R' and R" have the above indicated meanings and Y' represents a hydroxy group can be obtained from compounds of formula:

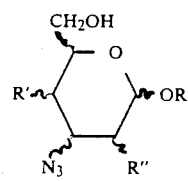

which are reduced, particularly by catalytic hydrogenation, for example hydrogenation in the presence of palladized carbon.

The compounds of the formula:

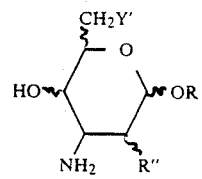

in which R and R" have the above indicated meanings and Y' represents a hydroxy group, can be obtained from compounds of formula:

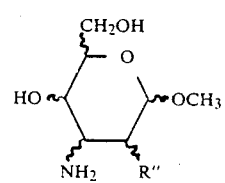

in which one of the hydrogen atoms or —NH$_2$ groups in the 3 position is protected, particularly by reacting the previously represented compounds with trifluoroacetic anhydride to give the compounds of formula:

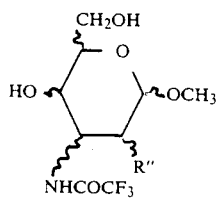

which are treated with an alcohol ROH, in an acid medium, to give the compounds of formula:

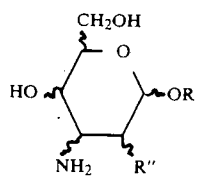

the protective group —COCF₃ being simultaneously hydrolized.

The compound of formula:

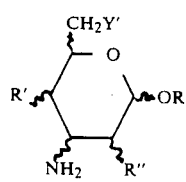

in which R, R' and R" have the above indicated meanings and Y' represents a hydrogen atom, can be obtained from compounds of formula:

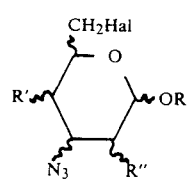

in which R, R' and R" have the above indicated meanings and Hal represents halogen, particularly bromine, these compounds being reduced, particularly by catalytic hydrogenation, for example in the presence of palladized carbon.

The compounds of formula:

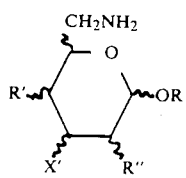

in which R, R' and R" have the above indicated meanings and X' represents a hydroxy group, can be obtained from the compounds of formula:

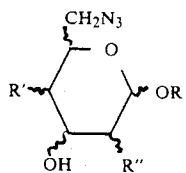

by reduction, particularly by catalytic hydrogenation, for example in the presence of palladized carbon.

Compounds of formula:

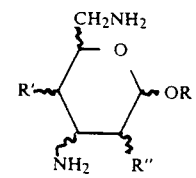

in which R, R' and R" have the above indicated meanings can be obtained from compounds of formula:

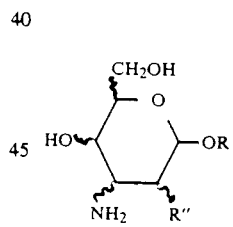

which are subjected to reduction, particularly catalytic hydrogenation, for example in the presence of palladized carbon.

III

PREPARATION OF COMPOUNDS OF FORMULA

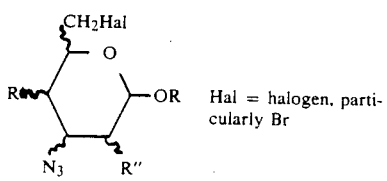

The compounds of formula:

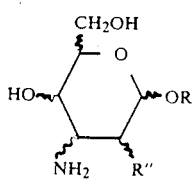

in which R, R' and R" have the above indicated meanings can be obtained from the compounds of formula:

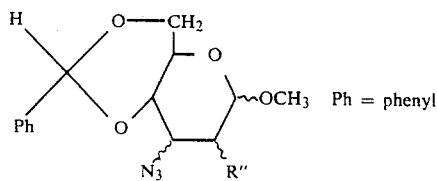 Ph = phenyl which are subjected to the action of acetyl chloride, then to neutralization with ammonia to give the compounds of formula:

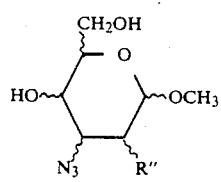

which are reduced, particularly by catalytic hydrogenation, for example in the presence of palladized carbon, to give the compounds of formula:

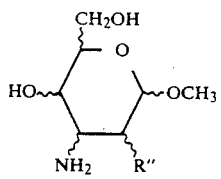

which can be converted by the action of an alcohol ROH, in an acid medium, into compounds of formula:

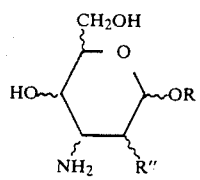

The compounds of formula:

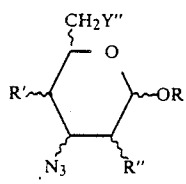

in which R, R' and R'' have the above indicated meanings and Y'' represents a halogen atom, particularly bromine, can be obtained from compounds of formula:

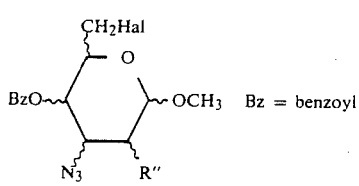 Bz = benzoyl which are subjected to an alcohol of formula ROH, in an acid medium to give the compounds of formula:

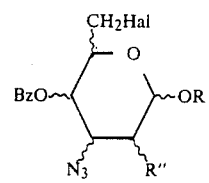

which are then converted into compounds of the formula:

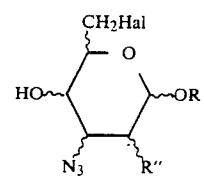

by removal of the benzoyl group, for example by means of a base, particularly an alkali alcoholate, such as sodium methylate.

The compounds obtained above can then be treated with an alkylating agent, such as $M_2SO_4$ or MX, X representing halogen, M representing an alkyl group from 1 to 30, preferably 1 to 12 carbon atoms, an aryl group of 6 to 12 carbon atoms, an aralkyl group from 7 to 12 carbon atoms, preferably 7 to 9 carbon atoms, the aryl and aralkyl groups being optionally substituted by one of several, particularly up to 3 halogen atoms, $NO_2$, $NH_2$, $CF_3$ groups or alkoxy from 1 to 4 carbon atoms, or representing an acyl group from 2 to 8 carbon atoms, preferably 2 or 3, or an aroyl group from 5 to 12, preferably 5 to 9 carbon atoms, unsubstituted or substituted by one or several, particularly up to 3 $NO_2$, $NH_2$, $CF_3$ groups halogen, alkoxy from 1 to 4 carbon atoms, in the presence of a base such as NaOH, to result in the compound of formula:

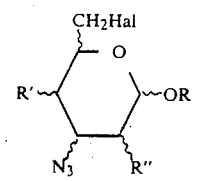

with R'=MO, M having the above indicated meaning.

IV

PREPARATION OF COMPOUNDS OF FORMULA

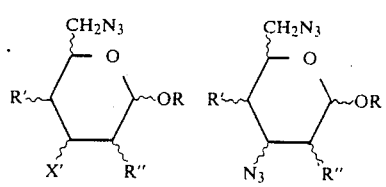

The compounds of the formula:

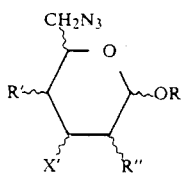

in which R, R' and R" have the above indicated meanings and X' represents an OH group, can be obtained from the compounds of formula:

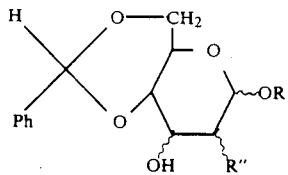

in which the OH functions at the 4 and 6 positions are protected, by causing the above described compounds to react, for example an acetic anhydride, in the presence of pyridine to protect the hydroxy group at the 3 position, to give the compounds of the formula:

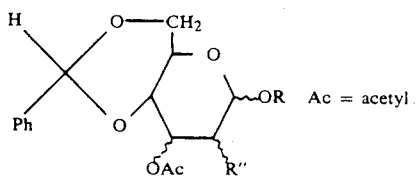

Ac = acetyl which, in the presence of N-halogeno succinimide, preferably N-bromosuccinimide, and barium carbonate give the compounds of formula:

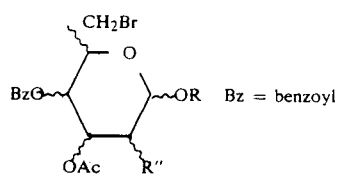

Bz = benzoyl which are subjected to an azotide, particularly an alkali metal azotide, such as sodium, in the presence of dimethylformamide, to give the compounds of the formula:

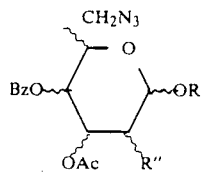

in which, in the presence of a base, particularly an alkali alcoholate, such as sodium methylate, give:

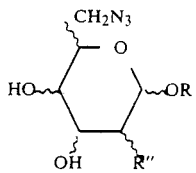

which can be subjected to $M_2SO_4$ or MX (X=halogen) in the presence of a base such as NaOH to give the compounds of the formula:

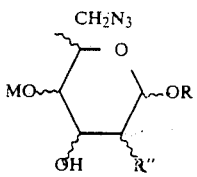

with MO=R', M having the above indicated meaning.

The compounds of formula:

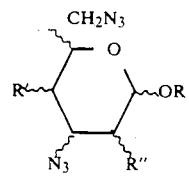

in which R, R' and R" have the above indicated meanings, can be obtained from the compounds of the formula:

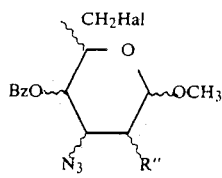

in which Hal represents a halogen atom, particularly bromine, which are subjected to the reaction of an azotide, particularly, of an alkali metal, such as sodium azotide, to give the compounds of formula:

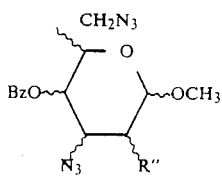

in which, the benzoyl group is removed, for example, by the addition of a base, particularly of an alkali alcoholate such as sodium methylate, to give the compounds of the formula:

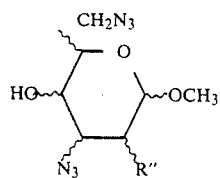

These compounds can be converted into compounds of the formula:

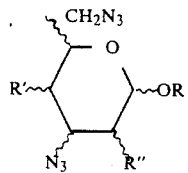

by protecting the hydroxy group at the 4 position, particularly by means of benzyl chloride to obtain compounds of formula:

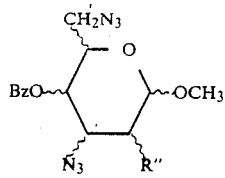

then by adding an alcohol of the formula ROH, in an acid medium, to obtain the compounds of the formula:

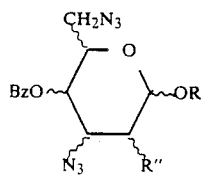

then by removing the protective group of the hydroxy function at the 4 position, particularly by means of a base, especially an alkali alcoholate such as sodium methylate, to obtain the compounds of the formula:

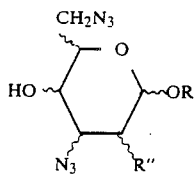

then by alkylating the above compounds, especially by means of $M_2SO_4$ or MX, X representing a halogen, M representing an alkyl group from 1 to 30, preferably 1 to 12 carbon atoms, an aryl group of 4 to 10 carbon atoms, an aralkyl group from 7 to 12 carbon atoms, preferably 7 to 9 carbon atoms, the aryl and aralkyl groups being optionally substituted by one or several, particularly up to 3 halogen atoms, $NO_2$, $NH_2$, $CF_3$ groups or alkoxy of 1 to 4 carbon atoms, or representing an acyl group of 2 to 8 carbon atoms, preferably 2 or 3, an aroyl group of 5 to 12, preferably 5 to 9 carbon atoms, unsubstituted or substituted by one or several, particularly up to 3 $NO_2$, $NH_2$, $CF_3$ groups, halogen, alkoxyde from 1 to 4 carbon atoms, in the presence of a base such as NaOH, to result in compounds of the formula:

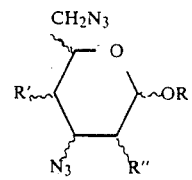

with R'=MO, M having the above indicated meaning.

The processes which have just been described above are advantageously applied to the preparation of the compounds usable for the synthesis of compounds of formula (VI) according to the invention.

More precisely, the process described in the paragraph I, enables the preparation of compounds of the formula:

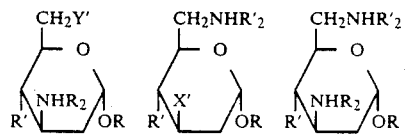

in which R, R', X', Y', $R_2$ and $R'_2$ have the above indicated meanings.

The process described in paragraph II enables the preparation of compounds of the formula:

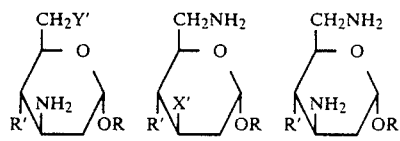

in which R, R' and Hal have the above indicated meanings.

The process described in paragraph III enables the synthesis of the compounds of the formula:

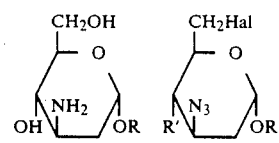

in which R, R'and Hal have the above indicated meanings.

The process described in paragraph IV enables the preparation of compounds of the formula:

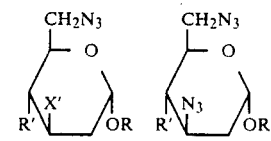

in which R, R', X' have the above indicated meanings.

According to a preferred embodiment of the process according to the invention, the compounds of the general formula (VIbis) are prepared, to obtain the compounds of formula (VI) according to the invention, by reacting an alpha-D-arabinohexopyranoside of the general formula (VIter) below:

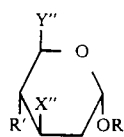
(VIter)

in which R and R' are as defined above, X" is an azide, hydroxy, NH₂ group or an alkylamine group, whose alkyl radical includes 1 to 6 carbon atoms, Y" can represent halogen, when X" represents an azide or hydroxy group, or Y" represents hydrogen, an azide group, an NH₂ group, hydroxy group or an NHR'₂ group where R'₂ is a hydrogen atom or an alkyl group from 1 to 6 carbon atoms, aralkyl from 7 to 12 carbon atoms, aryl from 4 to 10 carbon atoms, or cycloalkyl from 3 to 6 carbon atoms, the aryl and aralkyl groups being optionally substituted by one or several, particularly up to 3, halogen atoms, NO₂, NH₂, CF₃ groups or alkoxy groups from 1 to 4 carbon atoms, (a) either with an alcohol in an acid medium, in the case where X" is an azide group and Y" a halogen atom, hydrogen or hydroxy group or in a case where X" is a hydroxy group and Y" is an azide group, R is an alkyl group from 1 to 12 carbon atoms, aralkyl from 7 to 12 carbon atoms or halogenoalkyl from 1 to 12 carbon atoms and R' represents OM, M being an acyl group of 2 to 8 carbon atoms or arylester from 6 to 12 carbon atoms and where α-D-arabinohexopyranoside is deoxylated at 2,3,6-, the compound obtained then being reduced, particularly by catalytic hydrogenation, for example in the presence of palladized carbon to convert the azide group into NH₂, (b) or with an alkylating agent in the case where X" is an azide group, Y" is a halogen atom or hydrogen, R' is an OH group and R is an alkyl group from 1 to 12 carbon atoms or aralkyl from 7 to 12 carbon atoms and where α-D-arabinohexopyranoside is trideoxylated at 2,3,6-, the compound obtained being then reduced, particularly by catalytic hydrogenation, for example in the presence of palladized carbon, to convert the azide group into an NH₂ group, (c) or with trifluoroacetic anhydride, in the case where X" is an NH₂ group and Y" is a hydroxy group, a hydrogen atom or in the case where X" is a hydroxy group and Y" is an NH₂ group, R is an alkyl group from 1 to 12 carbon atoms or aralkyl from 7 to 12 carbon atoms and R' a hydroxy group, the trifluoro acetamide 3-α-D-arabinohexopyranoside obtained being treated with an alcohol in acid medium to obtain the 3-amino compound of the corresponding general formula and where α-D-arabinohexopyranoside is dideoxylated at 2,3, or trideoxylated at 2,3,6- ;

(d) or with an aldehyde in an alcoholic medium, in the case where X" is an NH₂ group, Y" is a hydrogen atom, an NH₂ group or NHR'₂ group or a hydroxy group or in a case where X" is a hydroxy group and Y" is NH₂ or NHR'₂ group and R and R' are as defined above, to obtain respectively the 3-desoxy 3-imino compound and/or the corresponding 6-desoxy 6-imino compound, which by reduction with a suitable reducing agent such as sodium borohydride or cyanoborohydride, gives the amine which then enables to obtain the α-arabinohexopyranoside 3-nitrosourea of the corresponding general formula VI, 2,3- or 2,6- dideoxylated or 2,3,6-trideoxylated.

To prepare the α-D-arabinohexopyranosides-nitrosoureas according to the invention, procedure is preferably as follows:

Modification (a) of the process:

To a solution of methyl 3-azido 4-O-acyl (or acylester) 6-bromo 2,3,6-tridesoxy α-D-arabinohexopyranoside, 0.01 mole, in 200 ml of hexane, are added 10 ml of alcohol (ethanol, benzyl or other alcohol) and 2 ml of paratoluenesulfonic acid.

The solution is heated to reflux for 12 to 48 hours. After cooling, the reaction medium is poured onto a saturated sodium bicarbonate solution, then extracted with ether. The organic phase is evaporated to dryness and gives a crude residue which is chromatographed on silica to give the ether of the general formula 1 corresponding to the alcohol.

Modification b of the process:

An alkyl-or aralkyl-3-azido-6-bromo-2,3,6-tridesoxy α-D-arabinohexopyranoside, and preferably methyl-3-azido-6-bromo 2,3,6-tridesoxy α-D-arabinohexopyranoside, 0.01 mole, are placed in solution in a suitable solvent such as anhydrous tetrahydrofuran (100 ml) or in another volvent such as dioxane, isopropyl ether, etc . . . 5–10 g of NaOH are added, then 5–10 g of an alkylating agent such as an alkyl sulfate, an alkyl halide, an aralkyl halide, for example. The suspension so-obtained is heated under reflux for 12 to 48 hours. After cooling and the slow addition of water, it is stirred at 20° for 2 hours. The organic phase is withdrawn by decantation, then the aqueous phase is again extracted with 100 ml of tetrahydrofuran. The organic phase, dried over sodium sulfate is evaporated to dryness. 60 to 90% of the desired compound are obtained, which is purified by chromatography on silica.

Modification (c) of the process:

Trifluoroacetic anhydride is reacted with methyl 3-amino 2,3,6-tridesoxy α-D-arabinohexopyranoside prepared by the method of J. BOIVIN et coll., Carb. Res. 85 (1980) 223–42 to obtain methyl-trifluoro 3-acetamido-α-D-arabinohexopyranoside (the methyl group being replaceable by another alkyl group or an aralkyl group, as defined above).

To a solution of 0.01 mole of the trifluoro-3-acetamido derivative so-obtained, in 200 ml of n-hexane, is added 5 to 20 ml of alcohol and 1 to 3 g of p-toluenesulfonic acid. By continuing the treatment as described in the first modification of the process, the ether of the general formula I corresponding to the alcohol is obtained, after having liberated the protected amine, by means of potassium carbonate, in an aqueous alcoholic medium.

Modification (d) of the process:

An aldehyde is reacted with the corresponding amine (Cf. 3rd modification of the process) as follows, to obtain the corresponding imine: a solution of 0.01 mole of aldehyde in ethanol or the methanol is added drop by drop, at ambiant temperature, to a solution of 0.01 mole of the amine which constitutes the starting compound of the third modification of the process, in anhydrous ethanol or methanol. The solution is heated under reflux for 2 to 12 hours. After cooling, there is added, in small portions, from 0.01 to 0.05 ml of a suitable reducing agent such as sodium borohydride or cyanoborohydride, and it is shaken for 12 hours. After evaporation of the solvent, the residue is taken up again in 20 ml of water, the precipitate is drained, then dried under vacuum under P₂O₅. The secondary amine obtained is recrystallized in alcohols.

The process is the same in the case where the 3-amino group is replaced, in the starting compound, by a 3-hydroxy group, the amino being in the 6 position. In the case where the desired compound must include a substitution by a secondary amine not only at the 3- position but also at the 6- position, the amounts of aldehyde and reducing agent employed are doubled.

The four modifications of the process described above are illustrated by the diagrams below:

I - DIAGRAM OF THE MODIFICATION (a) OF THE PROCESS: ETHERIFICATION

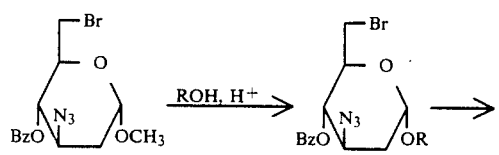

R = Ethyl, benzyl, etc . . .

II - DIAGRAM OF THE MODIFICATION (b) OF THE PROCESS

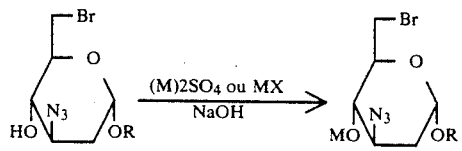

and (MO = R'
(R and M = methyl, ethyl, benzyl, etc.

III - DIAGRAM OF THE MODIFICATION (c) OF THE PROCESS WITH BLOCKING OF THE AMINE AT THE 3 POSITION

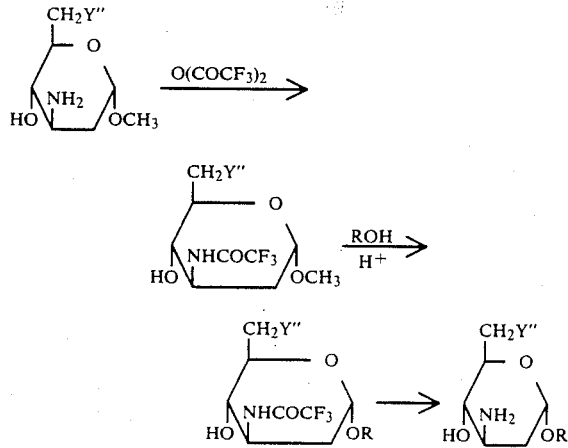

IV - DIAGRAM OF THE MODIFICATION (d) OF THE PROCESS

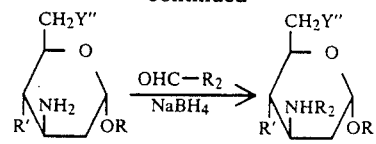

if Y = NH₂

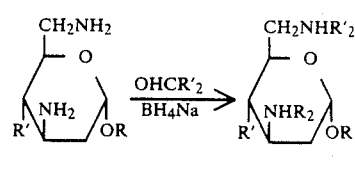

with R₂ = R'₂.

To prepare the alpha-L-arabinohexopyranosides-nitrosoureas according to the invention, of formula (VII):

 (VII)

and in which the nitroso group is on the 3 carbon, and R, R', X and Y have the above indicated meanings. Procedure is advantageously as follows.

The compounds of the following formula:

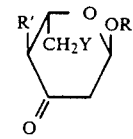

is treated with O-methylhydroxylamine hydrochloride and sodium acetate to obtain the compound of the following formula:

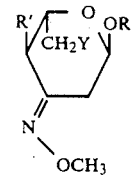

By treating the compound obtained previously by diborane and OH⁻ ions, the compound of formula:

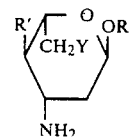

is obtained.

This compound is then treated with 2-chloro ethyl isocyanate, to give the compound of formula:

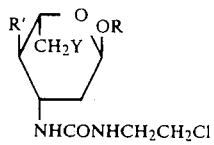

NHCONHCH₂CH₂Cl

This compound is then dissolved, for example in formic acid, then treated with sodium nitrite, to give the compounds of the formula:

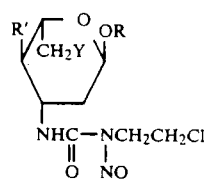

To prepare the alpha-D-xylohexopyranosidesnitrosoureas of the invention of formula (III), particularly those including a nitrosourea group in 3 position, in particular the compound of the following formula:

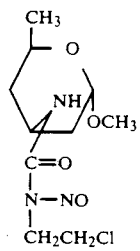

it is possible to use the compound of the following formula:

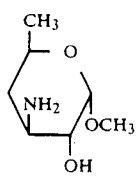

which in a first step, is treated with 2-chloro ethyl isocyanate, to give the corresponding urea, that is to say methyl 3-[3-(2-chloro ethyl) ureido]-3,4,6-tridesoxy alpha-D-xylohexopyranoside of the formula:

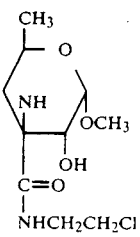

The compound indicated above, by treatment with sodium nitride is formic acid results in the corresponding nitrosourea, that is to say methyl 3-[3-(2-chloro ethyl) 3-nitroso ureido]3,4,6-tridesoxy alpha-D-xylohexopyranoside of the formula:

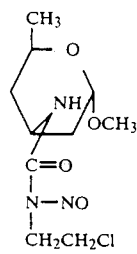

Except as described below, all the compounds which can be used in the preparation of the compounds of the formula (I), particularly of formula(VI), can be prepared by applying one or other of the reaction sequences described above, as well as suitable reaction sequences described in the examples given below, by way of illustration.

The 2-desoxy and 4-desoxy sugar derivatives of nitrosoureas of formula (I), described above exhibit useful therapeutic properties, notably anti-tumor properties. These nitrosourea derivatives can be made from the corresponding oside compounds of formula (Ibis) which can, in turn, be made from the corresponding primary amines. In this regard, a 2-desoxy compound of formula (I) of D-configuration can be made from the corresponding primary amine which can be made from a corresponding azide comprising the 2-desoxy function with a hydrogen in position 2. Likewise, a 2-desoxy compound of β-L-configuration of formula (I) can be made from the corresponding primary amine made from a corresponding azide comprising the 2-desoxy function with a hydrogen in position 2.

The 4-desoxy compounds of formula (I) in which Y represents hydrogen can also be made by equivalent processes starting either from a corresponding azide comprising the 4-desoxy function with a hydrogen in position 4, for example, for the 4-desoxy compounds of β-L-configuration, or from an intermediary compound comprising a primary amine group, for example, for the 4-desoxy compound of α-D-configuration.

However, some nitrosoureas compounds of formula (I) or the intermediates, from which they are made, must be made in other ways than have been described above. This is particularly the case for the compounds of formula(I) in which R' represents hydrogen and Y represents hydroxy and which are to be made from the corresponding primary amines or from corresponding azides with a 4-desoxy function and hydrogen in position 4. As a result, certain 4-desoxy compounds of formula (I) with a D-configuration are a special class of new nitrosourea derivatives. Surprisingly, some members of this special class of 4-desoxy compounds have high levels of anti-tumor activities that have never been reached in pharmacological tests which are considered as particularly significant today. In addition, a new process hereinafter described provides means for making additional new 4-desoxy compounds, particularly 4-halogen and/or 6-acyl, 4-desoxy compounds which also possess remarkably high levels of anti-tumor activity.

These new 4-desoxy nitrosourea derivatives are characterized in that they correspond to compounds with the formula IA below:

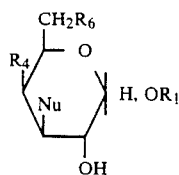 IA in the form of one of the two anomers, α or β, in which:
R₁ represents an alkyl group of 1 to 12 carbon atoms, or an aralkyl group of 7 to 12, preferably 7 to 9, carbon atoms, possibly substituted in the aromatic nucleus by 1 or more, in particular up to 3, halogen atoms, by 1 to 3 NO₂ or CF₃ groups or alkoxy groups containing 1 to 4 carbon atoms,
R₄ represents H or Hal, Hal being a Cl or Br atom, especially Cl,
R₆ represents OH or

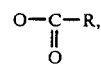

R corresponding to an alkyl group of 1 to 6 carbon atoms, an aryl group, unsubstituted or substituted on the aromatic nucleus by 1 or more atoms, in particular up to 3 halogen atoms, by 1 to 3 NO₂ or CF₃ groups or alkoxy groups of 1 to 4 carbon atoms.
Nu represents the group

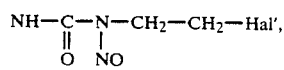

Hal' corresponding to a halogen chosen from among F, Cl, Br and I, identical with, or different from Hal and being in particular chlorine.

In formula IA and some of the formulae presented later the bond between the hydrogen atom or OR₁ group at position 1 of the sugar ring is represented by the symbol |H,OR₁.

This representation signifies that the OR₁ group can be either in the α position or in the β position according to the HAYWORTH representation.

In the remainder of the description the term alkyl includes linear, branched or cyclic (cycloalkyl) alkyl groups.

The substances according to the invention represented by formula IA are 3,4-dideoxy-α-D-xylohexopyranosides, 3,4-dideoxy-β-D-xylohexopyranosides, 3,4-dideoxy-α-D-galactohexopyranosides and 3,4-dideoxy-β-D-galactohexopyranosides.

An advantageous class of compounds according to the invention is constituted by the nitrosourea derivatives corresponding to the formula IA above and in which:
R₁ represents an alkyl group of 1 to 12 carbon atoms,
R₄ represents a halogen atom,
R₆ represents an OH or

R having the meanings indicated above.

In this class of nitrosourea derivatives according to the invention particularly advantageous compounds of formula IA indicated above are those in which:
R₁ represents a CH₃ group,
R₄ represents a halogen atom,
R₆ represents OH or

R having the meanings indicated above.

In this same class of nitrosourea derivatives according to the invention particularly advantageous substances of formula IA indicated above are those in which, on the one hand:
R₁ represents a CH₃ group,
R₄ represents Cl,
R₆ represents OH or

R having the meanings indicated above and, on the other:
R₁ represents a CH₃ group,
R₄ represents a halogen,
R₆ represents

R having the meanings indicated above.

Another advantageous class of nitrosourea derivatives according to the invention is constituted by those corresponding to formula IA indicated above in which:
R₁ represents a CH₃ group,
R₄ represents a hydrogen atom,
R₆ represents OH.

Another advantageous class of nitrosourea derivatives according to the invention is constituted by those corresponding to formula IA indicated above in which:
R₁ represents a CH₃ group,
R₄ represents a hydrogen atom,
R₆ represents

R having the meanings indicated above.

Among the compounds cited above, the most interesting are those having the following formulae:

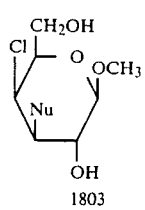 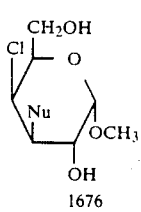
1803  1676

-continued

[Structure 1674: pyranose ring with CH$_2$OC$\phi$ (C=O), OCH$_3$, Nu, OH substituents]

1674

[Structure 1675: pyranose ring with CH$_2$OH, OCH$_3$, Nu, OH]

1675

[Structure 1677: pyranose ring with CH$_2$OH, OCH$_3$, Nu, OH]

1677

The present invention also relates to a procedure for the preparation of the new derivatives corresponding to formula IA

[Formula IA: pyranose ring with CH$_2$R$_6$, R$_4$, Nu, H,OR$_1$, OH]

IA in the form of one of the two anomers, α or β, in which:

R$_1$ represents an alkyl group of 1 to 12 carbon atoms, or an aralkyl group of 7 to 12, preferably 7 to 9, carbon atoms, possibly substituted by 1 or more, in particular up to 3, halogens atoms, by 1 to 3 NO$_2$ or CF$_3$ groups or alkoxy groups of 1 to 4 carbon atoms, R$_4$ represents hydrogen or Hal, Hal being a halogen atom, in particular Cl, R$_6$ represents OH or $$O-\underset{\underset{O}{\|}}{C}-R,$$

R having the meanings indicated above.
Nu represents the group $$NH-\underset{\underset{O}{\|}}{C}-\underset{\underset{NO}{|}}{N}-CH_2-CH_2-Hal',$$

Hal' being identical with, or different from Hal and representing a halogen atom, in particular chlorine, characterized in that (a) in a first series of reactions the compound represented by formula IIA

[Formula IIA: pyranose ring with CH$_2$OH, N$_3$, OH, OH, OH]

IIA is made to react in the form of a mixture of the α and β anomers with a glycosylating agent constituted by an alcohol R$_1$OH, R$_1$ having the meaning indicated above in order to convert the OH group in position 1 into the OR$_1$ group. The product thus obtained is treated with an activated derivative of the acid R—COOH in order to convert the OH group in position 6 into the $$O-\underset{\underset{O}{\|}}{C}-R$$

group, the α and β anomers are separated by a suitable method and each of the anomers, α or β, is made to react with a halogenating agent in order to introduce a halogen atom at position 4, the compound obtained being present as one of the anomers α or β and corresponds to the formula IIIA

[Formula IIIA: pyranose ring with CH$_2$O-C(=O)-R, Hal, N$_3$, H,OR$_1$, OH]

IIIA in which

R and R$_1$ have the meanings indicated in formula IA, Hal represents a halogen atom, (b) subsequently, in a second step, the compound represented by formula IIIA is subjected to a reduction in order to reduce N$_3$ to NH$_2$, this reduction being carried out, in addition, under conditions such that the halogen atom in position 4 may or may not be hydrogenolyzed, this reduction being possibly followed by hydrolysis of the $$O-\underset{\underset{O}{\|}}{C}-R$$

group in position 6 in order to generate an OH group. The compound obtained on completion of the second step is present in the form of one of the anomers α or β and corresponds to the formula IVA:

[Formula IVA: pyranose ring with CH$_2$R$_6$, R$_4$, NH$_2$, H,OR$_1$, OH]

IVA in which:

R$_1$, R$_4$ and R$_6$ have the meanings indicated in formula IA (c) in a third series of reactions the anomers, α or β, represented by formula IVA are subjected to reaction with an halogeno ethyl isocyanate in order to convert NH$_2$ into $$NHCNHCH_2CH_2Hal'$$
$$\|$$
$$O$$

and the product thus obtained is treated with the nitrite of an alkali metal, in particular sodium nitrite, in order to convert

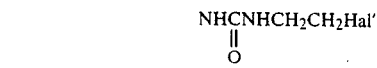

into

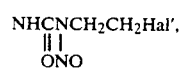

in order to obtain the compound represented by formula IA in the form of one of the two anomers, α or β.

In the formula IIA and some of the subsequent formulae the bond between the OH and the carbon atom at position 2 of the cyclic structure is represented by the symbol ⌇. This representation signifies that the OH group can be in either the α position or the β position.

As activated derivative of the acid R—COOH, use may be made of the acid derivatives used for the esterification of the primary hydroxyl groups, such as acid halide, preferably chloride, or anhydride.

As halogenating agent sulfuryl chloride or bromide is preferably used.

The starting material corresponds to formula IIA

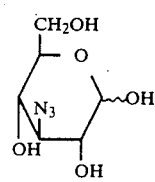

in the form of a mixture of the α and β anomers is described in the literature (particularly by Redlich in Liebigs Ann. Chem. 1981, p. 1215–1222).

A preferred embodiment of the procedure of the invention for the preparation of the nitrosourea derivatives corresponding to formula IA comprises:

the reaction of the compound corresponding to formula IIA above in the form of a mixture of the α and β anomers with a glycosylating agent constituted by R₁OH, R₁ having the meaning indicated above in order to lead to the formation of the compound corresponding to the formula VA:

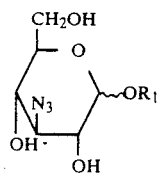

the introduction of an acyloxy group, of the formula

at position 6, R having the meaning indicated above in order to give rise to the compound with the formula VIA

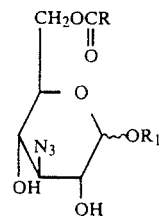

the separation of the compound VIA into the two anomers, α and β, corresponding to the formula VIIA

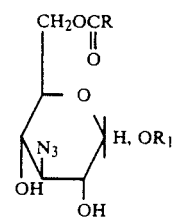

the reaction of the anomers, α or β, corresponding to formula VII, with a halogenating agent in order to give rise to the anomers α or β having the formula VIIIA

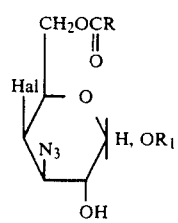

then:
either the reduction of the α or β anomer corresponding to formula VIIIA thus obtained under conditions such that N₃ is reduced to NH₂ without hydrogenolysis of the halogen atom at position 4 to give the α or β anomer corresponding to formula IXA

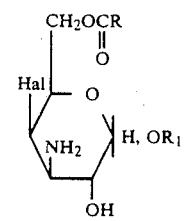

this reduction being:
either followed by the reaction of the α or β anomer corresponding to the formula IXA with an halogeno ethyl isocyanate in order to convert the NH₂ into

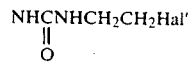

and the action of a nitrite of an alkali metal, in particular sodium nitrite, in order to convert $$\underset{\substack{\|\\O}}{NHCNHCH_2CH_2Hal'} \text{ into } \underset{\substack{\|\ |\\ONO}}{NHCNCH_2CH_2Hal'},$$

in order to obtain the compounds corresponding to formula IA in which $R_4$ represents a halogen atom and $R_6$ represents $$\underset{\substack{\|\\O}}{O-C-R},$$

or followed by the hydrolysis of the $$\underset{\substack{\|\\O}}{O-C-R}$$

group present at position 6 of the α or β anomer corresponding to formula IX and leading to the formation of an OH group, followed by the reaction of the α or β anomer corresponding to formula IXA with an halogeno ethyl isocyanate in order to convert the $NH_2$ into $$\underset{\substack{\|\\O}}{NHCNHCH_2CH_2Hal'}$$

and by the action of the nitrite of an alkali metal, in particular sodium nitrite, in order to convert $$\underset{\substack{\|\\O}}{NHCNHCH_2CH_2Hal'} \text{ into } \underset{\substack{\|\ |\\ONO}}{NHCNCH_2CH_2Hal'}$$

in order to give rise to the compounds of the formula IA in which: $R_4$ represents a halogen atom and $R_6$ represents OH, or the reduction of the anomers VIIIA under conditions such that the halogen atom at position 4 is replaced by H and the $N_3$ group is reduced to $NH_2$ to give rise to the α or β anomer corresponding to the formula XA

XA

[Structure: pyranose ring with $CH_2OCR$ (C=O) at top, O in ring, $NH_2$, H, $OR_1$, OH substituents]

this reduction being followed:
either by the reaction of the α or β anomer corresponding to formula XA with an halogeno ethyl isocyanate in order to convert the $NH_2$ into $$\underset{\substack{\|\\O}}{NHCNHCH_2CH_2Hal'}$$

and the action of the nitrite of an alkali metal, in particular sodium nitrite in order to convert $$\underset{\substack{\|\\O}}{NHCNHCH_2CH_2Hal'} \text{ into } \underset{\substack{\|\ |\\ONO}}{NHCNCH_2CH_2Hal'}$$

in order to produce the compounds corresponding to formula IA in which $R_4$ represents H, $R_6$ represents $$\underset{\substack{\|\\O}}{O-C-R}$$

or by the hydrolysis of the $$\underset{\substack{\|\\O}}{O-C-R}$$

group in position 6 of the α or β anomer corresponding to formula XA thus generating an OH group and leading to the formation of the α or β anomer corresponding to formula XIA

XIA

[Structure: pyranose ring with $CH_2OH$ at top, O in ring, $NH_2$, H, $OR_1$, OH substituents]

followed by the reaction of the α or β anomer corresponding to formula XIA with an halogeno ethyl isocyanate in order to convert the $NH_2$ into $$\underset{\substack{\|\\O}}{NHCNHCH_2CH_2Hal'}$$

and by the action of the nitrite of an alkali metal, in particular sodium nitrite, in order to convert $$\underset{\substack{\|\\O}}{NHCNHCH_2CH_2Hal'} \text{ into } \underset{\substack{\|\ |\\ONO}}{NHCNCH_2CH_2Hal'},$$

in order to produce the α or β anomer corresponding to formula IA in which $R_4$ represents H, and $R_6$ represents OH.

According to an attractive embodiment of the procedure of the invention for the preparation of derivatives corresponding to formula IA, the reduction of the compounds corresponding to formula IIIA such that $N_3$ is reduced to $NH_2$ and Hal is replaced by hydrogen is carried out by means of tributyl tin hydride in the presence of 2,2'-azo-bis-isobutyronitrile.

After the glycosylation of the compound corresponding to formula IIA the activated derivative of the acid RCOOH made to react with the compound corresponding to formula IIA in order to introduce a benzoyl group at position 6 is advantageously benzoyl chloride, used in the presence of bis tributyl tin oxide.

Another preferred embodiment of the procedure of the invention for the preparation of nitrosourea derivatives corresponding to formula $I_4$ in which $R_1$, $R_4$, $R_6$ and Nu have the meanings indicated above comprises:

the glycosylation of the compound corresponding to formula IIA in the form of the mixture of α and β anomers by means of CH₃OH in order to obtain the compound corresponding to formula XIIA:

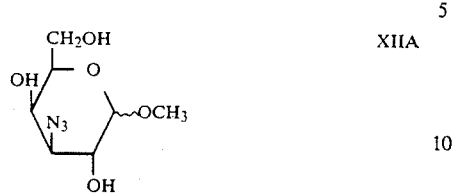

the reaction of the compound corresponding to formula XIIA thus obtained with benzoyl chloride in the presence of tributyl tin oxide in order to produce the compound corresponding to formula XIIIA:

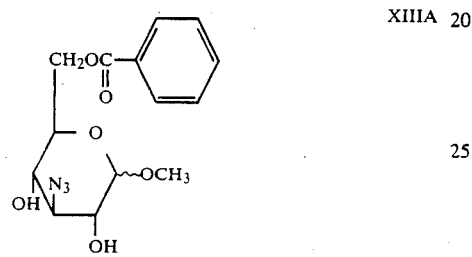

the separation of the two α and β anomers starting from the compound corresponding to formula XIIIA the reaction of either the α or β anomer with SO₂Cl₂ in order to obtain the α or β anomer corresponding to formula XIVA

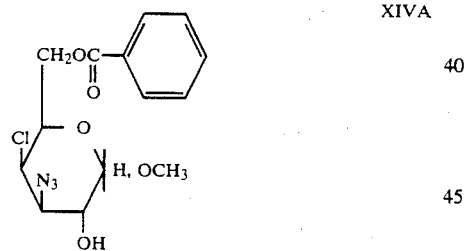

and
either the catalytic hydrogenation of the α or β anomer corresponding to formula XIA previously explained in order to give rise to the α or β anomer corresponding to formula XVA

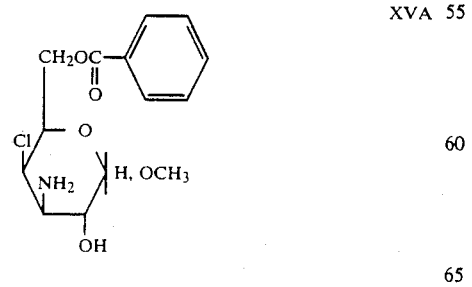

followed by
either the reaction of the α or β anomer corresponding to formula XVA with an halogeno ethyl isocyanate in order to convert the NH₂ into

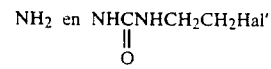

and by the action of the nitrite of an alkali metal, in particular sodium nitrite, in order to convert

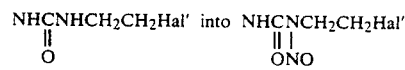

to give the α or β anomer corresponding to formula XVIA

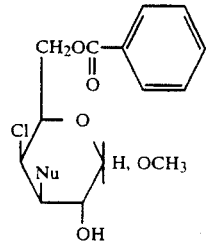

or by the reaction of the α or β anomer corresponding to formula XVA with a base, in particular an alkali alcoholate in order to hydrolyse the benzoyl group and generate the α or β anomer corresponding to formula XVIIA

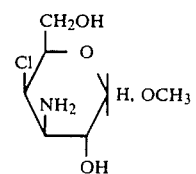

followed by the reaction of the α or β anomer corresponding to formula XVIIA with an halogeno ethyl isocyanate in order to convert the NH₂ into

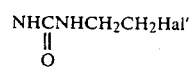

and by the action of the nitrite of an alkali metal, in particular sodium nitrite, in order to convert

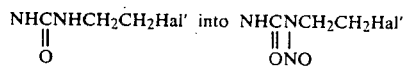

to give rise to the α or β anomer corresponding to the formula XVIIIA:

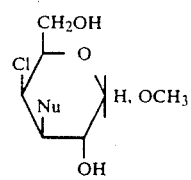

or the reduction of the α or β anomer corresponding to formula XIVA by means of tributyl tin hydride in the presence of 2,2'-azo-bis-isobutyronitrile to give the α or β anomer corresponding to the formula XIXA:

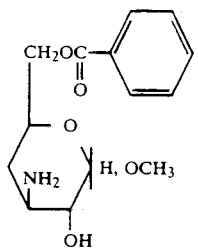

XIXA followed
either by the reaction of the α or β anomer corresponding to formula XIXA with an halogeno ethyl isocyanate in order to convert the NH₂ into

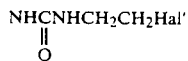

and by the action of the nitrite of an alkali metal, in particular sodium nitrite, in order to convert

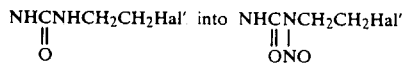

to give the α or β anomer corresponding to formula XXA:

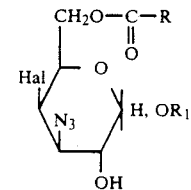

XXA or by the reaction of the alpha or beta anomer corresponding to formula XIXA with a base, in particular an alkali alcoholate, in order to hydrolyse the benzoyl group and generate the α or β anomers corresponding to formula XXIA:

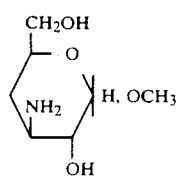

XXIA followed by the reaction of the α or β anomer corresponding to formula XXIA with an halogeno ethyl isocyanate in order to convert NH₂ into NHCNHCH₂CH₂Hal'
‖
O and by the action of the nitrite of an alkali metal, in particular sodium nitrite, in order to convert NHCNHCH₂CH₂Hal' into NHCNCH₂CH₂Hal'
‖                        ‖ |
O                        O NO to give the α or β anomer corresponding to formula XXIIA:

CH₂OH                                    XXIIA
 ⎡─O
 ⎣      H, OCH₃
 Nu
  OH

In carrying out the procedure according to the invention, the compounds corresponding to formula IIIA CH₂O—C—R                              IIIA
       ‖
       O
Hal
        H, OR₁
   N₃
   OH in which:
R₁ represents an alkyl group of 1 to 12 carbon atoms, or an aralkyl group of 7 to 12, and preferably 7 to 9, carbon atoms, possibly substituted on the aromatic nucleus by 1 or more, in particular, up to 3, halogen atoms, by 1 to 3 NO₂ or CF₃ groups or alkoxy groups of 1 to 4 carbon atoms.

R represents an alkyl group of 1 to 6 carbon atoms, an aryl group unsubstituted or substituted on the aromatic nucleus by 1 or more atoms, in particular up to 3 halogen atoms, NO₂ groups, CF₃ groups or alkoxy groups of 1 to 4 carbon atoms, Hal represents a halogen atom, in particular chlorine, are new, and exist in the form of either their α or β anomers.

Among the compounds corresponding to formula IIIA, a preferred group of substances is constituted by those corresponding to formula IIIA in which:
R₁ represents an alkyl group of 1 to 12 carbon atoms, R represents

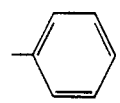

A particularly useful new compound corresponds to the following formula

IIIAa

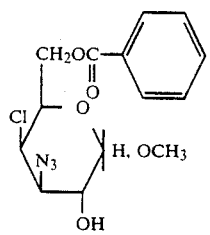

in the form of its α and β anomer.

The compounds corresponding to formula IIIA, in particular the two compounds corresponding to formula IIIAa (α anomer or β anomer), are key intermediates of the procedure and represent another feature of the present invention.

The examples which follow illustrate this invention and in no way limit it.

EXAMPLES

EXAMPLE 1

Preparation of benzyl 3-azido 4-O-benzoyl 6-bromo 2,3,6-tridesoxy α-D-arabinohexopyranoside by resorting to the first modification of the process To a solution of methyl 3-azido 4-O-benzyl 6-bromo 2,3,6-tridesoxy α-D-arabinohexopyranoside (1.5 g, 4.05 mmol.) in 125 ml of n-hexane, are added 10 ml of benzyl alcohol and 1 g of p-toluenesulfonic acid. The suspension is heated to reflux for 20 hours with azeotropic removal of the methanol released.

After cooling, the reaction medium is poured into a saturated solution of sodium bicarbonate then extracted with ether. The excess benzyl alcohol is then removed by azeotropic extraction with water, then with toluene. The crude residue so-obtained (1.8 g) is chromatographed on silica H with the mixture hexane/methylene chloride, 2:1 as eluant.

1.5 g of benzyl 3-azido 4-O-benzyl 6-bromo 2,3,6-tridesoxy α-D-arabinohexopyranoside (84%) are isolated.

MP: 77° C. (hexane)—$[\alpha]_D^{20}$: +20° (c:1%; CHCl$_3$).

IR$_{nujol}$: $\nu$2100 cm$^{-1}$ (N$_3$); $\nu$ 1760, 1260, 1030 cm$^{-1}$ (ester); $\nu$ 1600, 1585 cm$^{-1}$ (aromatic).

In the same manner there is prepared, for example:
Ethyl 3-azido 4-O-benzoyl 6-bromo 2,3,6-tridesoxy α-D-arabinohexopyranoside.
p-chlorobenzyl 3-azido 4-O-benzoyl 6-bromo 2,3,6-tridesoxy α-D-arabinohexopyranoside.

EXAMPLE 2

Use of the second modification of the process

The following compounds given by way of example, are prepared by alkylation of an alkyl or aralkyl-3-azido-6-bromo, 2,3,6-tridesoxy α-D-arabinohexopyranoside.
methyl 3-azido 6-bromo 2,3,6-tridesoxy 4-O-ethyl α-D-arabinohexopyranoside
methyl 3-azido 6-bromo 2,3,6-tridesoxy 4-O-benzyl α-D-arabinohexopyranoside
ethyl 3-azido 6-bromo 2,3,6-tridesoxy 4-O-ethyl α-D-arabinohexopyranoside
ethyl 3-azido 6-bromo 2,3,6-tridesoxy 4-O-benzyl α-D-arabinohexopyranoside
benzyl 3-azido 6-bromo 2,3,6-tridesoxy 4-O-ethyl α-D-arabinohexopyranoside
benzyl 3-azido 6-bromo 2,3,6-tridesoxy 4-O-benzyl α-D-arabinohexopyranoside.

EXAMPLE 3

Use of the third modification of the process

To a solution of 300 mg (1.16 mmole) methyl 3-fluoroacetamido 2,3,6-tridesoxy α-D-arabinohexopyranoside in 100 ml of n-hexane, are added 5 ml of benzyl alcohol and 300 mg of dry p-toluene sulfonic acid, and the treatment is as described in Example 1.

After chromatography and crystallization in a hexane-acetone mixture, 100 mg (30%) of pure product are isolated.

MP: 165° C.—$[\alpha]$D: +66 (c: 0.5%, CHCl$_3$).

The amine is then liberated by the action of potassium carbonate in an aqueous methanol medium.

By proceeding in the manner which has just been described, the following compounds, given by way of example, are prepared:
benzyl 3-amino 2,3,6-tridesoxy α-D-arabinohexopyranoside
ethyl 3-amino 2,3,6-tridesoxy α-D-arabinohexopyranoside
benzyl 3-amino 2,3-didesoxy α-D-arabinohexopyranoside
ethyl 3-amino-2,3-didesoxy α-D-arabinohexopyranoside.

EXAMPLE 4

Use of the fourth modification of the process

By proceeding in accordance with the fourth modification of the process it is possible to prepare, among others, the following compounds, given by way of example:
methyl 3-ethylamino 2,3,6-tridesoxy α-D-arabinohexopyranoside
methyl 3-benzylamino 2,3,6-tridesoxy α-D-arabinohexopyranoside
methyl 3-ethylamino 2,3-didesoxy α-D-arabinohexopyranoside
methyl 3-benzylamino 2,3-didesoxy α-D-arabinohexopyranoside
benzyl 3-ethylamino 2,3,6-tridesoxy α-D-arabinohexopyranoside
benzyl 3-benzylamino 2,3,6-tirdesoxy α-D-arabinohexopyranoside
methyl 6-ethylamino 2,6-didesoxy α-D-arabinohexopyranoside
methyl 6-benzylamino 2,6-didesoxy α-D-arabinohexopyranoside
benzyl 6-ethylamino 2,6-didesoxy α-D-arabinohexopyranoside
benzyl 6-benzylamino 2,6-didesoxy α-D-arabinohexopyranoside.

By doubling the amount of aldehyde and of reducing agent employed, the following secondary amines substituted at the 3,6 positions are prepared:
methyl 3,6-diethylamino 2,3,6-tridesoxy α-D-arabinohexopyranoside
methyl 3,6-dibenzylamino 2,3,6-tridesoxy α-D-arabinohexopyranoside
benzyl 3,6-diethylamino 2,3,6-tridesoxy α-D-arabinohexopyranoside
benzyl 3,6-dibenzylamino 2,3,6-tridesoxy α-D-arabinohexopyranoside.

EXAMPLE 5

Methyl 3-[3-(2-chloro ethyl) ureido] 2,3,6-tridesoxy alpha-D-arabinohexopyranoside

Compound 1

To a solution of 0.8 g ($5 \times 10^{-3}$ mole) of methyl 3-amino 2,3,6-tridesoxy alpha-D-arabinohexopyranoside (prepared according to the method of J. Boivin et coll. Carb. Res. 85 (1980) 223–42) in 2 ml of anhydrous DMF are added, drop by drop, at 0° C. and with stirring, 0.4 ml ($5.10^{-3}$ mole) of 2-chloro ethyl isocyanate. After 5 hours stirring, the reaction mixture is evaporated to dryness under vacuum. The residue, after purification by chromatography on a silicate column, with $CHCl_3$: 95, MeOH: 5 eluant, gives a single spot product crystallizing in anhydrous ethyl ether. The crystals were drained and then dried. (0.8 g, yield 60%).

ANALYSIS $C_{10}H_{19}Cl\ N_2O_4$: 266.5 - Calculated % C:45.0, H: 7.1; N: 10.5-Found % C: 44.9, H: 7.0, N: 10.5. MP: 125°–127°

NMR Spectrum Solvent: DMSO.$d_6$: 1.14 (d $CH_3$-6' J=6 Hz), 1.46 (t(d) H-2'axJ=J'=12 Hz, J''=4 Hz) 1.90 (dd H-2'J=12 Hz, J'=4 Hz) 2.78 (t H-4' J=J'=9 Hz) 3.19 (s $OCH_3$) 3.28 (m $CH_2$-4) 3.42 (m H-5') 3.53 (m $CH_2$-5) 3.61 (m H-3') 4.58 (d H-1' J=3 Hz) 5.99 (d NH J=8 Hz) 6.14 (t NH J=J'=6 Hz).

EXAMPLE 6

Methyl 3-[3-(2-chloro ethyl) 3-nitroso ureido] 2,3,6-tridesoxy α-D-arabinohexopyranoside

Compound 2 (IC 81. 1183)

1.2 g ($4.5.10^{-3}$ mole) of methyl 3-[3-(2-chloro ethyl) ureido]2,3,6-tridesoxy α-D-arabinohexopyranoside were dissolved in 8 ml of formic acid. To the solution maintained at 0° C., were added in small portions and with stirring 2.5 g (0.036 mole) of sodium nitrite. After 30 minutes, 10 ml of water were added, the stirring was then maintained for one hour. The reaction mixture was poured onto 100 ml of ethyl acetate and then dried over sodium sulfate and evaporated to dryness under vacuum. After purification on a chromatograph column, with silicate support, an eluant $CHCl_3$: 9, MeOH: 1, colorless crystals were obtained (600 mg, Yield 45%).

ANALYSIS $C_{10}H_{18}Cl\ N_3O_5$: 295.71 - Calculated % C: 40.6, H: 6.1, N: 14.2 - Found % C: 40.9, H: 6.0, N: 13.9. MP: 100° C.

$[\alpha]_D^{20}$: +92.8° (c: 0.5% $CHCl_3$) — $[\alpha]_{365}^{20}$: 123.6° (c: 0.5% $CHCl_3$).

NMR Spectrum (DMSO, $d_6$) 1.15 (d $CH_3$-6' J=6 Hz) 1.78 to 1.94 (m $CH_2$-2') 3.04 (t H-4' J=J'=9 Hz) 3.25 (s $OCH_3$) 3.51 (m H-5') 3.60 (t $CH_2$-4 J=J'=6 Hz) 4.10 (m $CH_2$-5, H-3') 4.65 (d H-1' J=3 Hz) 8.48 (d NH J=9 Hz).

Mass Spectrum: (M+1):296.

EXAMPLE 7

Methyl 3-azido 2,3-didesoxy α-D-arabinohexopyranoside

Compound 3

To 7 g (0.024 mole) of methyl 3-azido 4,6-benzylidene 2,3-didesoxy-α-D-arabinohexopyranoside prepared according to RICHARDSON A.C., (Carbohyd. Res. 4 (1967), 422-428), in solution in 400 ml of anhydrous methanol is added drop by drop and with stirring, 8 ml of acetyl chloride. After 6 hours stirring at ambient temperature, the solution is neutralized by bubbling gaseous ammonia through it. After evaporation under reduced pressure, the residue is taken up again with acetone under reflux. The acetone solution is concentrated under reduced pressure. By the addition of hexane, and then by cooling, white crystals are obtained which are drained, washed with hexane, then dried under vacuum. 3.45 g (71%) is obtained.

ANALYSIS $C_7H_{13}N_3O_4$: 203.2.
MP: 123°-124° C.
$[\alpha]_D^{20}$: +183° (c: 1%, MeOH).
IR: OH 3340, 3280 $cm^{-1}$; $N_3$ 2100 $cm^{-1}$.

EXAMPLE 8

Methyl 3-amino 2,3-didesoxy α-D-arabinohexopyranoside

Compound 4

A solution of 5 (0.0225 mole) of methyl 3-azido 2,3-didesoxy α-D-arabinohexopyranoside in 10 ml of methanol is stirred 12 hours under a hydrogen atmosphere, in the presence of triethylamine (1 ml) and 10% palladized carbon (1 g). The catalyst is removed by filtration. The filtrate, evaporated to dryness under reduced pressure, gives 4.35 g of compound 4 in the form of a colorless oil.

This compound is crystallized in hydrochloride form.
ANALYSIS $C_7H_{15}NO_4$, HCl: 213.67
MP: 120° C (dec.) $[\alpha]_D^{20}$: +90° (c: 1%, $H_2O$).

EXAMPLE 9

Methyl 3-[3-(2-chloro ethyl) 3-nitroso ureido] 2,3-didesoxy α-D-arabinohexopyranoside

Compound 6 (IC 81.1184)

From compound 4, following the operational method already described, methyl 3-[3-(2-chloro ethyl)ureido] 2,3-didesoxy α-D-arabinohexopyranoside, 5 is obtained by the action of 2-chloro ethyl isocyanate.

ANALYSIS $C_{10}H_{19}ClN_2O_5$: 282 - Calculated % C: 42.5, H: 6.7, N: 9.9 Found % C; 42.3, H: 6.8, N: 10.0.
MP: 125° C. $[\alpha]_D^{20}$: +168° (c: 0.25%, $CHCl_3$).

Then by nitrosation with sodium nitrite, in formic acid, Compound 6 is obtained.

ANALYSIS $C_{10}H_{18}Cl\ N_3O_6$: 311.71 - Calculated %: C: 38.5, H 5.8, N 13.5 Found %: C: 38.4, H: 5.6, N: 13.6. MP: 118° C.

$[\alpha]_D^{20}$: +96.2° (c: 0.5%, $CHCl_3$) — $[\alpha]_{365}^{20}$: 118.0° (c: 0.5%, $CHCl_3$).

NMR Spectrum (DMSO.$d_6$): 1.82 (t(d) H-2'$_{ax}$J=J'=12 Hz, J'': 4 Hz) 1.88 (d(d) H-2'eqJ=12 Hz J'=4 Hz) 3.28 (s $OCH_3$) 3.434 (r H-4'J=J'=9 Hz) 3.35 to 3.53 (m H-5', H-3') 3.49 to 3.67 5ab $CH_2$-6' $J_{gem}$=12 Hz) 3.61 (t $CH_2$-4 J=J'=6 Hz) 4.10 (m $CH_2$-5) 4.73 (d H-1' J=4 Hz) 8.53 (d NH J=9 Hz).

Mass Spectrum (chemical ionization): m/e 312 ($Cl_{35}$, M+1, Basic peak) and m/e 314 ($Cl_{37}$, 30%); m/e 280 (M+1-32, 30%)

EXAMPLE 10

Methyl 3-azido 6-bromo 2,3,6-tridesoxy α-D-arabinohexopyranoside-Compound 7

10 g (0.026 mole) of methyl 3-azido 4-O-benzoyl 6-bromo 2,3,6-tridesoxy α-D-arabinohexopyranoside prepared according to Hanessian, J. Org. Chem. 34 (1969) 1045-1053, are dissolved in 100 ml of 1M methanolic sodium methanolate. After 4 hours stirring at 20° C., the solution is then neutralized by passage over Amberlite IRA 50 resin, form H+. The filtrate, evaporated to dryness under vacuum, is purified by chromatography on silica H-60 and gives 6 g (Yield 84%) of Compound 7.
ANALYSIS $C_7H_{12}BrN_3O_3$: 266.22.
$[\alpha]_D^{20}$: +124° (c: 1%, $CHCl_3$).
IR Spectrum: 3420–3440 cm$^{-1}$ (OH) 2100 cm$^{-1}$ ($N_3$).

EXAMPLE 11

Methyl 3-azido 6-bromo 2,3,6-tridesoxy 4-O-methyl α-D-arabinohexopyranoside

Compound 8

5.5 g (0.021 mole) of compound 7 are dissolved in 200 ml of anhydrous tetrahydrofuran. 20 g of soda are added and then 20 ml of methyl sulfate. The reaction mixture is brought to reflux for 24 hours. After cooling, 100 ml of water were added. The organic phase is drawn off by decantation then the aqueous phase is again extracted with 100 ml of tetrahydrofuran. The organic phase, dried over sodium sulfate, is evaporated to dryness. 5.7 g (Yield 98%) of compound 8 is obtained. It is purified by chromatography on silica H (eluant hexane-methylene chloride 1:1).
ANALYSIS $C_8H_{14}BrN_3O_3$: 280.25.
$[\alpha]_D^{20}$: +188° (c: 1%, $CHCl_3$).
IRSpectrum: $\nu N_3$ 2100 cm$^{-1}$

EXAMPLE 12

Methyl 3-amino 2,3,6-tridesoxy 4-O-methyl α-D-arabinohexopyranoside

Compound 9

5.15 g (0.018 mole) of compound 8 in solution in 100 ml of anhydrous ethanol and 3 ml of redistilled triethylamine are placed under hydrogenation in the presence of 2 g of palladium on carbon, at ordinary pressure, for 12 hours. After removal of the catalyst, the solution is passed over an IR 45 ion exchange resin, OH$^-$ form. The solution evaporated to dryness results in 3.5 g of crude product purified by chromatorgaphy on silica H, eluant $CH_2Cl_3$—MeOH 9:1
ANALYSIS $C_8H_{17}NO_3$: 175.22.
$[\alpha]_D^{20}$: +∩° (c: 1%, $CHCl_3$).

EXAMPLE 13

Methyl 3-[3-(2-chloro ethyl) 3-nitroso ureido] 2,3,6-tridesoxy-4-O-methyl alpha-D-arabinohexopyranoside

Compound 10 (IC 83 1373)

It is obtained by the usual method from compound 9.
ANALYSIS $C_{11}H_{20}ClN_3O_5$: 309.75 - Calculated % C: 42.6, H: 6.5, N: 13.6 - Found % C: 42.3, H: 6.2, H: 13.6.
Mp: 60° C.
$[\alpha]_D^{20}$: +68.8° (c: 0.5% $CHCl_3$)—$[\alpha]_{365}^{20}$: +113.0° (c: 0.5%, $CHCl_3$).
NMR Spectrum (DMSO-$d_6$): 1.19 (d $CH_3$ J=6 Hz), 1.87 (m $CH_2$-2') 3.01 (t H-4'J=J'=9 Hz) 3.25 (s $OCH_3$-1) 3.35 (s $OCH_3$-4) 3.53 (m H-5) 3.63 (t $CH_2$-4 J=J'=6 Hz) 3.61 (m $CH_2$-5) 4.18 (m H-3') 4.66 (d H-1'H=3 Hz) 8.73 (d NH J=9 Hz).
Mass Spectrum (chemical ionisation): m/e 310 ($Cl_{35}$,(M+1, Basic peak) and m/e 312 ($Cl_{37}$, 30%); m/e 278 (m+1-32, 90%) and m/e 280 (27%).

EXAMPLE 14

Methyl 3,6-diazido 4-O-benzyl 2,3,6-tridesoxy α-D-arabinohexopyranoside

Compound 11

6 g (0.092 mole) of sodium azotide were added to a solution of 6 g (0.016 mole) of methyl 3-azido 4-O-benzyl-6-bromo 2,3,6-tridesoxy α-D-arabinohexopyranoside in 50 ml of anhydrous dimethylformamide. The reaction medium is brought to 80° C. for 8 hours. After cooling and dilution with 150 ml of water, it is extracted several times with ethyl ether. The ether phase, after evaporation to dryness, under vacuum, gives a colorless oil: 5 g(98%).
ANALYSIS $C_{14}H_{16}N_6O_4$: 332.32.
$[\alpha]_D^{20}$: +51° (c: 2.2%, $CHCl_3$).
IR Spectrum: 3450 cm$^{-1}$ (OH) 2115 cm$^{-1}$ ($N_3$).

EXAMPLE 15

Methyl 3,6-diazido 2,3,6-tridesoxy α-D-arabinohexopyranoside

Compound 12

5 g (0.015 mole) of compound 11 were placed in solution in 50 ml of anhydrous methanol, then a molar solution of sodium methylate (50 ml) was added and it was stirred for 3 hours at ambient temperature. The solution was neutralized by filtration on Amberlite IR 50 H$^{30}$ resin, then evaporated to dryness under reduced pressure. A syrupy oil (3.4 g 100%) was obtained which was purified on a silica column H (Eluant $CH_2Cl_2$).
ANALYSIS $C_7H_{12}N_6O_3$.
$[\alpha]_D^{20}$: +128° (c: 1.6%, $CHCl_3$).
IR Spectrum$_{film}$: 3450 cm$^{-1}$ (OH) 2115 cm$^{-1}$ ($N_3$).

EXAMPLE 16

Methyl 3,6-diamino 2,3,6-trideoxy α-D-arabinohexoypyranoside

Compound 13

3 g (0.013 mole) of compound 12 in solution in 100 ml of ethanol with 1% triethylamine are hydrogenated at ordinary pressure for 12 hours in the presence of palladium on carbon as catalyst. After removal of the catalyst, the filtrate evaporated to dryness gives a syrupy residue (2.8 g). Chromatography on silica (eluant $CH_2Cl_2$, ammoniacal MeOH 80:20) enabled isolation of the pure product 13.
ANALYSIS $C_7H_{16}N_2O_3$: 176.25.
$[\alpha]_D^{20}$: +130° (c: 1.13%, MeOH).
IR Spectrum$_{film}$: 3700 cm$^{-1}$ (OH), 3360 cm$^{-1}$ (NH).

EXAMPLE 17

Methyl bis 3,6-[3-(2-chloro ethyl) 3-nitroso ureido] 2,3,6-tridesoxy α-D-arabinohexopyranoside.

Compound 14 (IC 83-1374)

It is obtained by the usual method from compound 13.
ANALYSIS $C_{13}H_{22}Cl_2N_6O_7$: 445.267 - Calculated % C: 35.1, H: 5.0, N: 18.9 -Found % C: 35.3, H: 5.1, N: 19.2. Mp: 102° C.
$[\alpha]_D^{20}$: −59.0° (c: 0.5%, $CHCl_3$)— $[\alpha]_{365}^{20}$: +74.0° (c: 0.5%, $CHCl_3$).
NMR Spectrum (DMSO-$d_6$): 1.84 (m $CH_2$-2') 3.15 (s $OCH_3$) 3.17 to 3.77 (m $CH_2$-6', H-3', H-4', H-5', 2$CH_2$-4)

4.06 (m 2CH$_2$-5) 4.66 (d H-1 J=3 Hz) 8.41 (t NH J=J'=6 Hz) 8.50 (d NH J=9 Hz).

Mass Spectrum: (M+1): 445 100% Basic peak 447$_{Cl37}$$^{Cl35}$ 449$_{Cl37}$$^{Cl37}$

EXAMPLE 18

Methyl 3-O-acetyl 4,6-O-benzylidene 2-desoxy α-D-arabinohexopyranoside

Compound 15

40 ml of redestilled acetic anhydride are added to 10 g (0.037 mole) of methyl 4,6-O-benzylidene 2-desoxy α-D-arabinohexopyranoside in solution in 50 ml of anhydrous pyridine. After 48 at 50° C., the reaction mixture is cooled then poured onto cracked ice, extracted 3 times with 100 ml of dichloramethane. The organic phase dried over sodium sulfate gave after evaporation, 11.5 g (99%) of a crystalline product that is purified by recrystallization in the hexane-acetone mixture.

MP: 125°–127° C.

[α]$_D^{20}$: 74° (c: 1% chloroform)

IR Spectrum$_{Nujol}$: 1728, 1240 cm$^{-1}$ (c=O ester).

EXAMPLE 19

Methyl 3-O-acetyl 4-O-benzoyl 6-bromo 2,6-didesoxy α-D-arabinohexopyranoside

Compound 16

7.13 g (0.04 mole) of barium carbonate and 3.23 g (0.020 mole) of N-bromo-succinimide were added to 5.12 g (0.02 mole) of compound 15 in solution in 200 ml of carbon tetrachloride, were added. The reaction was brought to reflux for 3 hours. After cooling and removal of the insoluble by filtration, the organic phase was washed with a saturated solution of sodium bicarbonate.

After evaporation, 6.4 g (98%) of a single spot oily product in t.l.c. are obtained.

[α]$_D^{20}$: +70 (c: 1.45%, CHCl$_3$).

IR Spectrum: 1730 cm$^{-1}$, 1240 cm$^{-1}$ (CO ester) 1600, 1585 cm$^{-1}$ (aromatic).

EXAMPLE 20

Methyl 3-O-acetyl 6-azido 4-O-benzoyl 2,6-didesoxy α-D-arabinohexopyranoside.

Compound 17

To a solution of 8 g (0.020 mole) of compound 16 in 50 ml of anhydrous dimethylformamide were added 8 g (0.12 mole) of sodium azotide. The reaction mixture was brought to 80° C. for 8 hours.

After cooling and dilution with water, the reaction mixture was extracted with ether. The solution washed several times with water, was dried over sodium sulfate. After evaporation under vacuum, the residue was purified by chromatography on silica (eluant hexane-ethyl acetate, 311). 6.5 g of pure product were isolated (95%). The product was recrystallized from hexane.

ANALYSIS C$_{16}$H$_{19}$N$_3$O$_5$: 349.38.

MP: 68° C.

[α]$_D^{20}$: +90 (c: 1%; CHCl$_3$).

IR: 2100 cm$^{-1}$ (azide) 1725, 1280, 1050 cm$^{-1}$ (ester) 1610, 1590 cm$^{-1}$ (aromatic).

EXAMPLE 21

Methyl 6-azido 2,6-didesoxy α-D-arabinohexopyranoside

Compound 18

A methanolic solution of sodium methylate (20 ml) was added to a solution of 4.96 g (0.014 mole) of compound 17 in 50 ml of anhydrous methanol.

After 12 hours stirring at room temperature, the reaction medium was neutralized by filtration on Amberlite IR 50 resin (form H+). After removal of the solvent, the syrupy residue obtained was chromatographed on a silica column to remove the methyl benzoate. 2.76 g of compound 18 were obtained (96%).

ANALYSIS: C$_7$H$_{13}$N$_3$O$_4$: 203.2

[α]$_D^{20}$: +ψ° (c: 1% chloroform).

IR Spectrum: 3400 cm$^{-1}$ (OH) 2120 cm$^{-1}$ (azide).

EXAMPLE 22

Methyl 6-amino 2-desoxy α-D-arabinohexopyranoside

Compound 19

A solution of 2.40 g (0.011 mole) of compound 18 in 25 ml of anhydrous ethanol was shaken under a hydrogen atmosphere in the presence of 10% palladium or carbon 500 mg) for 12 hours. After elimination of the catalyst, the evaporation of the filtrate led to an oil product 2 g (95%). A sample was converted into the picrate.

ANALYSIS: C$_{13}$H$_{18}$N$_4$O$_{11}$: 406.35.

MP: 156° C. (ethanol).

[α]$_D^{20}$: +75° (c: 1.2%, chloroform).

EXAMPLE 23

Methyl 3-[3(2-chloro ethyl) 3-nitroso ureido]2,6-didesoxy α-D-arabinohexopyranoside

Compound 20 (IC83 1350)

It is obtained by the usual method from compound 19.

ANALYSIS C$_{10}$H$_{18}$ClN$_3$O$_6$: 311.728 - Calculated %: C: 38.5, H: 5.8, N: 13.5 - Found %: C: 38.5, H: 5.5, N: 13.4.

MP: 101° C. (dec.): $D^{20}$: +26.2 (c: 0.5%, CHCl$_3$); 365$^{20}$: 51.0 (c: 0.5%, CHCl$_3$).

NMR Spectrum (CMSO-d$_6$): δ 1.45 (t(d) H-2'$_{ax}$J=J'=12 Hz, J''=4 Hz), 1.85 (d(d) H-2'$_{eq}$ J=12 Hz J'=4 Hz), 2.95 (t H-4' J=J'=9 Hz), 3.10 (s-OCH$_3$), 3.30 (m H-3'), 3.51 (m H-5+a CH$_2$-6'), 3.58 (t CH$_2$-4 J=J'=6 Hz), 3.75 (d$_b$CH$_2$-6' J$_{gem}$=12 Hz), 4.06 (m CH$_2$-5), 4.15 (d H-1'J=3 Hz), 4.81 (OH), 5.10 (OH), 8.50 (t NH).

Mass Spectrum: (M+1)=312 Cl$_{35}$ 314 Cl$_{37}$ (Loss of MeOH −32) 280.

EXAMPLE 24

Methyl N methoxycarbonyl 3-amino 2,3,6-tridesoxy α-D-arabinohexopyranoside

Compound 21

6 ml of methyl chloroformate were added at 0° C. and with stirring, in 10 minutes to 1.5 g (0.0093 mole) of methyl 3-amine 2,3,6-tridesoxy α-D-arabinohexopyranoside in 200 ml of anhydrous methylene chloride. The reaction mixture was kept 2 hours at ordinary temperature, then 100 ml of 4N soda were added. After one night with stirring, the organic phase was separated by decantation, the aqueous phase extracted with 100 ml of methylene chloride. The organic phase washed with distilled water was dried over sodium sulfate.

After evaporation under vacuum, the residue obtained was recrystallized in a methanol-methylene chloride mixture, 1.7 g (80%).

ANALYSIS C9H17NO5: 219.24.
MP: 180° C.
$[\alpha]_D^{20}$: +157 (c: 1%, CHCl3).

EXAMPLE 25

Methyl 3-methylamino, 2,3,6-tridesoxy α-D-arabinohexopyranoside

Compound 22

1.7 g (0.0077 mole) of compound 21 in 50 ml of anhydrous ethyl ether were added drop by drop, so as to maintain a slight reflux (30′) to 1 g of lithim and aluminum hydride in 100 ml of anhydrous ethyl ether. The reflux was continued for 6 hours. After cooling, the excess of hydride was decomposed by the very slow addition of 1 ml of water, then 1 ml of 3N soda, then 3 ml of water. The precipitate was removed by filtration. After evaporation under vacuum and then recrystallization in a mixture acetone-hexane the organic phase dried over sodium sulfate gave, 1.05 g of crystals (80%); MP: 105° C.

ANALYSIS C8H17NO5: 175.23.
$[\alpha]_D^{20}$: 89 (c: 1%, CHCl3).

EXAMPLE 26

Methyl 3-[3-(2-chloro ethyl) 1-methyl 3-nitroso ureido]2,3,6-tridesoxy α-D-arabinohexopyranoside Compound 23 (IC 83.1375)

It was prepared according to the usual method from compound 22.

The examples 5 to 25 above are illustrated by the following reaction diagrams:

Examples 5 and 6

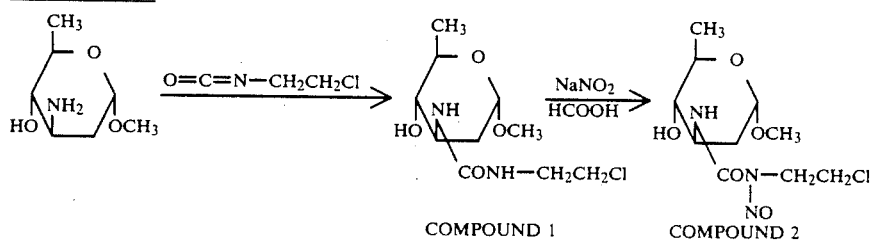

Examples 7 a 9

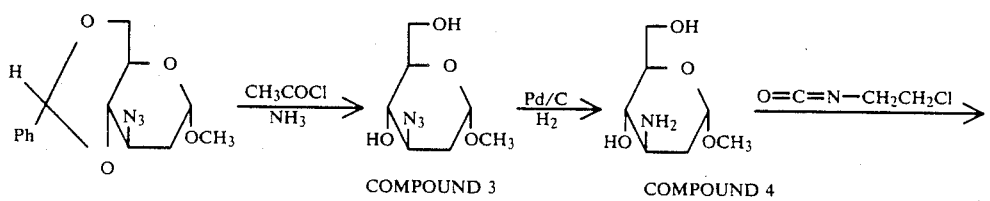

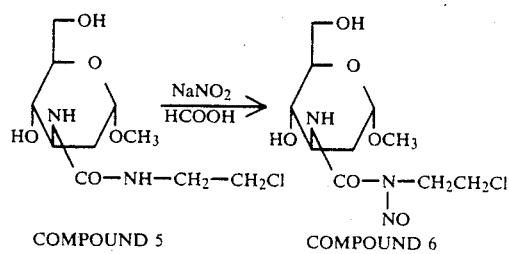

Examples 10 a 17

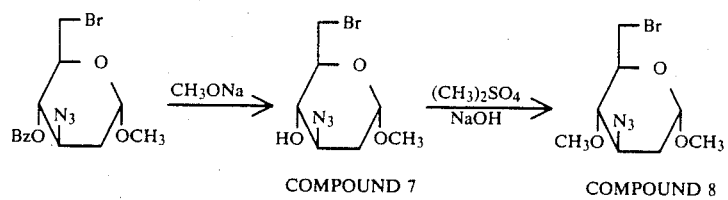

-continued
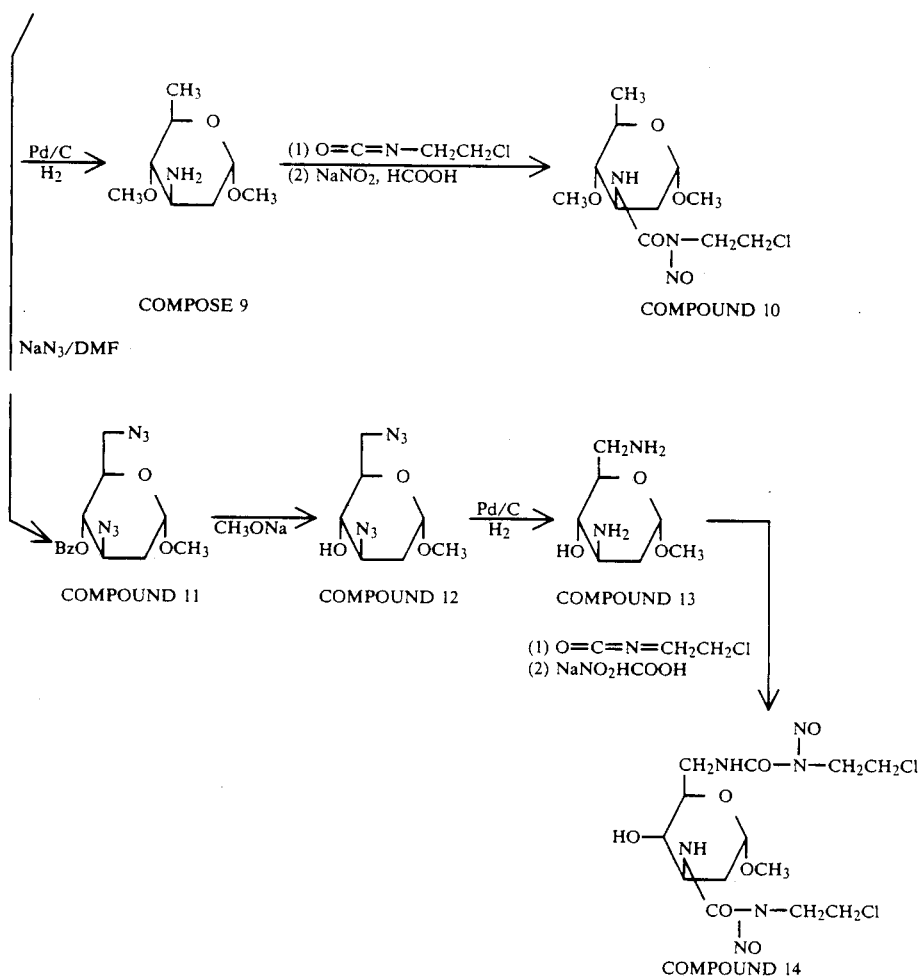
Examples 18 a 23
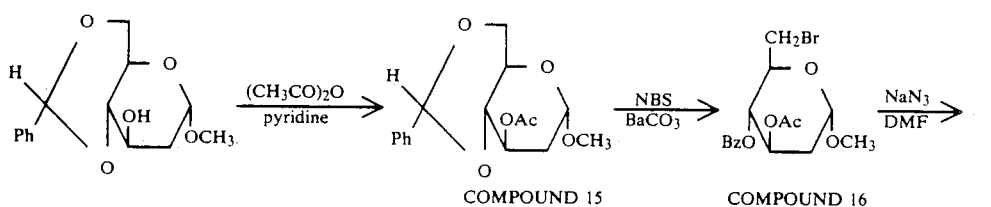
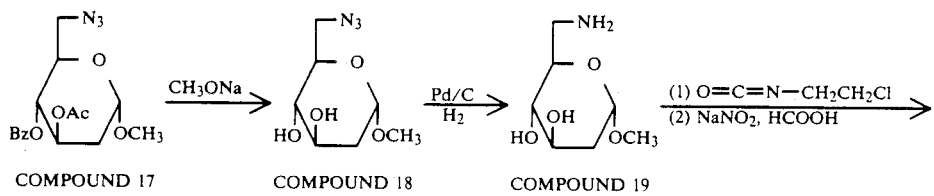
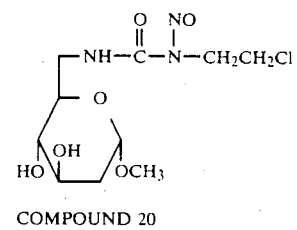
COMPOUND 20
Examples 24 a 26

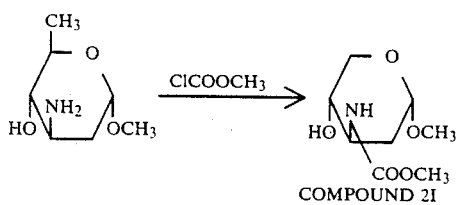 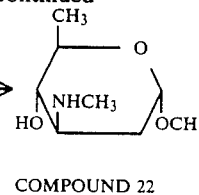

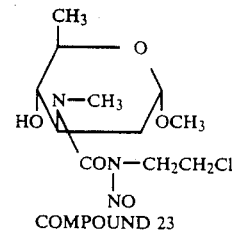

EXAMPLE 27

Methyl 3 [3-(2-chloro ethyl) 3-nitroso ureido]2,3,6-tridesoxy α-L-arabinohexopyranoside

Compound 26 - IC 841530

The preparation of methyl 3-amino 2,3,6-tridesoxy α-L-arabinohepoxyranoside (L-acosamine) is first carried out, as mentioned hereafter.

3.1 g (0.04 mole) of anhydrous sodium acetate and 2.1 g (0.024 mole) of 0-methyl hydroxylamine chlorhydrate are added to 1.92 g (0.012 mole) of methyl 2,6-didesoxy α-L-erythrohexopyranoside 3-ulose in 25 ml of 50% aqueous ethanol. The reaction medium is brought to reflux 3 hours, then ethanol is evaporated. After extraction with dichloromethane and drying over sodium sulfate sodium, a clear oil (2 g) is obtained, the structure of which is confirmed by NMR and corresponds to 0-methyloxime of L-acosamine.

This oil is solubilized in 20 ml of anhyrous tetrahydrofurane and 30 milliequivalents of diborane are added to the solution under nitrogen and at 0° C.

The reaction mixture is brought to reflux two hours, then cooled at 0° C., 5 ml of water, then 5 ml of 20% potash are added carefully. The reaction medium, brought to reflux 3 hours, then cooled, is extracted with ethyl acetate. The organic phase gives, after evaporation, a residue, which, after purification, gives L-acosamine crystals.

M.P. 130°-133° C.

$[\alpha]_D^{20}$: 140° C. (c: 6.6% MeOH).

The preparation of methyl 3-[3(2-chloro ethyl-)ureido]2,3,6-tridesoxy α-L-arabinohexopyranoside (compound 25) is carried out, as mentioned hereafter.

0.3 ml ($4.10^{-3}$ mole) of 2-chloro ethyl isocyante are added to a solution of 0.48 g ($3.10^{-3}$ mole) of methyl 3-amino 2,3,6-tridesoxy α-L-arabinohexopyranoside in 8 ml of redistillated dimethylformamide. After 2 hours of stirring, the reaction mixture is evaporated to dryness under vacuum. The crystals are dried, then washed with ether: 781 mg (98%).

NMR Spectrum: Solvent DMSO $D_6$: 1.14 (d, $CH_3$-6', J=6 Hz); 1.46 (T(d), H-2'$_{ox}$ J=J'=12 Hz, J"=4 Hz); 1.90 (dd, H-2'$_{eq}$ J=12 Hz, J'=4 Hz); 2.78 (T,H-4', J=J'=9 Hz); 3.19 (s, $OCH_3$); 3.28 (m, $CH_2$-4); 3.42 (m,H-5'); 3.53 (m,$CH_2$-5); 3.61 (m, H-3'); 4.58 (d,H-1', J=3 Hz); 5.99 (d,NH, J=8 Hz); 6.14 (t, NH, J=J'=6 Hz).

The final product which is desired (compound 26), i.e. methyl 3 [3-(2-chloroethyl)3-nitroso ureido] 2,3,6- tridesoxy 2,3,6 α-L-arabinohexopyranoside is obtained from the product which has been previously synthesized, as follows 0.66 g ($2.5 \times 10^{-3}$ mole) of [3(2-chloro ethyl) ureido] 2,3,6-tridesoxy α-L-arabinohexopyranoside are dissolved in 5 ml of formic acid. 1.4 (0.02 mole) of sodium nitride are added by small portions and under stirring to the solution which is kept at 0° C. After 30 minutes, 5 ml of water are added and the stirring is maintained for one hour. The reaction mixture is poured on to 100 ml of ethyl acetate then dried over sodium sulfate and evaporated to dryness under vacuum. After purification, on a silica support column, eluent $CH_2Cl_2$: 98, MeOH: 2 colorless crystals are obtained: 210 mg (30%) MP: 100° C.

ANALYSIS $C_{10}H_{18}ClN_3O_5$: 295.71. Calculated %: C: 40.6; H: 6.1; N: 14.2. Found %: C: 40.9; H: 6.1; N: 13.90.

NMR Spectrum (DMSO,$D_6$): 1.15 (d,$CH_3$-6' J=6 Hz); 1.78 a 1.94 (m, $CH_2$-2'); 3.04 (t,H-4', J=9 Hz); 3.25 (s,$OCH_3$); 3.51 (m,H-5'); 3.60 (T,$CH_2$-4, J=J'=6 Hz); 4.10 (m,$CH_2$-5, H-3'); 4.65 (d,H-1',J=3 Hz); 8.48 (d,NH, J=9 Hz).

The reaction diagram hereafter summarizes the steps which have just been described:

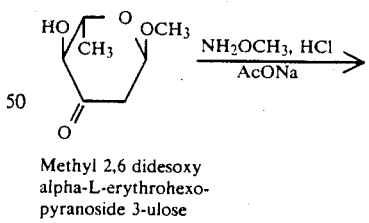

Methyl 2,6 didesoxy alpha-L-erythrohexopyranoside 3-ulose

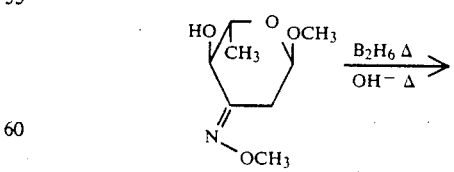

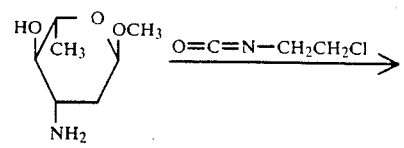

Compound 24

-continued

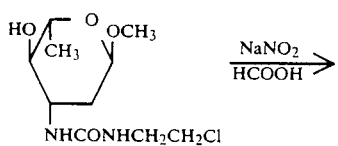

Compound 25

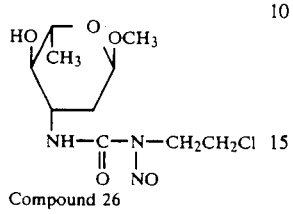

Compound 26

PHARMACOLOGICAL STUDY

In order to test the antitumoral activity of the compounds of formula I in the first place leucemia murin L1210 was used. Among murin leucemias, leucemia L1210 is resistant and selective. A substance having a great activity on leucemia L1210 presents a potential of activity in the clinical field of humans (J. M. Venditti, Relevance of transplantable animal tumor systems to the selection of new agents for clinical trial in pharmacological basis of cancer chemotherapy, the University of Texas ed Williams and Wilkins Co. publ. 1975, Baltimore USA, p. 245–270).

Besides, the experimental tumor, leucemia L1210 of the mouse is in fact currently used for the evaluation of all antitumoral compounds at present used in human therapy, as described, for example by C. C. Zubrod in Proc. Nat. Acad. Sci. USA, 69, 1972, p. 1 042–1 047. The tumoral system so-constituted experimentally enables very accurate experimental evaluation of the activity of the compound tested and, consequently also, an objective comparison between the respective activities of the different compounds, for example according to the methods described by R. E. Skipper, F. W. Schapel Jr. and W. S. Wilcox in Cancer Chemother, Rep., 35, 1964, p. 1–111 and 45, 1965, p. 5–28.

This has been confirmed by the results of recent work of Staquet et al. Cancer Treatment Reports, vol. 67, No. 9, September, 83.

In practice, the biological effects of the novel nitrosourea derivatives according to the present invention have been tested as follows.

METHOD

The test used is that of W. J. Durkin et al. Cancer Research 1979, 39, 402–407, modified.

All the nitrosoureas were dissolved in 70% ethanol in the proportion of 10 mg/ml.

The testing was carried out in two steps.

1. Determination of the 20% cytotoxic index

100 μl of an L 1210 cell suspension ($10^6$ cells per ml) in R P M I 1640 culture medium supplemented with 10% of fetal calf serum and 40 μg/ml of gentamycin, containint various doses of the products to be tested (0 to 100 μg/ml) were incubated 24 hours at 37° C. At the end of this time, the cell viability is determined by the trypan blue exclusion test. The cytotoxic index is defined by the formula:

$$\text{Cytotoxic index: } 100 \left[ 1 - \frac{\% \text{ treated living cells}}{\% \text{ control living cells}} \right]$$

The amount of ethanol is the same in the cultures containing the products to be tested and in the control cultures (this amount has no effect either on growth nor on cell viability).

For each product the dose which gives a cytotoxic index of 20% is determined.

2. Determination of the potential "in vivo" activity

L 1210 cells, under conditions similar to the preceding protocol, were contracted for 1 hour with a dose of the various products tested corresponding to a cytotoxic index equal to 20%. After this time, the cells were placed in culture medium not containing nitrosoureas and incubated at 37° C. After 48 hours, the cytotoxic index was determined.

W. J. DURKIN et al. . . . showed that, under these conditions, if the cytotoxic index was equal to or greater than 40%, the product concerned would be active "in vivo" in the mouse.

RESULTS

The results are collected in the following table I.

TABLE I

| PRODUCT TESTED | | TEST No 1 DOSE CORRESPONDING TO A 20% CYTOTOXIC INDEX μg/ml | TEST No 2 CYTOTOXIC INDEX % | POTENTIAL "IN VIVO" ACTION | "IN VIVO" ACTIVITY |
|---|---|---|---|---|---|
| COMP. 2 | IC 1183 | 50 | 77 | + | + |
| COMP. 6 | IC 1184 | 20 a 25 | N.D. | | N.D. |
| COMP. 10 | IC 1373 | 80 | 68 | + | N.D. |
| COMP. 14 | IC 1374 | 50 | 71 | + | N.D. |
| COMP. 20 | IC 1350 | N.S. | N.S. | − | |
| COMP. 23 | IC 1375 | 60 | 69 | + | N.D. |

N.D. = undetermined
N.S. = not significant

3. Determination of the effective "in vivo" activity in the mouse

The experimentation which is reported below used the compound 2 prepared according to the above example 6 (Ref. IC 81 1183).

3.1 Protocol

The mice (female, average weight 20g) used were $F_1/DBA_2/C_{57}/B_1$ (Animal selction and breeding center of the Laboratories of the CNRS, Orleans, La Source).

The mice distributed in cages by drawing lots were inoculated on day "0" with $10^5$ leucemia L1210 cells.

The animals were treated with the compound IC 81 1183 intraperitoneally on days 1, 5 and 9.

The suspensions were prepared just before the injection:product 2+neutralized and sterilized olive oil.

The mortality of the animals was observed regularly, the relative increase in the survival (T/C×100) was calculated from the average survival of the treated animals (T) and that of the control animals (C).

The doses used are in mg/kg of mouse:1.25, 2.5, 5, 10, 20, 40, 50, 60, 80.

3.2. Results 1.25 mg→T/C=118
2.50 mg→T/C=158
5 mg→T/C=170
10 mg→T/C=220
20 mg→T/C=∞
40 mg→T/C=∞
50 mg→T/C=100
≧60 mg→Toxicity 3.3. Remarks (a) T/C=∞:for definition: more than 50% of the treated animals were finally cured; now in the experiments carried, all the animals at doses of 20 and 40 mg/kg were cured finally.

(b) This curve of efficiency is as good as that obtained with RFCNU and RPCNU described by IMBACH et al. (Loc. Cit) and it is very distinctly higher than those obtained by CCNU and Me CCNU described by MATHE and KENIS (Loc. cit).

(c) A sudden drop of the T/C is observed after 40 mg/kg. This phenomenon is also observed wiht nitrosoureas used as comparison products:the rapid rise in toxicity cancelled the efficiency of the product.

3.4. The value of T/C ≦125% was sought in order to determine a minimum active dose which is situated between 1.25 mg/kg of body weight and 2.5 mg/kg; in fact, at 1.25 mg/kg it is found to be slightly below the significant threshold of 125% survival, which is not the case at the dose of 2.5 mg/kg.

4. Determination of the "in vivo" activity of the compounds according to the invention on the three respective tumors leucemia L 1210 IGR, Lewis tumor and melanoma B16

The compounds tested were the compounds of examples referenced by IC 1183, IC 1184, IC 1350, IC 1373 and IC 1374.

4.1. L1210

Female DBA$_2$ mice were used, about 8 weeks old and weighing about 20 g from the IFFA-CREDO center (les Oncins, 69210 Arbresles)

At day "0", each mouse received intraperitoneally an inoculum of 1×10 tumor cells in a volume of 0.2 ml. After tumoral graft, the mice were distributed at random into 21 cages of 5 animals, themselves then distributed, by drawing lots, into 6 experimental series. Within these 6 experimental series, there were constituted a control series of 6 cages and 5 experimental series of 3 cages each, and of which the mice were intended to be treated by the compounds of the invention.

4.2. Melanoma B16

Female C57 B1/6 mice were used, about 8 weeks old and weighing about 20 g, from the IFFA-CREDO center.

At day "0", each mouse received intraperitoneally an inoculum of $2 \times 10^6$ tumor cells in a volume of 0.5 ml.

After tumoral graft, distribution at random was carried out as indicated above, to obtain a control series of 8 cages and 5 experimental series of 4 cages each, and of which the mice were intended to be treated by the compounds of the invention.

4.3. Lewis tumor

Procedure was under the conditions which have just been described previously with regard to melanoma B16, by injecting the tumor cells, in the proportion of $2 \times 10^6$ per mouse, in the volume of 0.2 ml.

4.4. Protocol and treatment

The protocol was identical for the 3 tumors and the 5 compounds of the invention to be tested.

As regards the experimental series to be treated, each mouse received, at days 1, 5 and 9, intraperitoneally, a dose of 20 mg/kg of the compound to be tested, in the volume of 0.2 ml of neutralized and sterilized olive oil.

As regards the control series, each mouse received, intraperitoneally, 0.2 ml of neutralized and sterilized olive oil.

4.5. Results

Control series (comparison)

The average survival of the comparison mice is expressed in days ±2 typical deviation of the mean (±26 σm):

L1210:8, 9±0.26
3LL Lewis tumor:12.87±0.79
Melanoma B16:14.52±0.80.

Treated series (see Table II below)

The results are expressed by the relative increase in survival (T/C×100) calculated from the average survival of the treated animals (T) and that of the control animals (C)

The mice surviving more than 60 days were considered as cured.

The figures between parentheses indicate the percentage of cured mice.

The sign ∞ indicates that 50% at least of the mice were cured.

When the percentage of mice cured is less than 50%, the cured mice are considered as dead at 60 days for the calculation of the T/C×100 (in this case the T/C×100 is hence more or less underestimated).

Among the mice which had lived at least 60 days, and hence considered as cured, certain were killed at the 60th day. No anomaly was observed in macroscopic examinations of the organs removed.

The other mice were preserved and kept alive to the 200th day; they did not manifest any apparent disturbance in their behavior.

The animals which died in the course of the experiment were autopsied and there was no death through toxicity.

TABLE II

| Tumor | Compound tested | | | | |
|---|---|---|---|---|---|
| | I.C. 1183 | I.C. 1184 | I.C. 1350 | I.C. 1373 | I.C. 1374 |
| Leucemia 1210 | ∞ (100) | 556 (47) | 362 (20) | ∞ (100) | ∞ (67) |

TABLE II-continued

| Tumor | Compound tested | | | | |
|---|---|---|---|---|---|
| | I.C. 1183 | I.C. 1184 | I.C. 1350 | I.C. 1373 | I.C. 1374 |
| Tumor LEWIS | ∞ | ∞ | 325 | 316 | ∞ |
| 3LL | (75) | (90) | (40) | (30) | (75) |
| MELANOMA | 234 | 235 | 225 | 165 | 246 |
| B 16 | (5) | (15) | (5) | (0) | (10) |

5. Determination of the "in vivo" activity of the compounds according to the invention on the tumors L1210 USA and L1210 IGR The tumor L1210 USA is more resistant than tumor L1210 IGR.

The compounds tested were compounds IC1183, IC 1184, IC 1350, IC 1373 and IC 1374.

The experiments were identical to those described in preceding paragraph 4 but lower doses were used.

There were inoculated into the mice, $10^5$ tumor cells of L1210 USA intraperitoneally in a volume of 0.2 ml.

At days 1, 5 and 9, the compounds of the invention under test were injected intraperitoneally, at a lower dose than that used in the experiment described at 4, that is to say in the proportion of 5 mg/kg.

The same protocol was carried out with the tumor L1210 IGR, by inoculating $10^5$ tumor cells of L1210 IGR intraperitoneally in the volume of 0.2 ml then, at days 1, 5 and 9, there were injected intraperitoneally 5 mg/kg of each of the compounds to be tested.

The results are shown in Tables III and IV below.

On the contrary, the hepatic structure of mice inoculated by L1210 IGR, then treated with the products according to the invention, did not show as great a disturbance as that observed with the comparison mice inoculated with L1210 IGR, and the hepatic nuclear hypertrophy does not consequently seem to be connected with the toxicity itself of the products of the invention.

A hematological study has been carried out on some animals treated with the products according to the invention; it is the case particularly of $DBA_2$ mice inoculated with L1210 leucemia and C57/B16 mice which have been inoculated with Lewis tumor. The study comprised, from a blood sampling by cardiac puncture, collected on heparin, a blood count (erythrocytes and leukocytes), hematocrit, platelet count, differential blood count.

From marrow smears of femoral origin and from a spleen print, a short study of hematopoietic centers has been undertaken.

A histological study has also been carried out on

TABLE III

| | L 1210 USA Tumor | | | | | |
|---|---|---|---|---|---|---|
| | (Comparison) Controles | IC 1350 | IC 1373 | IC 1374 | IC 1183 | IC 1184 |
| Average survival ± 2 σ m | 8,6 ± 0,22 | 10,5 ± 0,74 | 10,6 ± 0,44 | 12,9 ± 0,55 | 13,5 ± 0,91 | 18 ± 1,19 |
| Variance ($S_m^2$) | 0,013 | 0,139 | 0,049 | 0,077 | 0,205 | 0,355 |
| T/C × 100 | | 126 | 123 | 150 | 157 | 209 |
| Median survival | 8,7 | 10,25 | 10,6 | 13,1 | 14,0 | 17,8 |
| T/C × 100 | | 118 | 122 | 151 | 161 | 205 |

TABLE IV

| | L 1210 IGR TUMOR | | | | | |
|---|---|---|---|---|---|---|
| | (Comparison) Controles | I.C. 1350 | I.C. 1373 | I.C. 1374 | I.C. 1183 | I.C. 1184 |
| Average survival ± 2 σ m | 9,05 ± 0,18 | 14,3 ± 1,23 | 12,9 ± 0,55 | 17,1 ± 2,10 | 18,7 ± 1,30 | |
| Variance ($S_m^2$) | 0,008 | 0,379 | 0,077 | 1,10 | 0,423 | |
| T/C × 100 | | 158 | 142 | 189 | 207 | 378 |
| Median survival | 9,05 | 14,25 | 13,1 | 16,75 | 19 | 24 |
| T/C × 100 | | 157 | 145 | 185 | 210 | 265 |

6. Study of the toxicity of the compounds according to the invention

Histological examinations were carried out on the organs of $DBA_2$ mice inoculated by the tumor L1210 IGR and treated for 60 days with products IC 1183, IC 1184, IC 1350, IC 1373 and IC 1374, as well as on organs of the comparison $DBA_2$ mice, that is to say inoculated with the tumor L1210 IGR.

The organs subjected to these histological examinations were the liver, the kidneys, the spleen, the adrenal glands and the lungs.

Examination showed that the comparison animals inoculated by L1210 IGR presented a cellular disorganisation of the hepatocytes.

liver, spleen, kidneys, adrenal glands, lungs, which were sampled when the animals were killed.

No important disturbances have been observed, either in the blood count or in the differential blood count; there is no bone marrowaplasia and the marrows which have been observed are rich in cells of all kinds. The spleens seem to be substantially normal.

7. General conclusion

The animal experiments carried out with the product according to the invention give interesting results when the model selected in melanoma B16, and excellent results when the models selected are the Lewis tumor and the L1210 IGR tumor as well as the L1210 USA tumor, more resistant than the L1210 IGR.

The compounds according to the invention are hence particularly suitable for the treatment of various human cancers, especially those which are sensitive to chimiotherapy. The compounds of the invention are particularly suitable for the treatment of various forms of cancer meeting this condition and which are identified in the publications already mentioned. The compounds of the invention are also suitable for the treatment of primary and secondary cerebral tumors, broncho-pulmonary tumors, tumors of the ORL sphere, digestive tumors (gastric, pancreatic, colic and rectal), tumors of the breast, of the genital organs in the woman, bone tumors (osteosarcomas, reticulosarcomas), melanomas, hemato-sarcomas (Hodgkinian and non Hodgkinian lymphomas), and multiple myelomas.

The invention relates also to pharmaceutical compositions comprising the above said novel compounds in association with a pharmaceutical vehicle suitable for the selected mode of administration.

The invention relates particularly to sterile or sterilizable solutions, injectable or suitable for use for the preparation, particularly extemporaneously, of injectable solutions suitable for administration by intravenous injections or perfusions. They relate, in particular, to physiologically acceptable hydroalcoholic solutions.

The products according to the invention, may be for instance presented in the form of freeze-dried powder, which, for administration, is prepared extemporaneously by solubilisation by means of a sterile alcoholic solvent. The solution so-obtained is then diluted with apyrogenic sterile water, then before being administered by intravenous perfusion, the solution is again rediluted in 9%, isotonic salt serum of 5% isotonic glucose serum.

The doses administered daily must be sufficient so that an action can be manifested at least in a relatively large proportion of patients afflicted with one or other of the various forms of cancer which are or will be accessible to chimiotherapy, however without nonetheless exceeding those for which the compounds become too toxic.

More particularly, the doses to be administered are determined according to models conventionally used in this field which are, for example, described in the two following articles:

Cancer Research, 37, 1 934-937, June 1977, P. S. Schein;
Cancer Chimiotherapy Reports, vol. 50, no. 4, May 1966, E. J. Freireich.

The model for determining the suitable doses for a given compound, consist of determining the dose which is tolerated by the animal and which corresponds to about 1/10 of the lethal dose (LD10) expressed in mg/m2 of body surface. The doses which can be used in man correspond to ⅓ to 1/10 of the LD10 dose mentioned above (cf. Cancer Research, 37, 1935, column 1, June 1977).

By way of example, the daily doses administered by the general route, particularly by perfusion, and expressed in mg/kg can vary from about 1 to about 50 mg/kg, for example, about 3 mg/kg.

The invention also relates to other forms of administration, especially, for the oral route (solid or liquid compositions) or for the rectal route (glycerin compositions suitable for the latter route).

These dosage ranges are obviously only by way of indication. It is naturally understood that in this type of therapy, the doses administered must in each case be evaluated by the clinician taking into account the state of the patient and of his personal reactivity with respect to the medicaments.

An example of pharmaceutical composition of the products according to the invention comprises 100 mg of at least one of the products of the invention, presented in the form of a sterile freeze-dried powder, associated with an ampoula of physiologically acceptable solvent, particularly of alcohol, such as ethanol, at the dosage of about 5 ml per ampoula.

Because of their particularly important activity, the compounds of the invention are also useful as reference products in pharmacological studies, particularly in order to carry out antitumor comparisons of the products which are studied with respect to a reference product.

EXAMPLE 28

Preparation of methyl 3-[3-(2-chlorethyl)3-nitroso ureido] 3,4-dideoxy-β-D-xylo-hexopyranoside (CI. 1675)

(1) Preparation of methyl 3-azido 6-benzoyl 3-deoxy-β-D-gluco-hexopyranoside 29 g of 3-azido 3-deoxy D-gluco-hexopyranoside are dissolved in 600 ml of 1N hydrogen chloride in methanol, the solution is heated under reflux for 2 hours and then evaporated to dryness in a vacuum.

The product is taken up in dichloromethane and washed with water until chloride ions have been completely removed. The organic phase is dried over sodium sulfate then evaporated to dryness in a vacuum to give a residue of 31 g of glycosylated product which is used as such in the next step.

The crude product is dissolved in 250 ml of anhydrous toluene. 90 ml of bis tributyl tin oxide are then added and the reaction mixture is then refluxed for 3 hours. The reaction mixture is cooled to −15° C. and a solution of 40 ml of benzoyl chloride in 200 ml of methylene chloride is added dropwise. After being stirred for 24 hours, the reaction mixture is evaporated to dryness in a vacuum, then chromatographed on silica (eluant: $CH_2Cl_2:CH_3OH$, 98:2).

This leads to the isolation, in the form of resinous substances, of:

7.5 g of methyl 3-azido 6-benzoyl 3-deoxy-β-D-gluco-hexopyranoside. $[\alpha]_D = -3.5°$ (c,0.83 $CHCl_3$)

7.0 g of methyl 3-azido 6-benzoyl 3-deoxy-α-D-gluco-hexopyranoside. $[\alpha]_D = +102.0°$ (c,1.14 $CH_2Cl_2$).

(2) Preparation of methyl 3-azido 6-benzoyl 4-chloro 3,4 dideoxy-β-D-galacto-hexopyranoside To 4.8 g (0.015 mole) of methyl 3-azido 6-benzoyl 3-deoxy-β-D-gluco-hexopyranoside in 250 ml of anhydrous pyridine 12.5 ml (0.15 mole) of sulfuryl chloride are added dropwise at 0° C. The solution is stirred for 18 hours at 0° C., then allowed to warm to room temperature. The reaction mixture is then poured onto 500 g of ice and extracted with dichloromethane.

The organic phase is washed with 1N sulfuric acid, then with water, dried over sodium sulfate, filtered and evaporated. The oily residue is purified by chromatography on silica using the eluant hexane-ethyl acetate 4:1 to give 4.05 g (80%) of white crystals.

$C_{14}H_{16}ClN_3O_5$: 341.7.

mp: 84°–86° (hexane-ethyl acetate).

$[\alpha]_D$: +2.3° (c,0.88 $CHCl_3$).

(3) Preparation of methyl 3-amino 6-benzoyl 3,4-dideoxy-β-D-xylohexopyranoside

To 4.05 g (0.012 mole) of the preceding compound in 200 ml of anhydrous toluene is added azo-bis-isobutyronitrile (700 mg., 4.27 mmoles), followed, under nitrogen and dropwise, by tributyl tin hydried (12.6 ml, 47 mmoles). The reaction mixture is refluxed for 2 hours and then evaporated under reduced pressure.

After chromatography on silica using the eluant dichloromethaneammoniacal methanol 19:1, 3 g (90%) white crystals are isolated.

$C_{14}H_{19}NO_5$:281.3.
mp:112°–117°.
$[\alpha]_D$: −13.6° (c,0.3% $CH_3OH$).

(4) Preparation of methyl 3-amino 3,4 dideoxy-β-D-xylo-hexopyranoside

To 3 g (0.0107 mole) of the preceding compound in methanol (45 ml) is added a molar solution of sodium methylate (5 ml). After being stirred for 2 hours at room temperature the reaction mixture is evaporated under reduced pressure. The residue is purified by chromatography on silica using the eluant dichloromethane-ammoniacal methanol 17:3.

1.5 g of crystalline product are isolated.

$C_7H_{15}NO_4$:177.2. mp:155°–158° (acetonitrile). $[\alpha]_D$: −43.5° (c,0,74 $CH_3OH$).

(5) Preparation of methyl 3-[3-(2-chloro ethyl)3-nitroso ureido]3,4-dideoxy-β-D-xylo-hexopyranoside $5 \times 10^{-3}$ mole of methyl 3-amino 3,4-dideoxy-β-D-xylo-hexopyranoside are dissolved in 2 ml of anhydrous DMF and $5 \times 10^{-3}$ mole of 2-chloroethyl isocyanate are added dropwise at 0° C. with stirring. After being stirred for 5 hours, the reaction mixture is evaporated to dryness in a vacuum. A residue is dissolved in 8 ml of formic acid. 0.036 mole of sodium nitrite are added in small portions and with stirring to the solution maintained at 0° C. After 30 minutes 10 ml of water are added and stirring is continued for 1 hour. The reaction mixture is poured into 100 ml of pure ethyl acetate, dried over sodium sulfate and evaporated to dryness. The residue is purified by crystallization from isopyrpyl ether.

Analysis: $C_{10}H_{18}ClN_3O_6$: 311.7 Yield: 49% mp: 111°–112°.
$[\alpha]_D$:+5.7° (c,1.4% $CH_3OH$).

EXAMPLE 29

Preparation of methyl 3-[3-(2-chloro ethyl)-3 nitroso ureido]6-benzoyl 3,4-dideoxy-β-D-xylo-hexopyranoside (CI. 1674)

Methyl 3-amino 6-benzoyl 3,4-dideoxy-β-D-xylo-hexopyranoside is prepared as described in Example 1, step 3, then the amine obtained is treated as described in Example 1, step 5.

Analysis: $C_{17}H_{22}ClN_3O_7$:415.83 Yield:60%.
mp: 108°
$[\alpha]_D$:+7.3 (c, 0.28 $CH_3OH$).

EXAMPLE 30

Preparation of methyl 4-chloro 3-[3-(2-chloroethyl)3nitrosoureido]3,4-dideoxy-β-D-galacto-hexopyranoside (CI: 1803)

(1) Preparation of methyl 3-amino 6-benzoyl 4-chloro 3,4-dideoxy-β-D-galacto-hexopyranoside To 3 g of methyl 3-azido 6-benzoyl 4-chloro 3,4-dideoxy-β-D-galacto-hexopyranoside in 100 ml of absolute ethanol and 2 ml of triethylamine 500 mg of 10% palladium on charcoal are added under nitrogen and the reaction mixture is stirred in an atmosphere of hydrogen for 24 hours.

After the catalyst has been removed the filtrate is evaporated; the residue is purified by chromatography on silica.

The product is recrystallized from ethyl ether.
Analysis: $C_{14}H_{18}ClNO_5$: 315.5. Yield: 82%.
mp: 160°–162°.
$[\alpha]_D$= −11.0° (c,0.85 $CHCl_3$).

(2) Preparation of methyl 3-amino 4-chloro 3,4 dideoxy-β-D-galacto-hexopyranoside The debenzoylation is carried out according to the standard procedure using sodium methylate.

The product obtained has the following properties:
Analysis: $C_7H_{14}ClNO_4$:211.5.
mp: 158°–162°.
$[\alpha]_D$:−4.0° (c,0.84 $CHCl_3$).

(3) Preparation of methyl 4-chloro 3-[3-(2-chloro ethyl) 3-nitroso ureido]3,4 dideoxy-β-D-galacto-hexopyranoside.

The preparation was carried out as was described in Example 1, step 5, starting from the compound obtained in step 2 above.

Analysis: $C_{10}H_{17}Cl_2N_3O_6$: 346.17.
mp: 145°–148°.
$[\alpha]_D$:+30° (c, 0.65 MeOH).

EXAMPLE 31

Preparation of methyl 3-[3-(2-chloro ethyl)3-nitroso-ureido] 3,4 -dideoxy-αD-xylo-hexopyranoside (CI. 1677)

(1) Preparation of methyl 3-azido 6-benzoyl 3-α-D-gluco-hexopyranoside 29 g of 3-azido 3-deoxy D gluco-hexopyranoside are dissolved in 600 ml of 1N methanolic hydrogen chloride and the solution is heated at reflux for 2 hours, then evaporated to dryness in a vacuum.

The product is taken up in dichloromethane and the solution is washed with water until chloride ion can no longer be detected. The organic phase is dried over sodium sulfate and evaporated to dryness in a vacuum to give a residue of 31 g of glycosylated product used as such in the next step.

The crude product is dissolved in 250 ml of anhydrous toluene. 90 ml of bis tributyl tin oxide are then added and the mixture is refluxed for 3 hours. The reaction is cooled to −15° C. and a solution of 40 ml of benzoyl chloride in 200 ml of dichloromethane are added dropwise. After being stirred for 24 hours, the reaction mixture is evaporated to dryness in a vacuum and the residue obtained is chromatographed on silica (eluant $CH_2Cl_2$:$CH_3OH$, 98.2).

This results in the isolation, in the form of resinous substances, of:

7.5 g of methyl 3-azido 6-benzoyl 3-deoxy-β-D-glucohexopyranoside 7.0 g of methyl 3-azido 6-benzoyl 3-deoxy-α-D-glucohexopyranoside (2) Preparation of methyl 3-azido 6-benzoyl 4-chloro 3,4-dideoxy-α-D-galacto-hexopyranoside.

To 4.8 g (0.015 mole) of methyl 3-azido 6-benzoyl 3-deoxy-α-D-gluco-hexopyranoside in 250 ml of anhydrous pyridine are added dropwise at 0° C. 12.5 ml (0.015 mole) of sulfuryl chloride. The solution is stirred for 18 hours at 0° C., then allowed to warm to room temperature. The reaction mixture is then poured onto 500 g of ice and extracted with dichloromethane.

The organic phase is washed with 1 N sulfuric acid, then with water, dried over sodium sulfate, filtered and evaporated. The oily residue is purified by chromatography on silica using the eluant hexane-ethyl acetate 4:1 to give 4.05 g (80%) of white crystals.

$C_{14}H_{16}ClN_3O_5$: 341.7.

mp: 104°–106° (hexane-ethyl acetate).

$[\alpha]_D$: +140.5° (c, 1.3 CHCl$_3$).

(3) Preparation of methyl 3-amino 6-benzoyl 3,4-dideoxy-α-D-xylohexopyranoside

To 4.05 g (0.012 mole) of the preceding compound in 200 ml of anhydrous toluene is added azo-bis-isobutyronitrile (700 mg, 4.27 mmoles) followed, dropwise and under nitrogen, by tributyl tin hydride (12.6 ml, 47 mmoles). The reaction mixture is heated at reflux for 2 hours and then evaporated under reduced pressure.

After chromatography on silica using the eluant dichloromethaneammoniacal methanol 19:1, 3 g (90%) of white crystals are isolated.

(4) Preparation of methyl 3-amino 3,4-dideoxy-α-D-xylo-hexopyranoside

To 3 g (0.0107 mole) of the preceding compound in methanol (45 ml) is added a molar solution of sodium methylate (5 ml). After being stirred for 2 hours at room temperature the reaction mixture is evaporated under reduced pressure. The residue is purified by chromatography on silica using the eluant dichloromethane-ammoniacal methanol 17:3.

1.5 g of crystalline produce are isolated.

mp = 130°–134° C.

$[\alpha]_D$: +163° (c,0.9 CHCl$_3$).

(5) Preparation of methyl 3-[3-(2-chloroethyl) 3-nitroso ureido] 3,4 dideoxy-α-D-xylo-heoxpyranoside $5 \times 10^{-3}$ mole of methyl 3-amino 3,4-dideoxy-α-D-xylo-hexopyranoside are dissolved in 2 ml of anhydrous DMF and $5 \times 10^{-3}$ mole of 2-chloroethyl isocyanate are added dropwise at 0° C. with stirring. After being stirred for 5 hours, the reaction mixture is evaporated to dryness in a vacuum. A residue is dissolved in 8 ml of formic acid. 0.036 mole of sodium nitrite are added in small portions and with stirring to the solution maintained at 0° C. After 30 minutes 10 ml of water are added and stirring is continued for 1 hour. The reaction mixture is poured into 100 ml of pure ethyl acetate, dried over sodium sulfate and evaporated to dryness. The residue is purified by crystallization from isopropyl ether.

Analysis: $C_{10}H_{18}ClN_3O_6$: 311.7.

mp: 109°–110°.

$[\alpha]_D$: +120.8° (c,0.48% MeOH).

EXAMPLE 12

Preparation of methyl 4-chloro 3-[3-chloro-ethyl) 3-nitroso ureido] 3,4-dideoxy-α-D-galacto-hexopyranoside (CI. 1676)

(1) Preparation of methyl 3-amino 6-benzoyl 4-chloro 3,4-dideoxy-α-D-galacto-hexopyranoside To 3 g of methyl 3-azido 6-benzoyl 4-chloro 3,4-dideoxy-α-D-galacto-hexopyranoside in 100 ml of absolute ethanol and 2 ml of triethylamine 500 mg of 10% palladium on charcoal are added under nitrogen and the reaction mixture is stirred in an atmosphere of hydrogen for 24 hours.

After the catalyst has been removed the filtrate is evaporated; the residue is purified by chromatography on silica.

The product is recrystallized from ethyl ether.

Analysis: $C_{14}H_{18}ClNO_5$: 315.5.

mp: 161°–164°.

$[\alpha]_D$: +118.5° (c, 1.25 CHCl$_3$).

(2) Preparation of methyl 3-amino 4-chloro 3,4-dideoxy-60-D-galactohexopyranoside The debenzoylation is carried out according to the standard procedure using sodium methylate.

The product obtained has the following properties:

Analysis: $C_7H_{14}ClNO_4$: 211.5.

mp: 135°–138°.

$[\alpha]_D$: +184° (c, 0.92 MeOH).

(3) Preparation of methyl 4-chloro 3-[3-(2-chloroethyl) 3-nitroso ureido] 3,4-dideoxy-α-D-galacto-hexopyranoside The preparation was carried out as described in example 1, step 5, starting from the compound obtained in step 2 above.

Analysis: $C_{10}H_{17}Cl_2N_3O_6$: 346.17.

mp: 129°–130°.

$[\alpha]_D$: +139.3° (c, 0.5 CH$_3$OH).

PHARMACOLOGICAL STUDY

In order to test the antitumor activity of the compounds of formula IA, use has primarily been made of murine leukemia L1210. Use has also been made of the tumor melanoma B16. In particular, the products of the invention have been tested against the melanoma B16 by administering them by the I.P. and by the I.V. routes.

The compounds of formula IA have also been tested against the colon carcinoma C38 by administering them by the I.P. and I.V. routes.

In practice, the biological effects of the novel nitrosourea derivatives corresponding to the present invention were tested as follows:

PROTOCOL FOR TREATMENT WITH THE PRODUCTS OF THE INVENTION

I. MATERIALS AND METHODS

A. Tumors used

Two murine tumors were used for the "in vivo" studies: the leukemia L1210 and the melanoma B16.

(1) LEUKEMIA L1210

Animals

The experiments were also performed on female mice which were specific pathogen-free (S.P.F.) of
either the line DBA/2JIco
or line B6 D 2 F1/JIco
(first generation hybrids between the lines C57BL/6 and DBA/2). The line used is specified for each series of experiments.

Tumoral graft

On the day of the graft (by convention day O=DO) an inoculum of $1 \times 10^5$ tumor cells in the a volume of 0.2 ml is administered to each mouse by the intraperitoneal route (I.P.).

This inoculum is prepared by diluting ascites fluid taken from the peritoneum of a donor female mouse in NCTC 109 medium (Eurobio Laboratories Paris, France), counting of the cells in a MALASSEZ cell under a microscope and adjustment of the concentration to $5 \times 10^5$ cells per ml.

Distribution in experimental groups

After the tumor graft has been made, the mice are distributed at random in cages of 5 animals. Subsequently, these cages containing 5 mice are themselves distributed at random into a control group (control) and groups treated with the products of the invention.

(2) MELANOMA B16

Animals

The experiments were always carried out on SPF female mice B6 D2 F1/JIco (first generation hybrids between the lines C5BL/6 and DBA/2).

Tumoral graft

On the day of the graft (Day 0) an inoculum of $2 \times 10^6$ tumor cells in a volume of 0.5 ml is administered to each mouse by the intraperitoneal route (I.P.). This inoculum is prepared from a sub-cutaneous tumor excised from a donor female mouse. After excision the tumor is fragmented by means of a pair of scissors in the NCTC 109 medium. After filtration through sterile gauze in order to remove large cellular fragments, the homogeneous cell suspension obtained is counted by means of a MALASSEZ cell and diluted to the desired concentration ($4 \times 10^6$ tumor cells per ml) by dilution with the NCTC 109 medium.

Distribution in experimental groups

This was performed in the manner described previously for the leukemia L1210.

B. Protocol for treatment

The doses of the products of the invention used in the different experiments are expressed in milligrams per kilogram of body weight.

The products to be injected were dissolved in isotonic sodium chloride solution.

Two protocols for treatment were used in the different experiments:

either a single injection on D1, by the intraperitoneal (I.P.) or intravenous (I.V.) route, or 3 I.P. injections on D1, D5, D9.

In each experiment the animals of the control group received 1 or more injections, depending on the experimental protocol used, by the same route (I.P. or I.V.) of the same volume (0.2 ml/20 g) of the vehicle not containing the active principle (isotonic sodium chloride solution).

II. EXPRESSION OF THE RESULTS

For each experiment a table specifies:

the number and percentage of the total of the mice surviving to D60, the T/C×100 for the treated groups.

T repreesnting the mean survival time of the mice in the treated group

C representing the mean survival time of the mice in the control group (control).

III. COMMENT

The strains of mice used, the experimental protocols and the mode of expression of the results are in accordance with directive 271 F of the "N.C.I. Division of Cancer Treatment" (November 1983).

IV. PHARMACOLOGICAL RESULTS (1) Toxicological study:

The results relating to toxicology are brought together in Table IA below:

TABLE IA

| CI | $LD_0$ mg/kg | $LD_{50}$ mg/kg | $LD_{90}$ mg/kg |
|---|---|---|---|
| 1674 | $\geq 40$ | — | — |
| 1675 | $\geq 20$ | approximately 40 | — |
| 1676 | $\geq 20$ | — | — |
| 1677 | — | — | $\leq 20$ |

(2) Activity of the products CI. 1674, 1675, 1677 by the I.P. route on the leukemia L1210 USA strain and the melanoma B16.

| T/C | Number of survivors at D60 |
|---|---|
| Compound of the invention CI. 1674 L1210 USA strain - $B_6D_2S_1$ - I.P. treatment on D1, D5, D9 $3 \times 1.25$ mg/kg, $3 \times 5$ mg/kg | |
| $3 \times 1.25$ — 111 | 0/10 |
| $3 \times 5$ — 130 | 0/10 |
| Compound of the invention CI. 1675 L1210 USA strain - $B_6D_2F_1$ - I.P. treatment on D1, D5, D9 $3 \times 1.25$ mg/kg, $3 \times 5$ mg/kg | |
| $3 \times 1.25$ — 164 | 0/10 |
| $3 \times 5$ — >600 | 5/10 |
| Melanoma B16 - $B_6D_2F_1$ - I.P. treatment on D1, D5, D9 $3 \times 10$ mg/kg | |
| 258 | 8/10 |
| Compound of the invention CI. 1676 L1210 USA strain - $B_6D_2F_1$ - I.P. treatment on D1, D5, D9 $3 \times 1.25$ mg/kg, $3 \times 5$ mg/kg | |
| $3 \times 1.25$ — 136 | 0/10 |
| $3 \times 5$ — 188 | 0/10 |
| Melanoma B16 - $B_6D_2F_1$ - I.P. treatment on D1, D5, D9 $3 \times 10$ mg/kg | |
| 202 | 3/10 |
| Compound of the invention CI. 1677 L1210 USA strain - $B_6D_2F_1$ - I.P. treatment on D1, D5, D9 $3 \times 1.25$ mg/kg, $3 \times 5$ mg/kg | |
| $3 \times 1.25$ — 157 | 0/10 |
| $3 \times 5$ — >600 | 6/10 |
| Melanoma B16 - $B_6D_2F_1$ - I.P. treatment on D1, D5, D9 $3 \times 10$ mg/kg | |
| 257 | 7/10 |

(3) Activity of the substances of the invention toward melanoma B16 after administration by the intravenous route:

The activity of the substances of the invention was also tested by administering the said substances of the invention by the I.V. route. 0.5 ml of an homogenate of the tumor (1 g/10 ml) is administered to B6C3F1 female mice by the subcutaneous (S.C. route) on day 0. The products of the invention and the substances used for comparison are administered on days 3, 7 and 11 in isotonic solution.

In Table IIA below the results are presented relating to the activity of the substance CI. 1675 administered by the I.V. route on the growth of the melanoma B16 implanted subcutaneously, in comparison with carmustine BCNU marketed under the name of BiCNU$^R$.

In Table IIA below and in the subsequent tables, T represents the mean weight (or median) of the tumors in the treated mice, C represents the mean weight (or median) of the tumors in the control, untreated mice and the ratio T/C % corresponds to T/C×100.

TABLE IIA

| Product | Dose mg/kg/inj. | Median weight of the tumor on day 3 (mg) | Median weight of the tumor on day 30 (mg) | T/C on day 30 |
|---|---|---|---|---|
| IC1675 | 20 | 36,0 | 688 | 8,8 |
|  | 15 | 23,0 | 1 044 | 13,4 |
|  | 10 | 32,0 | 2 025 | 25,9 |
| BCNU | 20 | 40 | 2 581 | 33,0 |
| Controls | 0 | 40 | 7 812 | 100 |

In this case it should be noted that the smaller the ratio the better is the activity, in the ideal case, the weight of the tumor in the treated mouse is 0 mg and hence the ratio T/C % is equal to 0.

The results obtained show that the substances of the invention are active when they are administered by the I.V. route, a finding which makes them quite suitable for use in human therapy.

(4) Activity of the substance of the invention CI. 1675 administered by the I.P. route to mice bearing the colon carcinoma C38, implanted subcutaneously.

A tumor fragment is implanted on day 0 in female $B_6D_2F_1$ mice (19–22 g). The treatment with all of the products is administered by the i.P. route on days 2 and 9 (which is a delayed treatment). The weight of the tumors is calculated on day 20.

The results are presented in Table IIIA below.

TABLE IIIA

| Product | Dose mg/kg/inj. | Weight of the tumor on day 20 (mg) | T/C % | Number of mice without tumor/total + remarks |
|---|---|---|---|---|
| IC 1675 | 30 | 0 | 0 | 7/7 and 5 dead mice |
|  | 20 | 0 | 0 | 7/9 |
|  | 10 | 272 | 67 | 1/10 |
| TCNU | 30 | — | — | 10 prematurely dead |
|  | 15 | 0 | 0 | 7/10 |
|  | 7.5 | 266 | 65 | 2/10 |
| Controls | 0 | 405 | 100 | 0/32 |

Table IIIA above illustrates the considerable efficacy of the substance of the invention CI.1675 against the colon carcinoma C38 when it is administered by the i.P. route by delayed treatment. This is predictive of activity in man for treatment against various tumors.

(5) Antitumor activity of the substance CI.1675 against the colon carcinoma C38: comparison of the intravenous and intraperitoneal routes With a view of verifying the antitumor activity of the product of the invention CI.1671 when it is administered by the I.V. route, another experiment was performed in which this product was administered by the I.P. route and the I.V. route for the purposes of comparison.

This experiment is carried out under particularly difficult conditions, the first day of the treatment corresponding to the eighth day after the implantation of the carcinoma C38, whereas normally the treatment starts on the day of implantation of the tumor (D0) or 1 day after (D1) the implantation of the tumor.

The median weight of the tumors on the first day of treatment (day 8) is about 12 mg (tumors varying from 8 to 40 mg). The animals are treated on days 8, 12 and 16 depending on the different routes indicated.

The results relating to the action of the substance of the invention CI.1675 in mice bearing the adenocarcinoma 38 of the colon are brought together in Table IVA below.

TABLE IVA

| | | I.P. Route | | | | | | I.V. Route | | | | | |
|---|---|---|---|---|---|---|---|---|---|---|---|---|---|
| | | Median wt. of the tumor | | T/C % | | Mice without tumor/total | | Median wt. of the tumor | | T/C % | | Mice without tumor/total | |
| Product | Dose mg/kg/inj. | D20 | D27 | D20 | D27 | D20 | D27 | D20 | D27 | D20 | D27 | D20 | D27 |
| IC 1675 | 20 | 13 | 172 | 2 | 13 | 1/8 | 2/8 | 0 | 0 | 0 | 0 | 6/6 | 6/6 |
|  | 15 | 88 | 726 | 15 | 56 | 0 | 0 | 0 | 0 | 0 | 0 | 7/8 | 7/7 |
|  | 10 | 324 | 1099 | 57 | 84 | 0 | 0 | 23 | 352 | 4 | 27 | 0/8 | 0/8 |
| BCNU | 20 | 196 | 274 | 34 | 21 | 0/8 | 0/6 | | | | | | |
| CONTROLS | 0 | 586 | 1295 | 100 | | 0/24 | | 586 | 1295 | 100 | | 0/24 | |

It can be seen that not only is the activity of the compounds of formula IA towards the carcinoma C38 remarkable but that it is even higher after administration by the I.V. route than after I.P. administration, since at doses not producing toxicity (15 mg/kg/injection), a total regression or the tumor can also be observed. In fact, on the 20th day a measurable tumor can no longer be observed at the beginning of the treatment and on the 27th day there was no sign of recurrence. This is demonstrated by the number of mice without a tumor on the 27th day.

GENERAL CONCLUSION

The experiment in animals performed with the compounds of formula IA give very interesting results in the models used: tumor L1210 USA and melanoma B16, and excellent results in the model of the colon carcinoma C38.

All of the results obtained with these models show that the compounds of the invention have a wider spectrum of activity than the other antitumor substances known at present.

Furthermore, the compounds of formula IA offer the remarkable advantage of bringing about the regression of animal tumors very difficult to treat with the known antitumor agents presently available.

Compounds of formula IA are hence therapeutically active substances and, from this point of view, they represent another aspect of the present invention.

The compounds according to the invention are particularly suited to the treatment of various human cancers, particularly those which respond to chemotherapy. They are particularly suited to the treatment of broncho-pulmonary tumors, tumors of the ENT sphere, digestive tumors (gastric, pancreatic, colic and rectal), breast tumors, genital tumors, bone tumors (osteosarcomas, reticulo-sarcomas), melanomas, hepato-sarcomas (Hodgkin and non-Hodgkin lymphomas), multiple myelomas.

The invention also relates to the pharmaceutical composition containing the new compounds mentioned above in combination with a pharmaceutical vehicle appropriate to the chosen mode of administration. The invention relates particularly to injectible sterile solutions suitable for administration by injections or intravenous perfusions. The invention relates in particular to physiologically acceptable aqueous-alcoholic solutions.

The products according to the invention may, for example, be made available in the form of a lyophilized powder, the administration of which requires that it be made up into a solution immediately before use with the aid of a sterile alcoholic solvent. The solution thus obtained is then diluted with pyrogen-free sterile water and then, before being administered by intravenous perfusion, the solution is diluted again with a solution of glucose or isotonic sodium chloride.

The doses administered must be sufficiently high so as to provoke an activity in at least a relatively large proportion of the patients suffering from one or other of the various forms of cancer which are or will become accessible to the chemotherapy without, however, exceeding those doses at which the substances would be too toxic.

As an example, the doses administered systemically, in particular by perfusion, and expressed as mg/kg, may vary from about 0.1 to about 5 mg/kg, for example about 1 mg/kg.

The invention also relates to other forms of administration, in particular by the oral route (liquid or solid compositions).

These dose ranges obviously have only indicative value.

It is of course to be understood that in this type of therapy the doses administered must be assessed by the clinician in each case, on which occasion the condition of the patient and his personal reactivity towards medicines is taken into consideration.

An example of the pharmaceutical preparation of the products according to the invention contains from 10 to 250 mg, in particular 50 mg, of at least one of the products according to the invention in the form of a sterile lyophilized powder in combination with an ampoule of a physiologically acceptable solvent, in particular of physiological serum, containing 5 ml of the solvent per ampoule.

As a result of their particularly high activity, the substances of the invention are also useful as reference compounds in pharmacological studies, in particular in those designed to compare the antitumor properties of substances under study in comparison with a reference compound.

EXAMPLE 33

Preparation of methyl 3-[3-(2-chloroethyl) 3-nitroso ureido] 2,3,6-trideoxy β-L-arabino-hexopyranoside (IC 85-1615)

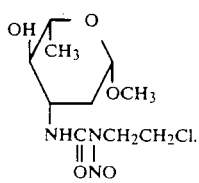

(a) Preparation of methyl 3-azido 2,3,6-trideoxy β-L-arabinohexopyranoside 3 g. (0.016 mole) of methyl 3-azido 2,3,6-trideoxy α-L-arabino hexopyranoside and 1 g. of toluene sulfonic acid in 50 ml of anhydrous methanol are stirred for 48 hours at room temperature.

The reaction mixture is evaporated to dryness in a vacuum. The residue is taken up in methylene chloride. After being washed twice with water, the organic phase is dried over sodium sulfate, evaporated to dryness in a vacuum and chromatographed on a column of silica (eluant hexane-ethyl acetate 5:1).

Analysis: $C_7H_{13}N_3O_3 = 187.20$.
m.p.: 72°–73° (hexane).
$[\alpha]_D = +63.5°$ (c, 0.8 CHCl$_3$).
IR (Nujol) 3370 cm$^{-1}$ (OH) 2100 cm$^{-1}$ (azide).

(b) Preparation of methyl 3-amino 2,3,6-trideoxy β-L-arabino-hexopyranoside

This compound is prepared as indicated in example 8.
Analysis: $C_7H_{15}NO_3 = 161.20$ Yield=85%
m.p.: 136°.
$[\alpha]_D$: +75.8° (c, 0.5 CHCl$_3$).

(c) Preparation of methyl 3-[3-(2-chloroethyl) 3-nitroso ureido] 2,3,6-trideoxy β-L-arabino-hexopyranoside The procedure is the same as that indicated for example 9 in which 2-chloroethyl isocyanate is used and nitrosation is carried out, for example, with the aid of sodium nitrite to give the compound of the invention, the physical properties of which are indicated below.
Analysis: $C_{10}H_{18}ClN_3O_5 = 295.7$.
m.p.: 109°–110°.
$[\alpha]_D = +22.8°$ (c, 0.5% CHCl$_3$).

EXAMPLE 34

Preparation of methyl 3-[3-(2-chloroethyl) 3-nitroso ureido] 2,3,6-trideoxy-L-arabino-hexopyranoside (IC.85-1625)

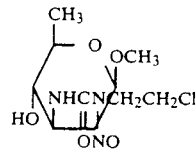

This compound is prepared from methyl 3-amino 2,3,6-trideoxy β-D-arabino-hexopyranoside as indicated, in particular, in the preparation of the compound described in example 9 by using 2-chloroethyl isocyanate and by nitrosating with the aid, for example, of sodium nitrite.

The physical properties of the compound of the invention are as follows:
Analysis: $C_{10}H_{18}ClN_3O_5 = 295.7$.
m.p. 130°–105°.
$[\alpha]_D = -25.0°$ (c, 0.3% CHCl$_3$).

EXAMPLE 35

Preparation of methyl 3-[3-(2 chloroethyl) 3-nitroso ureido] 2,3-dideoxy β-D-arabino-hexopyranoside (IC 85-1673)

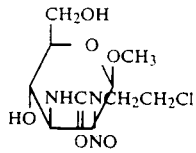

Preparation of methyl 3-azido 2,3 dideoxy
β-D-arabino-hexopyranoside 19.2 g. (0.095 mole) of methyl 3-azido 2,3-dideoxyα-D-arabino-hexopyranoside and 1 g. of p-toluene sulfonic acid in 200 ml of methanol are stirred for 48 hours at room temperature. The residue obtained after evaporation in a vacuum is taken up in 60 ml of anhydrous pyridine.

30 g. of acetic anhydride are added drop-wise while the temperature is maintained at 15°. After being stirred for 16 hours the reaction mixture is evaporated to dryness. The residue is taken up in methylene chloride; the organic phase is washed with a solution of 2N HCl, then with water, and finally with a solution of sodium bicarbonate. The organic phase is dried over sodium sulfate, evaporated in a vacuum and chromatographed on silica using as eluant hexane: acetone 4:1 to give 19.5 g. of compound 3 in the form of its diacetate and 2.5 g. of methyl 3-azido 2,3-dideoxy β-D-arabino-hexopyranoside in the form of its diacetate.

This latter compound is taken up in 45 ml of anhydrous methanol and then 5 ml of sodium methoxide are added. After being stirred for 4 hours the solution is neutralized by the addition of Amberlite IRC50 resin. After evaporation the filtrate yields methyl 3-azido 2,3-dideoxy β-D-arabino-hexopyranoside in the form of crystals.

Analysis: $C_7H_{13}N_3O_4$: 203.2.

Preparation of methyl-3-amino 2,3-dideoxy
β-D-arabino-hexopyranoside

This compound is prepared as indicated for example 8.

Analysis: $C_7H_{15}NO_4$: 177.
mp.: 140°-142°.
$[\alpha]_D$: −61.8° (c, 0.55% MeOH).

Preparation of methyl 3-[3-(2-chloroethyl) 3-nitroso
ureido] 2,3-dideoxy β-D-arabino-hexopyranoside The procedure is the same as that indicated, for example, for the preparation of the compound described in example 9 in which 2-chloroethyl isocyanate is used and nitrosation is carried out, for example, by the aid of sodium nitrite to give the compound of the invention with the following physical properties.

Analysis: $C_{10}H_{18}Cl\ N_3O_6$: 311.72 Yield: 70%.
m.p.: 68°-70°.
$[\alpha]_n$: −37.9° (c, 0.36% MeOH).

EXAMPLE 36

Preparation of methyl 3-[3-(2-chloroethyl)
3-nitroso-ureido] 3,4,6-trideoxy
α-D-xylo-hexopyranoside (IC 85-1590)

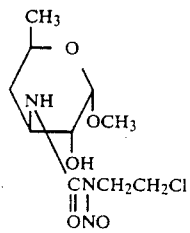

(a) Preparation of methyl 2-0-acetyl 3-azido 4,6-dichloro 3,4,6 trideoxy α-D-galacto-hexopyranoside 52 ml of sulfuryl chloride are added drop-wise to 44 g. (0.21 mole) of 3-azido 3-deoxy D-gluco-pyranose in 160 ml of anhydrous pyridine and 200 ml of chloroform cooled to −78° C. After being maintained for 2 hours at −78° C., the mixture is stirred for 5 hours at room temperature.

The reaction mixture is diluted with 400 ml of chloroform, then washed with 2N hydrochloric acid, water, then with a solution of sodium bicarbonate and again with water. After drying over sodium sulfate and evaporation to dryness in a vacuum, the residue is taken up in 200 ml of methanol to which is then added a 10% solution of potassium iodide in a water-methanol mixture (1:1).

After being neutralized by potassium bicarbonate, the solution is filtered and evaporated and then the residue is taken up in chloroform. The organic phase is washed with a solution of sodium thiosulfate, then with water, dried over sodium sulfate and evaporated to dryness.

The residue is taken up in 100 ml of pyridine and the solution is cooled to 0° C. 20 ml of acetic anhydride are added drop-wise at 0° C. and the solution is stirred for one day, then the reaction mixture is evaporated in a vacuum, the aqueous phase is extracted 2 or 3 times with 200 ml of methylene chloride. The organic phase is then washed with water, evaporated to dryness in a vacuum and 36 g. of a mixture corresponding to the 2 anomers α and β are obtained. The two anomers are isolated in the pure state by chromatography on a column of silica (eluant: hexane-acetone 10:1).

αAnomer: 14.5 g.; m.p.: 74°-76° (hexane-ethyl acetate) $[\alpha]_D = +171°$ (c, 1.17 CHCl$_3$)

βanomer: 16.0 g.; m.p.: 108°-110° (hexane-ethyl acetate) $[\alpha]_D = -6.5°$ (c, 1.58 CHCl$_3$).

(b) Preparation of methyl 3-azido 4,6-dichloro 3,4,6-trideoxy α-D-galacto-hexopyranoside 5 g. (0.017 mole) of the preceding α-anomer are dissolved in 50 ml of anhydrous methanol in the presence of 1 g. of p-toluene sulfonic acid. The reaction mixture is allowed to stand at room temperature for 18 hours and then is evaporated to dryness in a vacuum. The residue is taken up in methylene chloride and the organic phase is washed twice with water, dried, filtered and then evaporated.

The crystals obtained (4.2 g) are recrystallized from a mixture of hexane-ethyl acetate.

Analysis: $C_7H_{11}Cl_2N_3O_3$: 256.
m.p.: 139°-141°.
$[\alpha]_D = +188°$ (c, 1.035 CH$_3$OH).

(c) Preparation of methyl 3-amino 3,4,6-trideoxy α-D-xylo-hexopyranoside to 2 g. (0.0075 mole) of the preceding compound dissolved in 50 ml of anhydrous toluene under nitrogen are added 0.5 g. of azo 2,2'bisisobutyronitrile followed by 8 ml of tributyltin hydride added drop-wise. The reaction mixture is heated under reflux for 10 hours. After the mixture has been cooled and the precipitate has been removed from filtration, the filtrate is evaporated to dryness in a vacuum. Chromatography on silica (eluant: CH$_2$Cl$_2$-ammoniacal MeOH 9:1) leads to the pure amino sugar in the form of white crystals.

Analysis: $C_7H_{15}NO_3$: 161.
m.p.: 136°-139° (ether-methanol).
$[\alpha]_D$: +172° (c, 1% CHCl$_3$).

(d) Preparation of methyl 3-[3-(2-chloroethyl) 3-nitroso ureido] 3,4,6-3 trideoxy α-D-xylo-hexopyranoside (IC 85-1591)

The procedure is the same as that for the preparation of the previous compound.

Analysis: $C_{10}H_{18}ClN_3O_5$: 295.7 Yield: 65%.
m.p.: 103°–105°.
$[\alpha]_D$: +138° (c, 1.41 $CHCl_3$).

EXAMPLE 37

Preparation of methyl 3-[3-(2-chloroethyl) 3-nitroso ureido] 3,4,6-trideoxy β-D-xylo-hexopyranoside (IC 85-1591)

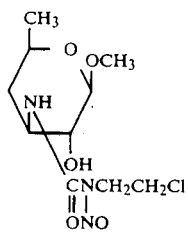

(a) Preparation of methyl 2-O-acetyl 3-azido 4,6-dichloro 3,4,6-trideoxy β-D-galacto-hexopyranoside 52 ml of sulfuryl chloride are added drop-wise to 44 g. (0.21 mole) of 3-azido 3-deoxy D-gluco-pyranose in 160 ml of anydrous pyridine and 200 ml of chloroform cooled to −78° C. After being maintained for 2 hours at −78° C., the mixture is stirred for 5 hours at room temperature.

The reaction mixture is diluted with 400 ml of chloroform, then washed with 2N hydrochloric acid, water, then with a solution of sodium bicarbonate and again with water. After drying over sodium sulfate and evaporation to dryness in a vacuum, the residue is taken up in 200 ml of methanol to which is then added a 10% solution of potassium iodide in a water-methanol mixture (1:1).

After being neutralized by potassium bicarbonate, the solution is filtered and evaporated and then the residue is taken up in chloroform. The organic phase is washed with a solution of sodium thiosulfate, then with water, dried over sodium sulfate and evaporated to dryness.

The residue it taken up in 100 ml of pyridine and the solution is cooled to 0° C. 20 ml of acetic anhydride are added drop-wise at 0° C. and the solution is stirred for one day, then the reaction mixture is evaporated in a vacuum, the aqueous phase is extracted 2 or 3 times with 200 ml of methylene chloride. The organic phase is then washed with water, evaporated to dryness in a vacuum and 36 g. of a mixture corresponding to the 2 anomers α and β are obtained. The two anomers are isolated in the pure state by chromatography on a column of silica (eluant: hexane-acetone 10:1).

α Anomer: 14.5 g.; m.p.: 74°–76° (hexane-ethyl acetate) $[\alpha]_D$= +171° (c, 1.17 $CHCl_3$).

β anomer: 16.0 g.; m.p.: 108°–110° (hexane-ethyl acetate) $[\alpha]_D$= −6.5° (c, 1.58 $CHCl_3$).

(b) Preparation of methyl 3-azido 4,6-dichloro 3,4,6-trideoxy β-D-galacto-hexopyranoside The procedure is the same as that described in part b of IC 85-1590.

Analysis: $C_7H_{11}Cl_2N_3O_3$: 256 Yield: 85%
m.p.: 135°.
$[\alpha]_D$: +10.0° (c, 0.97% $CH_3OH$).

(c) Preparation of methyl 3-amino 3,4,6-3 -trideoxy β-D-xylo-hexopyranoside.

The procedure is the same as that described in part c of IC 85-1590.

Analysis: $C_7H_{15}NO_3$: 161.
m.p.: 148°–149°.

$[\alpha]_D$: −52° (c, 1% $CHCl_3$).

(d) Preparation of methyl 3-[3-(2-chloroethyl) 3-nitroso ureido] 3,4,6-trideoxy β-D-xylo-hexopyranoside The preparation procedure is the same as that for the preceding compound.

Analysis: $C_{10}H_{18}ClN_3O_5$: 295.7 Yield: 90%
m.p.: 84°–90°.
$[\alpha]_n$: +11.5° (c, 1.25 $CHCl_3$).

EXAMPLE 38

Preparation of methyl 3-[3-(2-chloroethyl) 3-nitroso ureido] 3,4,6-trideoxy α-L-xylo-hexopyranoside (IC 85-1626)

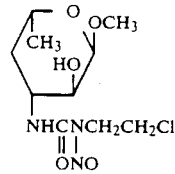

The compound is prepared according to the usual method starting from methyl 3-amino 3,4,6-trideoxy α-L-xylo-hexopyranoside prepared according to H. Baer, Canad. J. Chem., vol. 52, 1974, p. 122–124.

Analysis: $C_{10}H_{18}ClN_3O_5$: 295.7 Yield: 65%
m.p.: 103°–105°. $[\alpha]_D$= −141.5 (c, 0.71 $CHCl_3$).

EXAMPLE 39

Preparation of methyl 3-[3-(2-chloroethyl) 3-nitroso ureido] 3,4,6-trideoxy β-L-xylo-hexapyranoside (IC 85-1627).

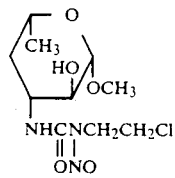

The compound is prepared starting from methyl 3-nitro 3,4,6-trideoxy α-L-xylo-hexopyranoside described by H. Baer, Canad, J. Chem., 52, 1974, p. 122–124.

(1) Preparation of methyl 3-nitro 3,4,6-trideoxy β-L-xylo hexopyranoside 40 ml of 1N hydrogen chloride is methanol are added to 1.8 g. of the above αanomer. After being refluxed for 2 hours the reaction mixture is evaporated to dryness and the residue is purified on a column of silica (eluant: $CH_2Cl_2$-MeOH 98:2).

500 mg of the pure β anomer are obtained.

(2) Preparation of methyl 3-amino-3,4,6-trideoxy β-L-xylo-hexopyranoside.

The preceding compound is dissolved in ethanol and hydrogenated at atmospheric pressure in the presence of platinum oxide.

Analysis: $C_7H_{15}NO_3$: 161 Yield 80%
m.p.: 146°–148°.
$[\alpha]_D$= +36.0° (c , 0.96 $CHCl_3$).

(3) Preparation of methyl 3-[3-(2-chloroethyl) 3-nitroso ureido] 3,4,6-trideoxy-L-xylo-hexopyranoside.

The procedure is the same as that previously described.

Analysis: $C_{10}H_8ClN_3O_5$: 295.7.
m.p.: 90°–92° (isopropyl ether).

$[\alpha]_D$: −9.0° (c, 0.6 CHCl$_3$).

PROTOCOL FOR TREATMENT USING THE PRODUCTS OF EXAMPLES 33-39

I. Materials and methods

A. Tumors used 2 murine tumors were used for the "in vivo" studies: leukemia L1210 and lemanoma B16.

(1) Leukemia L1210

Animals

The experiments were always carried out on female mice which were specific pathogen-free (S. P. F.),
either of the line DBA/2JIco
or of the line B6 D2 F1/JIco (first generation hybrids between the lines C57BL/6 and DBA/2).

The line used in each experiment is specified.

Tumoral graft

On the day of the graft (by convention day 0=DO) an inoculum of 1×10$^5$ tumor cells in a volume of 0.2 ml is administered to each mouse by the intraperitoneal route (I.P.).

This inoculum is prepared by diluting ascites fluid taken from the peritoneum of a donor female mouse in NCTC 109 medium (Eurobio Laboratories, Paris, France), counting of the cells in a MALASSEZ cell under a microscope and adjustment of the concentration to 5×10$^5$ cells per liter by means of the same medium.

The tumor line is an American strain of the line L1210.

Distribution in experimental groups

After the tumor graft, the mice are distributed at random in cages of 5 animals. Subsequently, these cages containing 5 mice are themselves distributed at random into a control group (control) and groups treated with the I.C. products.

(2) Melanoma 16

Animals

The experiments are always carried out on SPF female mice, B6 D2 F1/JIco (first generation hybrids between the lines C57BL/6 and DBA/2).

Tumoral graft

On the day of the graft (day 0), an inoculum of 2×10$^6$ tumor cells in a volume of 0.5 ml is administered to each mouse by the intraperitoneal route (I.P.). The inoculum is prepared from a sub-cutaneous tumor excised from a donor female mouse. After excision the tumor is fragmented by means of a pair of scissors in the NCTC 109 medium. After filtration through sterile gauze in order to remove large cellular fragments, the homogeneous cell suspension obtained is counted by means of a MALASSEZ cell and diluted to the desired concentration (4×10$^6$ tumor cells per ml) by dilution with the NCTC 109 medium.

Distribution in experimental groups

This was performed in the manner described for the leukemia L1210 (see above).

B. Protocol for treatment.

The doses of the products of the invention used in the different experiments are expressed in milligrams per kilogram of body weight.

The products to be injected were dissolved in isotonic sodium chloride solution.

2 protocols for treatment were used in the different experiments:
either a single injection on D1, by the intraperitoneal (I.P.) or intravenous (I.V.) route,
or 3 I.P. injections on D1, D5, D9.

In each experiment the animals of the control group received 1 or more injections, depending on the experimental protocol used, by the same route (I.P. or I.V.) of the same volume (0.2 ml/20 g) of the vehicle without the active principle (isotonic sodium chloride solution).

II. Expression of results

For each experiment a table specifies:
the number and percentage of the total of the mice surviving to D60,
the T/C×100 for the treated groups.

T representing the mean survival time of the mice in the treated group,

C representing the mean survival time of the mice in the control group (controls).

III Comment

The strains of mice used, the experimental protocols and the mode of expression of the results are in accordance with directive 271 F of the "N.C.I. Division of Cancer Treatment" (Nov. 1983).

IV. Pharmacological results

---
IC. 1625

L1210 USA - DBA$_2$ - I.P. treatment on D1, D5, D9
3 × 10 mg/kg

| T/C | Number of survivors at D60 |
|---|---|
| 190 | (0/10) |

---
IC. 1673

L1210 USA - B$_6$D$_2$F$_1$ - I.P. treatment on D1, D5, D9
3 × 1.25 mg/kg

| T/C | Number of survivors |
|---|---|
| 158 | (0/10) |

L1210 USA - B$_6$D$_2$F$_1$ - I.P. treatment on D1, D5, D9
3 × 5 mg/kg

| T/C | Number of survivors |
|---|---|
| 626 | (6/10) |

Melanoma B16 - B$_6$D$_2$F$_1$ - I.P. treatment on D1, D5, D9
3 × 10 mg/kg

| T/C | Number of survivors |
|---|---|
| 232 | (4/10) |

---
IC. 1591

L1210 strain USA - DBA$_2$ - I.P. treatment on D1
1 × 20 mg/kg

| T/C | Number of survivors on D60 |
|---|---|
| >600 | (7/10) |

L1210 strain USA - DBA$_2$ - I.P. treatment on D1, D5, D9
3 × 5 mg/kg

| T/C | Number of survivors on D60 |
|---|---|
| >600 | (6/10) |

L1210 strain USA - B$_6$D$_2$F$_1$ - I.P. treatment on D1, D5, D9
3 × 1.25 mg, 3 × 5 mg, 3 × 10 mg/kg

| | T/C | Number of survivors on D60 |
|---|---|---|
| 3 × 1.25 | 116 | (0/10) |
| 3 × 5 | 217 | (2/10) |
| 3 × 10 | 600 | (8/10) |

Melanoma B16 - B$_6$D$_2$F$_1$ - I.P. treatment of D1, D5, D9
3 × 10 mg/kg

| T/C | Number of survivors on D60 |
|---|---|
| 194 | (3/10) |

---
IC. 1626

L1210 strain USA - DBA$_2$ - I.P. treatment on D1
1 × 20 mg/kg

Number of survivors on D60: 3/10

L1210 strain USA - DBA$_2$ - I.P. treatment on D1, D5, D9
3 × 2.5 mg/kg, 3 × 10 mg/kg

| | T/C | Number of survivors on D60 |
|---|---|---|
| 3 × 2.5 | 150 | (0/10) |

-continued

| 3 × 10 | 275 | (3/10) |
|---|---|---|

| IC. 1627 |
|---|
| L1210 strain USA - DBA₂ - I.P. treatment on D1, 1 × 20 mg/kg |
| Number of survivors on D60: 3/10 |

| L1210 strain USA - DBA₂ - I.P. treatment on D1, D5, D9 3 × 2.5 mg/kg, 3 × 10 mg/kg | | |
|---|---|---|
| | T/C | Number of survivors on D60 |
| 3 × 2.5 | 141 | (0/10) |
| 3 × 10 | >600 | (6/10) |

V. Toxicological results

DLO, DL50, single I.P. dose administered to the aforementioned strains of mice.

For the compound in IC. 85-1625, the DLO is higher than or equal to 40 mg/kg.

For the compound in IC. 85-1590, the DLO is higher than or equal to 25 mg/kg.

For the compound in IC. 85-1591, the DLO is higher than or equal to 20 mg/kg.

For the compound in IC. 85-1626, the DLO is higher than or equal to 20 mg/kg.

For the compound in IC. 85-1627, the DLO is higher than or equal to 40 mg/kg.

For the compound in IC. 85-1673, the DL50 is approximately 20 mg/kg,

For the compounds in IC. 85-1591 and IC.85-1626, the DL50 is approximately 40 mg/kg.

We claim:

1. Process for the preparation of a nitrosourea derivative of formula I as follows:

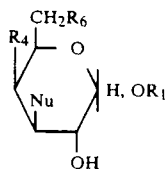

in which:

$R_1$ is alkyl of 1 to 12 carbon atoms or aralkyl of 7 to 12 carbon atoms or aralkyl of 7 to 12 carbon atoms substituted on the aromatic nucleus by one or more halogens or $NO_2$ or $CF_3$ groups or alkoxy groups of 1 to 4 carbon atoms, $R_4$ is hydrogen or halogen, $R_6$ is —OH or

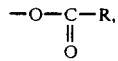

R is alkyl of 1 to 6 carbon atoms, aryl or aryl substituted by one or more halogens or $NO_2$ or $CF_3$ groups or alkoxy groups of 1 to 4 carbon atoms, Nu is

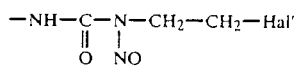

and

Hal' is halogen;

said process comprising the steps of:

(1) glycosylating a compound of formula II as follows:

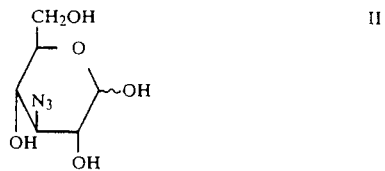

with an alcohol, $R_1OH$, in order to convert the —OH group at position 1 into an —$OR_1$ group;

(2) esterifying the glycosylated product of step 1 with an acid, R—COOH, in order to convert the —OH group at position 6 to a

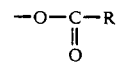

group;

(3) halogenating the esterified product of step 2 in order to introduce a halogen at position 4 and produce a halogenated compound of formula III as follows:

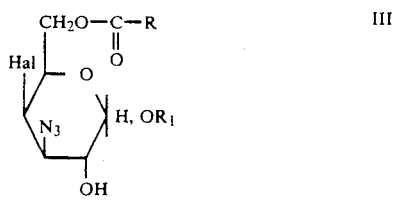

in which Hal is halogen;

(4) reducing the halogenated compound of formula III so as to reduce the —$N_3$ group at position 3 to a —$NH_2$ group;

(5) reacting the reduced product of step 4 with a halogeno-ethylisocyanate in order to convert the —$NH_2$ group at position 3 to a

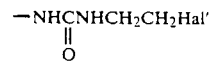

group; and then (6) reacting the isocyanate product of step 5 with an alkali metal nitrite in order to convert the

group at position 3 to a

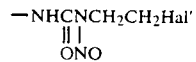

group.

2. The process of claim 1 wherein: $R_1$ is alkyl of 1 to 12 carbon atoms, aralkyl of 7 to 9 carbon atoms or aralkyl of 7 to 9 carbon atoms substituted by up to three halogens or $NO_2$ or $CF_3$ groups or alkoxy groups; and R is alkyl of 1 to 6 carbon atoms, aryl or aryl substituted by up to three halogens, NO₂ or CF₃ groups or alkoxy group of 1 to 4 carbon atoms.

3. The process of claim 2 wherein Hal' is chlorine and Hal is chlorine or bromine.

4. The process of claim 1 wherein the nitrosourea derivative of formula I is an α or β anomer, the compound of formula II is a mixture of α and β anomers, and the esterified product of step 2 is a mixture of esterified α and β anomers; and wherein the esterified α and β anomers, produced by step 2, are separated and then one or both of the esterified α and β anomers are halogenated in step 3, to produce the halogenated compound of formula III which is an α or β anomer.

5. The process of claim 1 wherein the halogen in position 4 on the halogenated compound of formula III is also reduced to hydrogen during step 4.

6. The process of claim 5 comprising the further step of hydrolyzing the

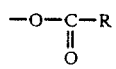

group at position 6 on the reduced product of step 4 to provide an —OH group at position 6 before reacting the reduced product of step 4 with the halogenoethylisocyanate.

7. The process of claim 1 comprising the further step of hydrolyzing the

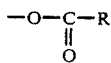

group at position 6 on the reduced product of step 4 to provide an —OH group at position 6 before reacting the reduced product of step 4 with the halogenoethylisocyanate.

8. The process of claim 1 wherein the alkali metal nitrite is sodium nitrite.

9. The process of claim 5 wherein the halogenated compound of formula III is reduced in step 4 with tributyl tin hydride in the presence of 2,2'-azobisisobutyronitrile.

10. The process of claim 9 wherein the alkali metal nitrite is sodium nitrite.

11. The process of claim 10 wherein the nitrosourea derivative of formula I is an α or β anomer, the compound of formula II is a mixture of α and β anomers, and the esterified product of step 2 is a mixture of esterified α and β anomers; and wherein the esterified α and β anomers, produced by step 2, are separated and then one or both of the esterified α and β anomers are halogenated in step 3 to produce the halogenated product of formula III which is an α or β anomer.

12. The process of claim 11 wherein Hal and Hal' are each chlorine.

13. A process comprising the steps of:
(1) glycosylating a compound of formula I as follows:

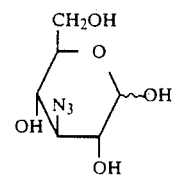

which is in the form of a mixture of α and β anomers, with an alcohol, R₁OH, in which R₁ is alkyl of 1 to 12 carbon atoms or aralkyl of 7 to 12 carbon atoms or aralkyl of 7 to 12 carbon atoms substituted on the aromatic nucleus by one or more halogens or NO₂ or CF₃ groups or alkoxy groups of 1 to 4 carbon atoms, to produce a glycosylated compound of formula II as follows:

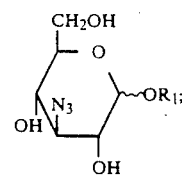

(2) esterifying the glycosylated compound of formula II with an acid, R—COOH, in which R is alkyl of 1 to 6 carbon atoms or aryl or aryl substituted by one or more halogens or NO₂ or CF₃ groups or alkoxy groups of 1 to 4 carbon atoms, to produce an esterified compound of formula III as follows:

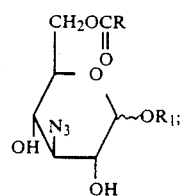

(3) separating the esterified compound of formula III into its α and β anomers of formula IV as follows:

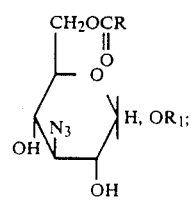

and then (4) halogenating one or both of the α and β anomers of the formula IV to produce a halogenated α- and/or β anomer of formula V as follows:

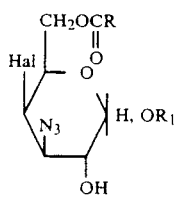

in which Hal is halogen.

14. A process for obtaining a nitrosourea derivative of formula I as follows:

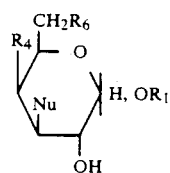

in which:
R$_4$ is Halogen,
R$_6$ is —OH or

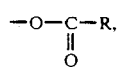

Nu is

R is alkyl of 1 to 6 carbon atoms, aryl or aryl substituted by one or more halogens or NO$_2$ or CF$_3$ groups or alkoxy groups of 1 to 4 carbon atoms, R$_1$ is alkyl of 1 to 12 carbon atoms or aralkyl of 7 to 12 carbon atoms or aralkyl of 7 to 12 carbon atoms substituted on the aromatic nucleus by one or more halogens or NO$_2$ or CF$_3$ groups or alkoxy groups of 1 to 4 carbon atoms, and Hal' is halogen, comprising the steps of:
(1) reducing a halogenated compound of formula II as follows:

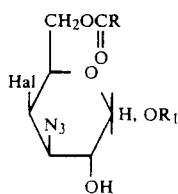

in which Hal is halogen,
so that the —N$_3$ group at position 3 is reduced to a —NH$_2$ group without hydrogenolysis of the halogen at position 4, to produce a reduced compound of formula III as follows:

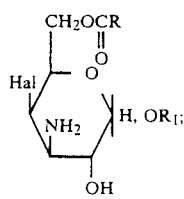

and then
(2) reacting the reduced compound of formula III with a halogeno-ethylisocyanate in order to convert the —NH$_2$ group at position 3 to a

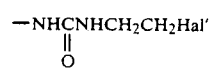

group, and then with an alkali metal nitrite in order to convert the

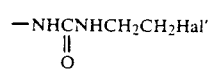

group at position 3 to a

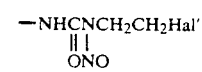

group and form a nitrosourea derivative of formula IA as follows:

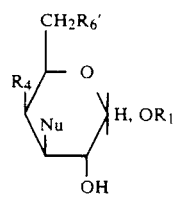

in which:

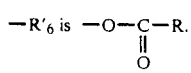

15. The process of claim 14 wherein the reduced compound of formula III is: hydrolyzed in order to remove the

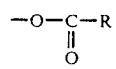

group at position 6 and to replace this group with an —OH group; and then reacted in step 2 with the halogeno-ethylisocyanate and then with the alkali metal nitrite to form a nitrosourea derivative of formula IB as follows:

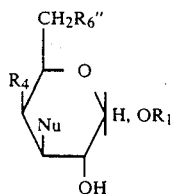 IB in which $R_6''$ is —OH.

16. A process for obtaining a nitrosourea derivative of formula I as follows:

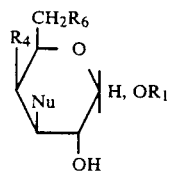 I in which:
$R_4$ is hydrogen,
$R_6$ is —OH or

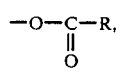

Nu is

R is alkyl of 1 to 6 carbon atoms, aryl or aryl substituted by one or more halogens or $NO_2$ or $CF_3$ groups or alkoxy groups of 1 to 4 carbon atoms,
$R_1$ is alkyl of 1 to 12 carbon atoms or aralkyl of 7 to 12 carbon atoms or aralkyl of 7 to 12 carbon atoms substituted on the aromatic nucleus by one or more halogens or $NO_2$ or $CF_3$ groups or alkoxy groups of 1 to 4 carbon atoms, and
Hal' is halogen,
comprising the steps of:
(1) reducing a halogenated compound of formula II as follows:

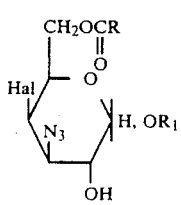 II in which Hal is halogen,
so that the halogen at position 4 is replaced by H and the —$N_3$ group at position 3 is reduced to a —$NH_2$ group to give a reduced compound of formula III as follows:

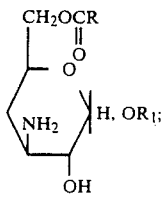 III and then
(2) reacting the reduced compound of formula III with a halogeno-ethylisocyanate in order to convert the —$NH_2$ group at position 3 to a

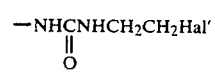

group and then with an alkali metal nitrite in order to convert the

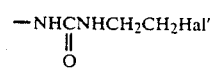

group at position 3 to a

group and form a nitrosourea derivative of formula IA as follows:

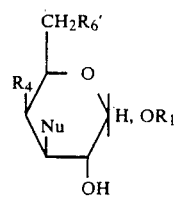 IA in which $R'_6$ is

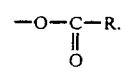

17. The process of claim 16 wherein the reduced compound of formula III is: hydrolyzed to remove the

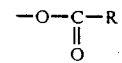

group at position 6 and to replace this group with an —OH group; and then reacted in step 2 with the halogeno-ethylisocyanate and then with the alkali metal nitrite to form a nitrosourea derivative of formula IB as follows:

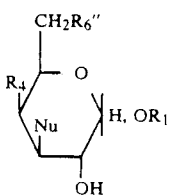

IB in which R″$_6$ is —OH.

18. The process of claim 16 wherein the halogenated compound of formula II is reduced in step 1 by means of tributyl tin hydride in the presence of 2,2′-azobisisobutyronitrile.

19. The process of claim 1 wherein the compound of formula II is glycosylated in step 1 with CH$_3$OH.

20. The process of claim 19 wherein the glycosylated product of step 1 is esterified in step 2 with bis tributyl tin oxide and benzoyl chloride in order to introduce a benzoyl group at position 6.

21. The process of claim 20 wherein the esterified product of step 2 is halogenated with SO$_2$Cl$_2$ or SO$_2$Br$_2$ in step 3.

22. The process of claim 21 wherein the halogenated compound of formula III is reduced in step 4 by catalytic hydrogenation so as to reduce the —N$_3$ group to the —NH$_2$ group without reducing the —Cl or —Br at position 4 to hydrogen.

23. The process of claim 22 wherein the alkali metal nitrite is sodiun nitrite.

24. The process of claim 22 wherein the benzoyl group at position 6 of the reduced product of step 4 is hydrolyzed with a base, before step 5, so as to replace the benzoyl group at position 6 with an —OH group.

25. The process of claim 24 wherein the base is an alkali alcoholate.

26. A compound of the formula:

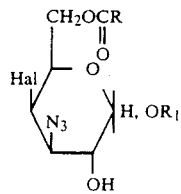

in the form of an α or β anomer or a mixture thereof in which:

Hal is halogen,

R$_1$ is alkyl of 1 to 12 carbon atoms, aralkyl of 7 to 12 carbon atoms or aralkyl of 7 to 12 carbon atoms substituted on the aromatic nucleus by one or more halogens or NO$_2$ or CF$_3$ groups or alkoxy groups of 1 to 4 carbon atoms and R is alkyl of 1 to 6 carbon atoms, aryl or aryl substituted by one or more halogens or NO$_2$ or CF$_3$ groups or alkoxy groups of 1 to 4 carbon atoms.

27. The compound of claim 26 wherein R$_1$ is alkyl, aralkyl of 7 to 9 carbon atoms or substituted aralkyl of 7 to 9 carbon atoms and Hal is chlorine.

28. The compound of claim 26 wherein R$_1$ is alkyl and R is benzyl.

29. The compound of claim 26, having the formula:

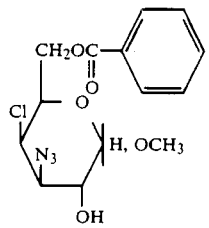

* * * * *